United States Patent
Acton et al.

(10) Patent No.: US 11,174,248 B2
(45) Date of Patent: Nov. 16, 2021

(54) INDAZOLYL-SPIRO[2.3]HEXANE-CARBONITRILE DERIVATIVES AS LRRK2 INHIBITORS, PHARMACEUTICAL COMPOSITIONS, AND USES THEREOF

(71) Applicant: Merck Sharp & Dohme Corp., Rahway, NJ (US)

(72) Inventors: John Acton, Cranford, NJ (US); David Annunziato Candito, Wrentham, MA (US); J. Michael Ellis, Needham, MA (US); Peter H. Fuller, Ashland, MA (US); Hakan Gunaydin, Somerville, MA (US); Blair T. Lapointe, Sudbury, MA (US); Weiguo Liu, Princeton, NJ (US); Joey L. Methot, Westwood, MA (US); Santhosh F. Neelamkavil, Edison, NJ (US); Barbara Pio, West Orange, NJ (US); Vladimir Simov, South Boston, MA (US); Harold B. Wood, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/755,177

(22) PCT Filed: Oct. 8, 2018

(86) PCT No.: PCT/US2018/054790
§ 371 (c)(1),
(2) Date: Apr. 10, 2020

(87) PCT Pub. No.: WO2019/074810
PCT Pub. Date: Apr. 18, 2019

(65) Prior Publication Data
US 2021/0188818 A1    Jun. 24, 2021

Related U.S. Application Data

(60) Provisional application No. 62/570,812, filed on Oct. 11, 2017.

(51) Int. Cl.
| | |
|---|---|
| A61K 31/506 | (2006.01) |
| C07D 403/14 | (2006.01) |
| C07D 401/14 | (2006.01) |
| C07D 405/14 | (2006.01) |
| C07D 413/14 | (2006.01) |
| C07D 498/04 | (2006.01) |
| C07D 498/10 | (2006.01) |
| C07D 519/00 | (2006.01) |

(52) U.S. Cl.
CPC ........ *C07D 403/14* (2013.01); *C07D 401/14* (2013.01); *C07D 405/14* (2013.01); *C07D 413/14* (2013.01); *C07D 498/04* (2013.01); *C07D 498/10* (2013.01); *C07D 519/00* (2013.01)

(58) Field of Classification Search
None
See application file for complete search history.

(56) References Cited

U.S. PATENT DOCUMENTS

2016/0326151 A1    11/2016   Gummadi

FOREIGN PATENT DOCUMENTS

| WO | 2008040753 A1 | 4/2008 |
| WO | 2016036586 A1 | 3/2016 |

OTHER PUBLICATIONS

Galatsis, Paul, Leucine-rich repeat kinase 2 inhibitors: a patent review (2014-2016), Expert Opinion on Therapeutic Patents, 2017, 667-676, 27(6).
International Search Report dated Jan. 22, 2019, 11 pages.

*Primary Examiner* — Samantha L Shterengarts
(74) *Attorney, Agent, or Firm* — Sylvia A. Ayler; Catherine D. Fitch

(57) ABSTRACT

The present invention is directed to substituted certain reversed indazole compounds of Formula (I): and pharmaceutically acceptable salts thereof, wherein $R^{1A}$, $R^{1B}$, X, Y, $R^Z$ and $R^2$ are as defined herein, which are potent inhibitors of LRRK2 kinase and useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of such diseases in which LRRK-2 kinase is involved.

(I)

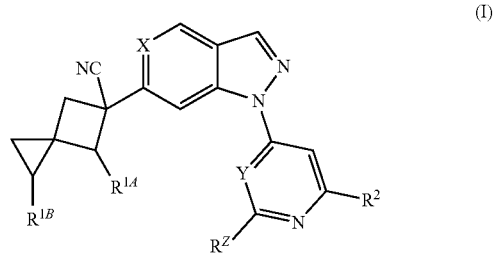

11 Claims, No Drawings

INDAZOLYL-SPIRO[2.3]HEXANE-CARBONITRILE DERIVATIVES AS LRRK2 INHIBITORS, PHARMACEUTICAL COMPOSITIONS, AND USES THEREOF

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27.). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8.). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and parkinson's linked to chromosome 17 (Goedert and Jakes Biochim Biophys Acta. 2005 Jan. 3.).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5): 1602-11.). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6.).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscluar disease, 2010) and ankylosing spondylitis (Danoy et al., PLoS Genet. 2010 Dec. 2; 6(12).). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41.). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain indazolyl-spiro[2.3]hexane-carbonitrile derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of the invention I), each of which possess a spiro[2.3]hexane-carbonitrile, exhibit excellent LRRK2 inhibitory activity. In some embodiments, the compounds of the invention exhibit unexpectedly superior potency as inhibitors of LRRK2 kinase, as evidenced by the data reported herein. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (I):

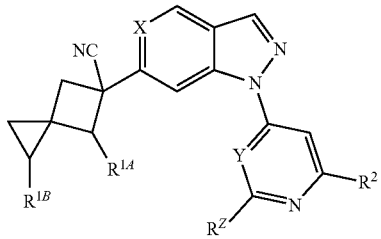

(I)

or a pharmaceutically acceptable salt thereof, wherein:
$R^{1A}$ is H or $CH_3$;
$R^{1B}$ is H or $CH_3$;
X is $C(R^X)$ or N;
$R^X$ is H, F, Cl, or $-(C_1-C_6)$alkyl;
Y is CH or N;
$R^Z$ is H, F, $-(C_1-C_6)$alkyl, $-NH_2$, $-NH(C_1-C_6)$alkyl, $-N((C_1-C_6)$alkyl$)_2$, $-O(C_1-C_6)$alkyl, $-S(C_1-C_6)$alkyl, $-(C_1-C_6)$alkyl-OH, $-(C_1-C_6)$alkyl-O$-(C_1-C_6)$alkyl,

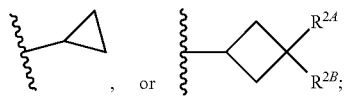

$R^2$ is $-(C_1-C_6)$alkyl, $-(C_1-C_6)$alkyl-OH,

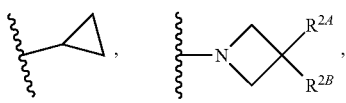

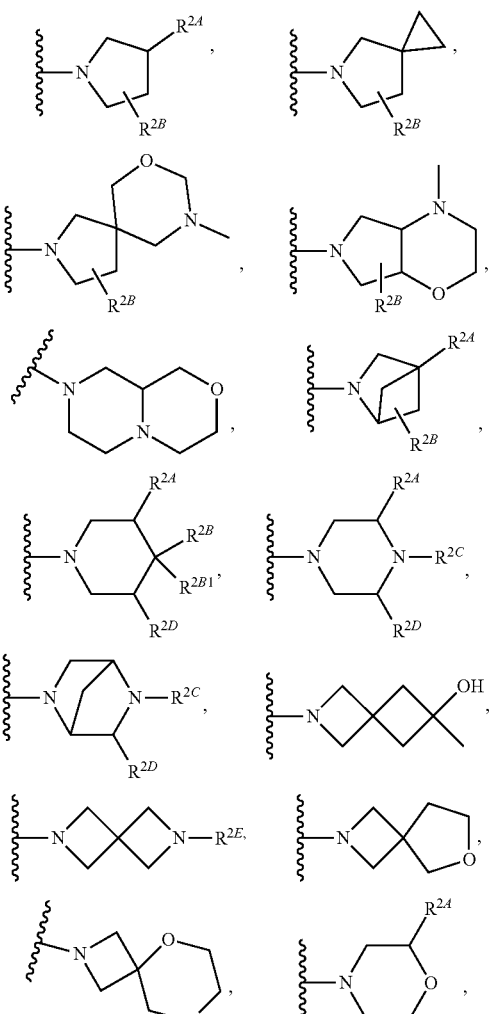

wherein:
$R^{2A}$ is H, F, $-$OH, $-(C_1-C_6)$alkyl, $-(C_1-C_6)$haloalkyl, $-$O$-(C_1-C_6)$alkyl, $C(OH)((C_1-C_6)$alkyl$)_2$, $(C_1-C_6)$alkyl-OH; $-(C_1-C_6)$alkyl-O$-(C_1-C_6)$alkyl, $-C(C_1-C_6)$alkyl$)_2$(OH), cyclopropyl, or

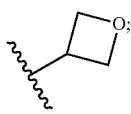

$R^{2B}$ is H, F, $-$OH, $-(C_1-C_6)$alkyl, $C((C_1-C_6)$alkyl$)_2$(OH), $-(C_1-C_6)$alkyl-OH, $-(C_1-C_6)$alkyl-O$-(C_1-C_6)$alkyl, or

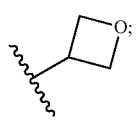

$R^{2B1}$ is H, F, or —$(C_1-C_6)$alkyl;
$R^{2C}$ is H, —$(C_1-C_6)$alkyl, —$SO_2$—$(C_1-C_6)$alkyl,

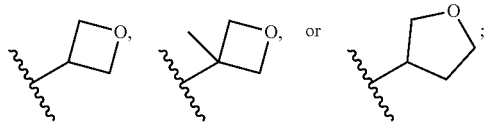

$R^{2D}$ is H, —$(C_1-C_6)$alkyl, —$(C_1-C_6)$alkyl-OH, or —$(C_1-C_6)$alkyl-O—$(C_1-C_6)$alkyl; and
$R^{2E}$ is H, —$(C_1-C_6)$alkyl, —$(C_1-C_6)$haloalkyl,

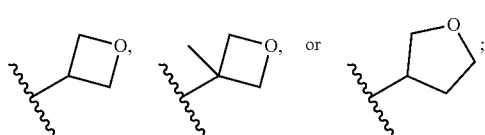

$R^{2F}$ is H, —$(C_1-C_6)$alkyl, —$(C_1-C_6)$fluoroalkyl, —$(C_1-C_6)$alkyl-O—$(C_1-C_6)$alkyl,

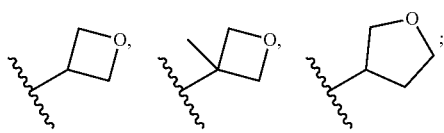

and
$R^{2G}$ is H, —$(C_1-C_6)$alkyl, or —$(C_1-C_6)$haloalkyl.

In another embodiment, the compounds of the invention have the structural Formula (I.1):

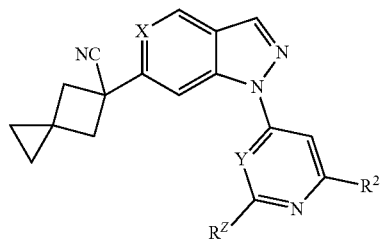

(I.1)

or a pharmaceutically acceptable salt thereof, wherein:
X is $C(R^X)$ or N;
$R^X$ is H, F, Cl, or $CH_3$;
Y is CH or N;
$R^Z$ is H, —$CH_3$, —$NHCH_3$, —O—$CH_3$, or —$CH_2$O—$CH_3$;

$R^2$ is

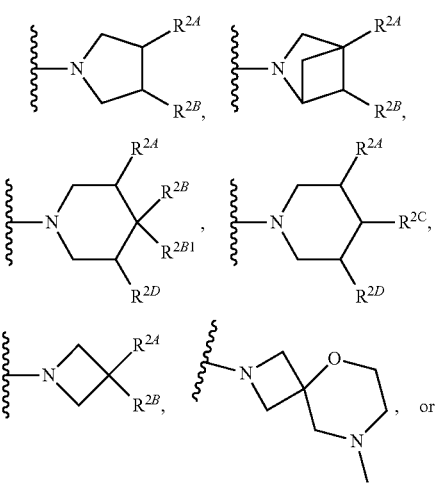

wherein:
$R^{2A}$ is H, F, —OH, —$CH_3$, —$OCH_3$, —$C(OH)(CH_3)_2$, —$CH_2OH$, —$CH_2$O—$CH_3$, —$C(CH_3)_2(OH)$, cyclopropyl, or

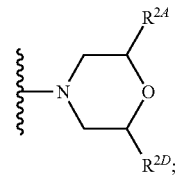

$R^{2B}$ is H, F, —OH, —$CH_3$, —$C(OH)(CH_3)_2$, —$CH_2OH$, —$CH_2$O—$CH_3$, or

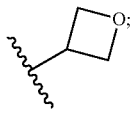

$R^{2B1}$ is H, F, or $CH_3$;
$R^{2C}$ is H, —$CH_3$, —$S(O)_2CH_3$;

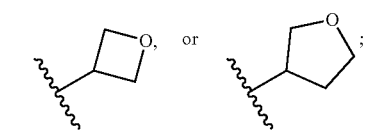 [SMILES: *C1COC1 ; "or" ; *C1CCOC1 ; ";"]

and
$R^{2D}$ is H, $CH_3$, —$CH_2OH$, or —$CH_2OCH_3$.

In one embodiment, the compounds of the invention have the structural Formula (I'):

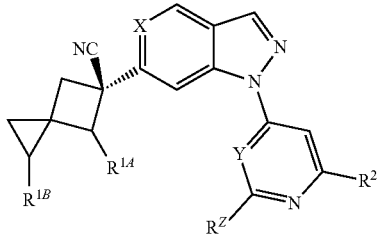

(I')

or a pharmaceutically acceptable salt thereof, wherein:
$R^{1A}$, $R^{1B}$; X, Y, $R^Z$ and $R^2$ are defined in Formula (I).
In another embodiment of Formula (I'):
$R^{1A}$ is H;
$R^{1B}$ is $CH_3$; and,
X, Y, $R^Z$ and $R^2$ are defined in Formula (I).
$R^{1A}$ is $CH_3$;
$R^{1B}$ is H; and;
X, Y, $R^Z$ and $R^2$ are defined in Formula (I).
In one embodiment, the compounds of the invention have the structural Formula (I"):

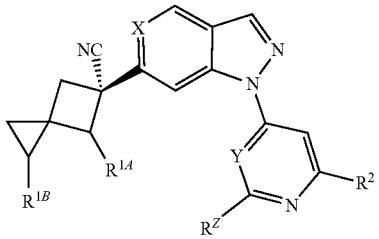

(I")

or a pharmaceutically acceptable salt thereof, wherein $R^{1A}$, $R^{1B}$, X, Y, $R^Z$ and $R^2$ are defined in Formula (I).
In another embodiment of Formula (I"):
$R^{1A}$ is H;
$R^{1B}$ is $CH_3$; and;
X, Y, $R^Z$ and $R^2$ are defined in Formula (I).
In another embodiment of Formula (I"):
$R^{1A}$ is $CH_3$;
$R^{1B}$ is H; and;
X, Y, $R^Z$ and $R^2$ are defined in Formula (I).
In another embodiment, in Formula (I), X is $C(R^X)$ and the compounds of the invention have the structural Formula (IA):

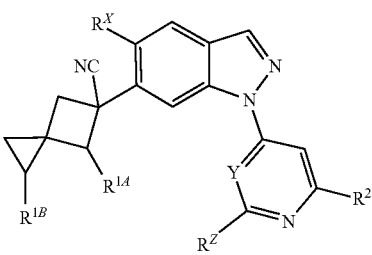

(IA)

or a pharmaceutically acceptable salt thereof, wherein:
$R^X$ is H, F, Cl, or $CH_3$;
Y is CH or N; and
$R^{1A}$, $R^{1B}$; $R^Z$ and $R^2$ are as defined in Formula (I).
In another embodiment, in Formula (IA),
$R^{1A}$ is H;
$R^{1B}$ is H;
$R^X$ is H, F, Cl, or $CH_3$;
Y is CH or N; and
$R^Z$ and $R^2$ are as defined in Formula (I).
In another embodiment, in Formula (IA),
$R^{1A}$ is H;
$R^{1B}$ is $CH_3$;
$R^X$ is H, F, Cl, or $CH_3$;
Y is CH or N; and
$R^Z$ and $R^2$ are as defined in Formula (I).
In another embodiment, in Formula (IA),
$R^{1A}$ is H;
$R^{1B}$ is $CH_3$;
$R^X$ is H, F, Cl, or $CH_3$;
Y is CH or N; and
$R^Z$ and $R^2$ are as defined in Formula (I) or Formula (I.1).
In an alternative of each of the preceeding embodiments of Formula (IA), Y is CH.
In another alternative of each of the preceeding embodiments of Formula (IA), Y is N.
In another embodiment, in Formula (I.1), X is $C(R^X)$ and the compounds of the invention have the structural Formula (IA.1):

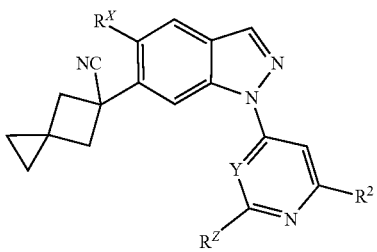

(IA.1)

or a pharmaceutically acceptable salt thereof, wherein:
$R^X$ is H, F, Cl, or $CH_3$;
Y is CH or N;
and $R^Z$ and $R^2$ are as defined in Formula (I) or Formula (I.1).
In an alternative embodiment of Formula (IA.1), Y is CH.
In another alternative embodiment of Formula (IA.1), Y is N.
In another embodiment, in Formula (I'), X is $C(R^X)$ and the compounds of the invention have the structural Formula (IA'):

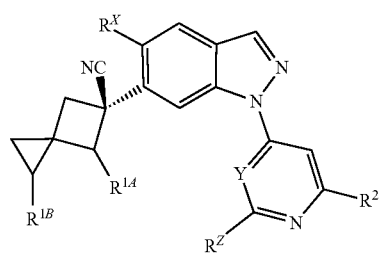

(IA')

or a pharmaceutically acceptable salt thereof, wherein:
$R^X$ is H, F, Cl, or $CH_3$;
Y is CH or N; and
one of $R^{1A}$ and $R^{1B}$ is H and the other is $CH_3$; and
$R^Z$ and $R^2$ are as defined in Formula (I) or Formula (I.1).
In another embodiment, in Formula (IA'):
$R^{1A}$ is $CH_3$;
$R^{1B}$ is H;
Y is CH or N; and
$R^Z$ and $R^2$ are as defined in Formula (I) or Formula (I.1).
In another embodiment, in Formula (IA'):
$R^{1A}$ is $CH_3$;
$R^{1B}$ is H;
Y is CH; and
$R^Z$ and $R^2$ are as defined in Formula (I) or Formula (I.1).
In another embodiment, in Formula (IA'):
$R^{1A}$ is $CH_3$;
$R^{1B}$ is H;
Y is N; and
$R^Z$ and $R^2$ are as defined in Formula (I) or Formula (I.1).
In another embodiment, in Formula (IA'):
$R^{1A}$ is H;
$R^{1B}$ is $CH_3$;
Y is CH or N; and
$R^Z$ and $R^2$ are as defined in Formula (I) or Formula (I.1).
In another embodiment, in Formula (IA'):
$R^{1A}$ is H;
$R^{1B}$ is $CH_3$;
Y is CH; and
$R^Z$ and $R^2$ are as defined in Formula (I) or Formula (I.1).
In another embodiment, in Formula (IA'):
$R^{1A}$ is H;
$R^{1B}$ is $CH_3$;
Y is N; and
$R^Z$ and $R^2$ are as defined in Formula (I) or Formula (I.1).
In an alternative of each of the preceeding embodiments and alternative embodiments of Formula (IA'), Y is CH.
In another alternative of each of the preceeding embodiments and alternative embodiments of Formula (IA'), Y is N.
In another embodiment, in Formula (I"), X is $C(R^X)$ and the compounds of the invention have the structural Formula (IA"):

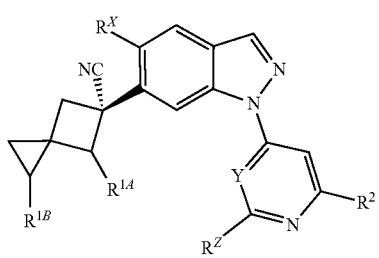

(IA")

or a pharmaceutically acceptable salt thereof, wherein:
one of $R^{1A}$ and $R^{1B}$ is H and the other is $CH_3$;
$R^X$ is H, F, Cl, or $CH_3$;
Y is CH or N;
and $R^Z$ and $R^2$ are as defined in Formula (I) or Formula (I.1).
In another embodiment, in Formula (IA"):
$R^{1A}$ is H;
$R^{1B}$ is $CH_3$;
$R^X$ is H, F, Cl, or $CH_3$;
Y is CH or N;
and $R^Z$ and $R^2$ are as defined in Formula (I) or Formula (I.1).
In another embodiment, in Formula (IA"):
$R^{1A}$ is $CH_3$;
$R^{1B}$ is H;
$R^X$ is H, F, Cl, or $CH_3$;
Y is CH or N;
and $R^Z$ and $R^2$ are as defined in Formula (I) or Formula (I.1).
In an alternative of each of the preceeding embodiments and alternative embodiments of Formula (IA"), Y is CH.
In another alternative of each of the preceeding embodiments and alternative embodiments of Formula (IA"), Y is N.
In an alternative embodiment of Formula (IA.1"), Y is CH.
In another alternative embodiment of Formula (IA.1"), Y is N.
In another embodiment, in Formula (I), X is N and the compounds of the invention have the structural Formula (IB.1):

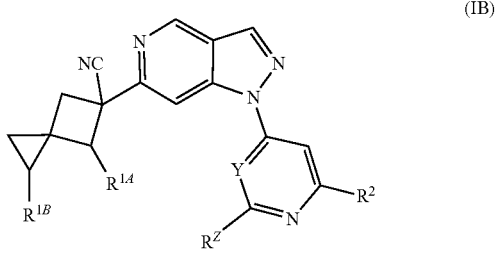

(IB)

or a pharmaceutically acceptable salt thereof, wherein:
$R^{1A}$ is H or $CH_3$;
RIB is H or $CH_3$;
Y is CH or N;
and $R^Z$ and $R^2$ are as defined in Formula (I).
In another embodiment, in Formula (IB):
$R^{1A}$ is H;
$R^{1B}$ is H;
Y is CH or N;
and $R^Z$ and $R^2$ are as defined in Formula (I).
In another embodiment, in Formula (IB):
$R^{1A}$ is H;
$R^{1B}$ is $CH_3$;
Y is CH or N;
and $R^Z$ and $R^2$ are as defined in Formula (I).
In another embodiment, in Formula (IB):
$R^{1A}$ is $CH_3$;
$R^{1B}$ is H;
Y is CH or N;
and $R^Z$ and $R^2$ are as defined in Formula (I).
In an alternative of each of the preceeding embodiments and alternative embodiments of Formula (IB), Y is CH.
In another alternative of each of the preceeding embodiments and alternative embodiments of Formula (IB), Y is N.

In another embodiment, in Formula (I.1), X is N and the compounds of the invention have the structural Formula (IB.1):

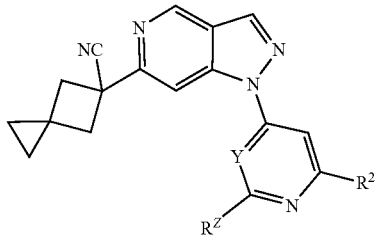

(IB.1)

or a pharmaceutically acceptable salt thereof, wherein:
Y is CH or N;
and $R^Z$ and $R^2$ are as defined in Formula (I.1).

In an alternative embodiment of Formula (IB.1), Y is CH.

In another alternative embodiment of Formula (IB.1), Y is N.

In another embodiment, in Formula (I'), X is N and the compounds of the invention have the structural Formula (IB'):

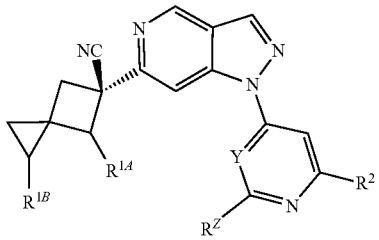

(IB')

or a pharmaceutically acceptable salt thereof, wherein:
one of $R^{1A}$ and $R^{1B}$ is H and the other is $CH_3$;
Y is CH or N;
and $R^Z$ and $R^2$ are as defined in Formula (I).

In another embodiment, in Formula (IB'):
$R^{1A}$ is $CH_3$;
$R^{1B}$ is H;
Y is CH or N;
and $R^Z$ and $R^2$ are as defined in Formula (I).

In another embodiment, in Formula (IB'):
$R^{1A}$ is H;
$R^{1B}$ is $CH_3$;
Y is CH or N;
and $R^Z$ and $R^2$ are as defined in Formula (I).

In an alternative of each of the preceeding embodiments and alternative embodiments of Formula (IB'), Y is CH.

In another alternative of each of the preceeding embodiments and alternative embodiments of Formula (IB'), Y is N.

In another embodiment, in Formula (I"), X is N and the compounds of the invention have the structural Formula (IB"):

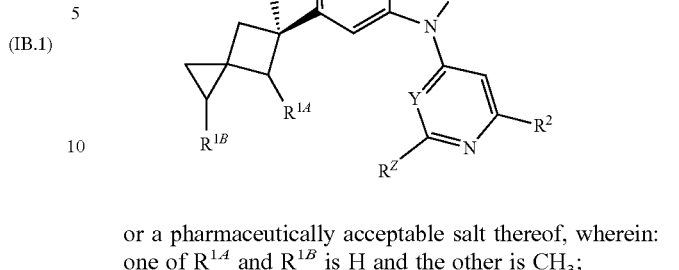

(IB")

or a pharmaceutically acceptable salt thereof, wherein:
one of $R^{1A}$ and $R^{1B}$ is H and the other is $CH_3$;
Y is CH or N;
and $R^Z$ and $R^2$ are as defined in Formula (I).

In another embodiment, in Formula (IB"):
$R^{1A}$ is H;
$R^{1B}$ is $CH_3$;
Y is CH or N;
and $R^Z$ and $R^2$ are as defined in Formula (I).

In another embodiment, in Formula (IB"):
$R^{1A}$ is $CH_3$;
$R^{1B}$ is H;
Y is CH or N;
and $R^Z$ and $R^2$ are as defined in Formula (I).

In an alternative of each of the preceeding embodiments and alternative embodiments of Formula (IB"), Y is CH.

In another alternative of each of the preceeding embodiments and alternative embodiments of Formula (IB"), Y is N.

In another alternative embodiment, in each of Formulas (I), (I'), (I"), (IA), (IA'), (IA"), (IB), (IB'), and (IB"), and in each of the alternative embodiments thereof described above,
$R^X$ (when present) is H, F, Cl, or $CH_3$.

In another alternative embodiment, in each of Formulas (I), (I.1), (I'), (IA), (IA'), (IA"), (IB), (IB'), and (IB"), and in each of the alternative embodiments thereof described above,
$R^Z$ is H, —$CH_3$, —$NHCH_3$, —O—$CH_3$, or —$CH_2$O—$CH_3$.

In another alternative embodiment, in each of Formulas (I), (I.1), (I'), (IA), (IA'), (IA"), (IB), (IB'), and (IB"), and in each of the alternative embodiments thereof described above,
$R^{2A}$ (when present) is H, F, —OH, —$CH_3$, —$OCH_3$, C(OH)(CH_3)_2, —$CH_2OH$, —$CH_2$O—$CH_3$, —$C(CH_3)_2$(OH), cyclopropyl, or

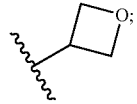 [SMILES: *C1COC1]

$R^{2B}$ (when present) is H, F, —OH, —$CH_3$, $C(OH)(CH_3)_2$, —$CH_2OH$, —$CH_2$O—$CH_3$, or

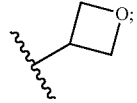 [SMILES: *C1COC1]

$R^{2B1}$ (when present) is H, F, or $CH_3$;
$R^{2C}$ (when present) is H, —$CH_3$, —$S(O)_2CH_3$;

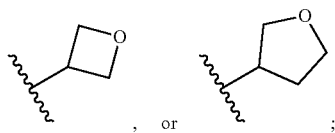 [SMILES: *C1COC1 ; *C1CCOC1]

and
$R^{2D}$ (when present) is H, $CH_3$, —$CH_2OH$, $C(OH)(CH_3)_2$, or —$CH_2OCH_3$.

In another alternative embodiment, in each of Formulas (I), (I'), (I"), (IA), (IA'), (IA"), (IB), (IB'), and (IB"), and in each of the alternative embodiments thereof described above,
$R^X$ (when present) is H, F, Cl, or $CH_3$;
$R^Z$ is H, —$CH_3$, —$NHCH_3$, —O—$CH_3$, or —$CH_2O$—$CH_3$;
$R^{2A}$ (when present) is H, F, —OH, —$CH_3$, —$OCH_3$, $C(OH)(CH_3)_2$, —$CH_2OH$, —$CH_2O$—$CH_3$, —$C(CH_3)_2(OH)$, cyclopropyl, or

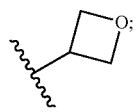

$R^{2B}$ (when present) is H, F, —OH, —$CH_3$, $C(OH)(CH_3)_2$, —$CH_2OH$, —$CH_2O$—$CH_3$, or

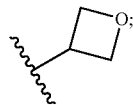

$R^{2B1}$ (when present) is H, F, or $CH_3$;
$R^{2C}$ (when present) is H, —$CH_3$, —$S(O)_2CH_3$;

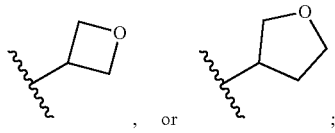

and
$R^{2D}$ (when present) is H, $CH_3$, —$CH_2OH$, $C(OH)(CH_3)_2$, or —$CH_2OCH_3$.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl $CH_2C(O)$— groups (keto forms) may undergo tautomerism to form hydroxyl CH=C (OH)— groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"($C_1$-$C_6$)Alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halogen atom. As appreciated by those of skill in the art, "halo" or "halogen" as used herein is intended to include chloro (Cl), fluoro (F), bromo (Br) and iodo (I). Chloro (Cl) and fluoro(F) halogens are generally preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the present invention can be prepared readily according to the following schemes and specific examples, or modifications thereof, using readily available starting materials, reagents and conventional synthesis procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

Abbreviations used in the experimentals may include, but are not limited to the following:

| | | | |
|---|---|---|---|
| ACN | Acetonitrile | AcOH | Acetic acid |
| Aq | Aqueous | Bn | Benzyl |
| BOC | tert-Butoxycarbonyl | BOC$_2$O Boc$_2$O | BOC Anhydride |
| Bu | Butyl | C. (or °C.) | degrees Celsius |
| Cbz | Benzyloxycarbonyl | CD$_3$OD | Methanol-d4 |
| CDCl$_3$ | Chloroform-d | CH$_2$Cl$_2$ | Dichloromethane |
| CH$_3$CN | Acetonitrile | CPME | Cyclopentyl methyl ether |
| Cs$_2$CO$_3$ | Cesium carbonate | DCM | Dichloromethane |
| DIEA | Diisopropylethylamine | DME | 1,2-dimethoxyethane |
| DMF | Dimethylformamide | DMSO | Dimethyl sulfoxide |
| Eq | Equivalents | Et | Ethyl |
| EtOAc | Ethyl acetate | EtOH | Ethanol |
| g | grams | h, hr | hours |
| $^1$H | proton | HCl | Hydrogen chloride (gas or solution in organic solvent) or hydrochloric acid (aqueous solution) |
| Hex | hexanes | HPLC | High pressure liquid chromatography |
| IPA | isopropanol, 2-propanol | iPrOAc | isopropyl acetate |
| Josiphos Pd G3 | Methanesulfonato{(R)-(–)-1-[(S)-2-(dicyclohexylphosphino)ferrocenyl]ethyldi-t-butylphosphine}(2'-amino-1,1'-biphenyl-2-yl)palladium(II) | LiHMDS | Lithium hexamethyldisilazane or lithium bis(trimethylsilyl)amide |
| LDA | lithium diisopropylamide | M | Molar |
| Me | Methyl | MeCN | Acetonitrile |
| MeOH | Methanol | MHz | Megahertz |
| mg | Milligrams | MgSO$_4$ | magnesium sulfate |
| min | Minutes | mL (or ml) | Milliliter |
| mmol | milimole | MPLC | Medium Pressure Liquid Chromatography / flash chromatography |
| MS | Mass Spectroscopy | MTBE | Methyl tert-butyl ether |
| N | normal | N$_2$ | nitrogen gas |
| Na$_2$SO$_4$ | sodium sulfate | NH$_4$Cl | ammonium chloride |
| NMP | 1-methyl-2-pyrrolidone | NMR | Nuclear Magnetic Resonance |
| ON | Overnight | OXONE™ | Potassium peroxymonosulfate compound |
| Pd-C | Palladium on Carbon | PTLC | Preparative thin layer chromatography |
| RT or rt | Room temperature | sat (or sat. or sat'd.) | Saturated |
| SFC | supercritical fluid chromatography | tBOC | tert-Butoxycarbonyl |
| t-Bu | tert-butyl | TEA | Triethylamine |
| TFA | Trifluoroacetic acid | THF | Tetrahydrofuran |
| TLC | Thin layer chromatography | Ts | Toluene sulfonyl |

-continued

~ Approximately

N-Xantphos Pd G4

N-XantPhos-Pd-G4

General Experimental Information

Unless otherwise noted, all reactions are magnetically stirred.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, silica gel chromatography is carried out on an Isco, Analogix, or Biotage automated chromatography system using a commercially available cartridge as the column. Columns may be purchased from Isco, Analogix, Biotage, Varian, or Supelco and are filled with silica gel as the stationary phase.

Unless otherwise noted, all MS data reported was obtained from an LCMS experiment. MS method is electrospray (positive ion).

Unless otherwise noted, all LRRK2 $IC_{50}$ data presented in tables refers to the LRRK2 Km ATP LanthaScreen™ Assay that is described in the Biological Assay section.

Intermediates

Intermediate compounds of the present invention can be synthesized according to the schemes and procedures outlined below, wherein each variable is as defined in Formula I unless otherwise specified. Because the schemes are an illustration, the invention should not be construed as being limited by the chemical reactions and conditions expressed. The preparation of the various starting materials used in the schemes is within the skill of a person versed in the art.

SCHEME A

Hal = Cl, Br
X = C, N

A-1

A-2 ligand/Pd Precat
LiHMDS
─────────────→
CPME/THF
60° C.

intermediate A

Intermediate A was prepared according to scheme A. Haloindazole A-1 and spirocyclic nitrile A-2 were combined under the action of an appropriate metal catalyst and ligand, base, solvent and temperature to directly provide Intermediate A.

Intermediate A1

5-(1H-indazol-6-yl)spiro[2.3]hexane-5-carbonitrile
(Scheme A)

Step 1: 5-(1H-indazol-6-yl)spiro[2.3]hexane-5-carbonitrile 6-bromo-1H-indazole (1.478 g, 7.5 mmol) and spiro[2.3]hexane-5-carbonitrile (0.964 g, 9.00 mmol) were added to a reaction flask, which was then sealed and placed under a nitrogen atmosphere by performing 3 vacuum/nitrogen purge cycles. CPME (18.75 ml) was added and the mixture was stirred. In a separate flask was added N-Xantphos Pd G4 (0.351 g, 0.375 mmol) and THF (18.75 ml). This flask was also sealed and placed under nitrogen atmosphere with 3 vacuum/nitrogen purge cycles. After stirring the precatalyst/THF for 5 minutes, it was added to the stirring CPME solution of bromoindazole and nitrile via syringe. Then 1.0 M LiHMDS (22.50 ml, 22.50 mmol) in THF was added and the resulting mixture stirred at 60° C. until complete. Cooled to room temperature, then quenched with aqueous $NH_4Cl$ and extracted with EtOAc. Dried organic over Na$_2$SO$_4$, filtered and evaporated. The crude was purified on a silica gel column, eluting with EtOAc in hexanes to give the title compound. $^1$H NMR (500 MHz, CDCl$_3$): δ 10.24 (s, 1H), 8.11 (s, 1H), 7.84 (d, J=8.5 Hz, 1H), 7.69 (s, 1H), 7.41 (dd, J=8.5, 1.5 Hz, 1H), 3.05 (d, 13 Hz, 2H), 2.84 (d, J=13 Hz, 2H) 0.80 (dd, J=9 Hz, 7 Hz, 2H), 0.63 (dd, J=9 Hz, 7 Hz, 2H). MS[M+H]$^+$: 224.

Intermediate A2

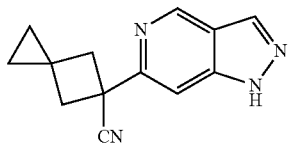 [SMILES: N#CC1(c2cc3[nH]ncc3cn2)CC2(CC2)C1]

5-(1H-pyrazolo[4,3-c]pyridin-6-yl)spiro[2.3]hexane-5-carbonitrile

To a vessel was added 6-chloro-1H-pyrazolo[4,3-c]pyridine (100 mg, 0.651 mmol), Josiphos Pd G3 (60.2 mg, 0.065 mmol) and the reaction was purged with argon. THF (2171 µl) added and the solution was further degassed with argon. Spiro[2.3]hexane-5-carbonitrile (174 mg, 1.628 mmol) was added followed by 1.0M LiHMDS (1628 µl, 1.628 mmol) in THF dropwise. The reaction was then heated to 80° C. overnight. The reaction was purified directly by silica gel chromatography, eluting with ethyl acetate/hexanes to give the title compound. $^1$H NMR (600 MHz, CDCl$_3$) δ 9.16 (s, 1H), 8.21 (s, 1H), 7.71 (s, 1H), 3.18 (d, J=12.4 Hz, 2H), 2.79 (d, J=12.4 Hz, 2H), 0.79-0.72 (m, 2H), 0.59-0.53 (m, 2H). MS[M+H]$^+$: 225.

SCHEME A1

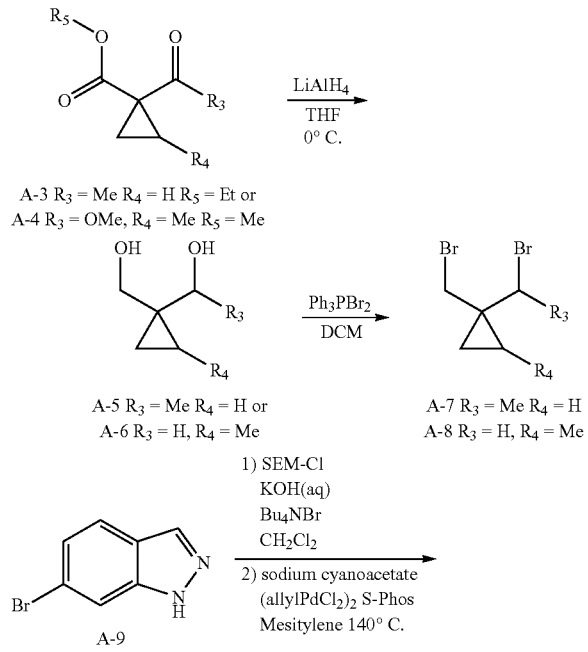

A-3 R$_3$ = Me R$_4$ = H R$_5$ = Et or
A-4 R$_3$ = OMe, R$_4$ = Me R$_5$ = Me

A-5 R$_3$ = Me R$_4$ = H or
A-6 R$_3$ = H, R$_4$ = Me

A-7 R$_3$ = Me R$_4$ = H
A-8 R$_3$ = H, R$_4$ = Me

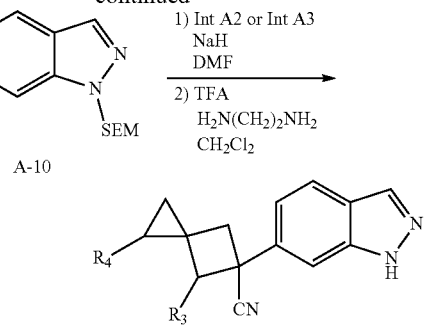

1) Int A2 or Int A3
   NaH
   DMF
2) TFA
   H$_2$N(CH$_2$)$_2$NH$_2$
   CH$_2$Cl$_2$ intermediate A3 R$_3$ = Me R$_4$ = H
intermediate A4 R$_3$ = H R$_4$ = Me Intermediate A3

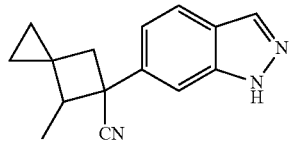 [SMILES: CC1C2(CC2)CC1(C#N)c1ccc2cn[nH]c2c1]

5-(1H-indazol-6-yl)-4-methylspiro[2.3]hexane-5-carbonitrile

Step 1: 1-(1-(hydroxymethyl)cyclopropyl)ethan-1-ol

Ethyl 1-acetylcyclopropanecarboxylate (0.781 g, 5.0 mmol) was dissolved in THF (12.50 ml) and cooled to 0° C. 1.0M lithium aluminum hydride (12.50 ml, 12.50 mmol) in THF was added, then after 5-10 minutes the cooling bath was removed and the reaction was stirred at room temperature. After 4 hours the reaction was worked up by adding about 3 mL of 5 M NaOH, followed by EtOAc and MgSO$_4$. The mixture was filtered and evaporated to give crude target, which was used without further purification. $^1$H NMR (500 MHz, CDCl$_3$) δ 4.06 (dd, J=11.5, 0.5 Hz, 1H), 3.46 (q, J=13, 6.5 Hz, 1H), 3.21 (d, J=13 Hz, 1H), 1.30 (d, J=6.5 Hz, 3H), 0.62 (m, 2H), 0.42 (m, 2H).

Step 2: 1-(1-bromoethyl)-1-(bromomethyl)cyclopropane 1-(1-(hydroxymethyl)cyclopropyl)ethanol (581 mg, 5 mmol) was dissolved in anhydrous CH$_2$Cl$_2$ (22 mL) and cooled to 0° C. Triphenylphosphine dibromide (5.28 g, 12.50 mmol) was added and the mixture slowly stirred overnight under nitrogen atmosphere until room temperature was reached. Much of the of CH$_2$Cl$_2$ (to ~3-5 mL) was evaporated then the mixture was diluted with hexanes, then filtered. The filtrate was subjected again to evaporation in ~4 mL hexane, and purified on a silica gel column, eluting with EtOAc/hexanes. Product fractions were evaporated by rotary evaporation to give the title compound. $^1$H NMR (500 MHz, CDCl$_3$) δ 4.47 (q, J=14, 7 Hz, 1H), 3.87 (dd, J=10.8, 1 Hz, 1H), 3.36 (d, J=10.5 Hz, 1H), 1.65 (d, J=7 Hz, 3H), 1.07 (m, 2H), 0.91 (m, 2H).

Step 3: 6-bromo-1-((2-(trimethylsilyl)ethoxy) methyl)-1H-indazole 6-bromo-1H-indazole (4.93 g, 25 mmol) was suspended/partially dissolved in anhydrous DCM (100 ml). Then 5N aqueous KOH (6.00 ml, 30.0 mmol) was added, followed by SEM-Cl (5.32 ml, 30.0 mmol) and tetrabutylammonium bromide (0.806 g, 2.500 mmol). Continued stirring overnight. Diluted with water and partitioned. Washed organic twice more with water, dried over sodium sulfate, filtered and evaporated. Added DCM to the crude and filtered to recover a white solid and a slightly yellow filtrate. Evaporated the filtrate down to half volume and filtered again, then purified the filtrate as is by silica gel chromatography, eluting with EtOAc/hexanes to give both regioisomers separately. The desired regioisomer eluted before the undesired. $^1$H NMR (500 MHz, CDCl$_3$): δ 7.99 s, 1H), 7.79 (s, 1H), 7.61 (d, J=8.5 Hz, 1H), 7.31 (dd, J=8.5, 1.5 Hz, 1H), 5.71 (s, 2H), 3.54 (m, 2H), 0.90 (m, 2H), 0.04 (s, 9H). MS[M+H]$^+$: 327, 329.

Step 4: 2-(1-((2-(trimethylsilyl)ethoxy)methyl)-1H-indazol-6-yl)acetonitrile Sodium 2-cyanoacetate (602 mg, 5.63 mmol), allylpalladium(II) chloride dimer (27.4 mg, 0.075 mmol) and dicyclohexyl((2-[(2,6-dimethoxyphenyl)methyl)phenyl]methyl)phosphane (99 mg, 0.225 mmol) were added to a 250 ml rb flask, which was evacuated and charged with nitrogen. Then 6-bromo-1-((2-(trimethylsilyl)ethoxy)methyl)-1H-indazole (1.23 g, 3.75 mmol) was dissolved/suspended in 9.4 mL mesitylene and added to the catalyst/ligand/salt mixture. The vessel was fitted with a reflux condenser, then evacuated and charged again with nitrogen, stirred for 10 minutes at room temperature, then heated to 140° C. and monitored by LCMS. When the starting indazole was consumed, the reaction was filtered over Celite® (diatamacious earth), then the filtrate was purified directly by silica gel column, eluting with EtOAc/hexanes. The fractions were isolated and purified as mixed fractions. The mixed fractions were evaporated and repurified as described above. The combined purified fractions were evaporated to give the target compound.

MS[M+H]$^+$: 288.

Step 5: 4-methyl-5-(1-((2-(trimethylsilyl)ethoxy)methyl)-1H-indazol-6-yl)spiro[2.3]hexane-5-carbonitrile To a round bottom flask containing sodium hydride (147 mg, 3.68 mmol) in 3.5 mL DMF at 0° C. under nitrogen atmosphere was added a solution of 2-(1-((2-(trimethylsilyl)ethoxy)methyl)-1H-indazol-6-yl)acetonitrile (423 mg, 1.47 mmol) and 1-(1-bromoethyl)-1-(bromomethyl)cyclopropane ((product from Step 2, 356 mg, 1.470 mmol) in 4.0 mL of DMF dropwise. The stirring mixture was allowed to slowly reach room temperature. The reaction was deemed completed at 150 minutes on LCMS. The reaction was quenched with aq NH$_4$Cl, then diluted with water and ethyl acetate, partitioned, then washed once with organic solution water and then once with brine. The product was then dried over sodium sulfate, filtered and evaporated, then purified by silica gel column, eluting with EtOAc/hexanes. The major peak was isolated. MS[M+H]$^+$: 368

Step 6: 5-(1H-indazol-6-yl)-4-methylspiro[2.3]hexane-5-carbonitrile 4-methyl-5-(1-((2-(trimethylsilyl)ethoxy)methyl)-1H-indazol-6-yl)spiro[2.3]hexane-5-carbonitrile (294 mg, 0.800 mmol) was dissolved in DCM (4.5 mL) and TFA (2.0 mL, 26.0 mmol), then stirred for 2.5 hours. The reaction was then concentrated, redissolved in DCM (4.5 mL), and then ethylenediamine (3.0 mL, 44.4 mmol) was added. After an hour, the reaction was quenched with water and extracted twice with EtOAc. The organic layer was then washed again with water, dried over sodium sulfate, filtered and evaporated, then pumped on vacuum overnight, then purified by silica gel chromatography, eluting with EtOAc/hexanes to give the target compound. MS[M+H]$^+$: 238

Intermediate A4

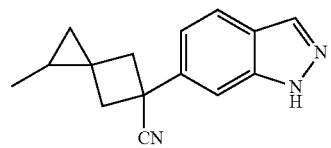 [SMILES: CC1CC12CC(C#N)(c1ccc3cn[nH]c3c1)C2]

5-(1H-indazol-6-yl)-1-methylspiro[2.3]hexane-5-carbonitrile

Starting with dimethyl 2-methylcyclopropane-1,1-dicarboxylate (see A-4, Scheme A1) and repeating the above 6 step sequence provided 5-(1H-indazol-6-yl)-1-methylspiro[2.3]hexane-5-carbonitrile. MS[M+H]$^+$: 238.

SCHEME B

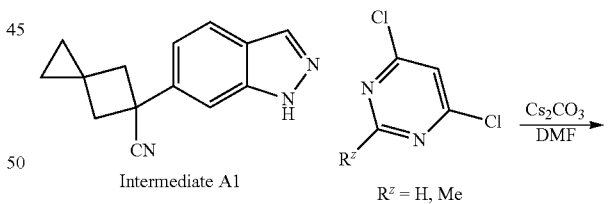

Intermediate A1

R$^z$ = H, Me

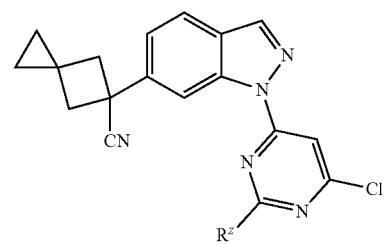

Intermediate B

R$^z$ = H, Me

Intermediate B1 was prepared as shown in Scheme B above. Intermediate A1 was combined with a dichloropyrimidine in the presence of base and an organic solvent such as DMF or DMA. These intermediates can be isolated as shown below, or isolated using alternative methods, or used directly in the next step without purification or workup.

Intermediate B1

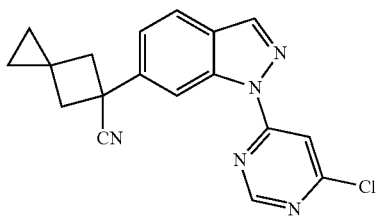 [SMILES: N#CC1(c2ccc3cnn(-c4cc(Cl)ncn4)c3c2)CC2(CC2)C1]

5-(1-(6-chloropyrimidin-4-yl)-1H-indazol-6-yl)spiro[2.3]hexane-5-carbonitrile (Scheme B)

5-(1H-indazol-6-yl)spiro[2.3]hexane-5-carbonitrile (INTERMEDIATE A1, 335 mg, 1.5 mmol) and 4,6-dichloropyrimidine (335 mg, 2.250 mmol) were dissolved in DMF (2.5 ml). Cs$_2$CO$_3$ (733 mg, 2.250 mmol) was added. The mixture stirred overnight at room temperature. The reaction was diluted with water and filtered. The solid was taken up in EtOAc and combined with the aqueous filtrate, then partitioned. The organic was dried over Na$_2$SO$_4$, filtered and evaporated. The organic layer was cloudy with a fine particulate solid, much of which passed through the filter. The crude was taken up in DCM and purified by silica gel chromatography, eluting with iPrOAc/hexanes. The higher rf spot was cleanly eluted in the early fractions, with later fractions mixed with a more fluorescent spot. The mixed fractions were evaporated and purified again with iPrOAc/hexanes. The clean fractions were combined with the earlier clean material, and the mixed material was evaporated down and recycled through another purification. The process was repeated twice more to give the target compound as a solid. $^1$H NMR (500 MHz, CDCl$_3$): δ 9.12 (s, 1H), 8.93 (s, 1H), 8.29 (s, 1H), 8.08 (s, 1H) 7.84 (d, J=8.5 Hz, 1H), 7.57 (d, J=8.5, 1H), 3.13 (d, J=12.5 Hz, 2H), 2.88 (d, J=12.5 Hz, 2H) 0.82 (dd, J=9 Hz, 7.5 Hz, 2H), 0.68 (dd, J=9 Hz, 7 Hz, 2H). MS[M+H]$^+$: 336.

The intermediate B2 in table B was prepared according to scheme B using the procedures outlined in the synthesis of intermediate B1, substituting 2-methyl-4,6-dichloropyrimidine for 4,6-dichloropyrimidine.

SCHEME C

Cyclic amines (and/or their salts) were prepared via an acid deprotection step or hydrogenolysis of the Boc or Cbz protected cyclic amine R$^2$ (as defined in Formula (I)) respectively. These cyclic amines may be commercially available or prepared as described in the procedures below.

Intermediate C1

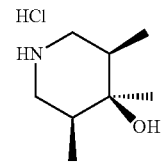

(3S,4s,5R and 3R,4s,5S)-3,4,5-trimethylpiperidin-4-ol hydrochloride* (Scheme C)

Step 1: tert-butyl (3S,5R) and (3R,5S)-3,5-dimethyl-4-oxopiperidine-1-carboxylate Into a 5000-mL 4-necked round-bottom flask, was placed (3S,5R) and (3R,5S)-1-benzyl-3,5-dimethylpiperidin-4-one* (250 g, 1.15 mol, 1.00 equiv), Pd(OH)$_2$/C (50 g), methanol (2.5 L), Boc$_2$O (552.3 g, 2.53 mol, 2.20 equiv). Hydrogen was introduced. The resulting solution was stirred overnight at room temperature. The solids were filtered out. The resulting mixture was concentrated under vacuum. The resulting mixture was washed with heptane to give the title compound.

Step 2: tert-butyl (3S,4s,5R and 3R,4s,5S)-4-hydroxy-3,4,5-trimethylpiperidine-1-carboxylate*

To a stirred solution of tert-butyl (3S,5R) and (3R,5S)-3,5-dimethyl-4-oxopiperidine-1-carboxylate* (30.8 g, 135.6 mmol) in THF (500 mL) at 0° C. was slowly added methyl magnesium bromide (120 mL, 360 mmol). The mixture was warmed to room temperature and stirred overnight. The reaction was quenched with a saturated NH$_4$Cl solution,

TABLE B

| Intermediate | Structure | Name | MS [M + H]$^+$ |
|---|---|---|---|
| B2 | ![structure] | 5-(1-(6-chloro-2-methylpyrimidin-4-yl)-1H-indazol-6-yl)spiro[2.3]hexane-5-carbonitrile | 350 | extracted with EtOAc (400 mL×3). The combined organic layers were concentrated to give the title compound as a solid. $^1$H NMR: (CDCl$_3$, 300 MHz) δ 3.76 (s, 2H), 2.70 (s, 2H), 1.58-1.50 (m, 2H), 1.50 (s, 9H), 1.18 (s, 2H), 1.09 (s, 1H), 0.92-0.90 (d, 6H).

Step 3: (3S,4s,5R and 3R,4s,5S)-3,4,5-trimethylpiperidin-4-ol hydrochloride*

To a solution of tert-butyl (3S,4s,5R and 3R,4s,5S)-4-hydroxy-3,4,5-trimethylpiperidine-1-carboxylate* (33 g, 230.7 mmol) in MeOH (100 mL) was added HCl/MeOH (400 mL). The mixture was stirred at room temperature for 5 hours and then concentrated to give the title compound as a solid. $^1$H NMR (DMSO-d6 400 MHz): δ 9.21-9.09 (d, 2H), 4.48 (s, 1H), 2.85-2.82 (d, 2H), 2.70-2.62 (m, 2H), 1.80-1.74 (m, 2H), 1.07 (m, 3H), 0.85-0.83 (d, 6H).

MS[M+H]$^+$: 144.

*relative configuration

Intermediate C2

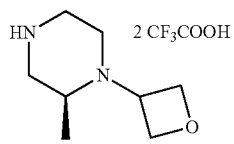

(S)-2-methyl-1-(oxetan-3-yl)piperazine bis TFA salt

Step 1: (S)-tert-butyl 3-methyl-4-(oxetan-3-yl)piperazine-1-carboxylate (S)-tert-butyl 3-methylpiperazine-1-carboxylate (1.001 g, 5.0 mmol) and oxetan-3-one (0.721 g, 10.00 mmol) were dissolved in 1,2-dichloroethane (20.00 ml). 4 A Molecular Sieves (1.5 g, powdered and dried) were added, and the mixture stirred for 60 minutes. Sodium triacetoxyborohydride (2.013 g, 9.50 mmol) was then added portionwise over approximately 10 minutes. The reaction was allowed to stir from 24-72 hours, then partitioned between aq. NaHCO$_3$ and CH$_2$Cl$_2$. The organic layer was dried over sodium sulfate, filtered and evaporated, then purified by silica gel chromatography, eluting with 3:1 EtOAc:EtOH in hexanes. The product was detected by TLC of fractions with ninhydrin staining. The major spot was collected and evaporated to give the title compound. MS[M+H]$^+$: 257.

(S)-2-methyl-1-(oxetan-3-yl)piperazine bis TFA salt (S)-tert-butyl 3-methyl-4-(oxetan-3-yl)piperazine-1-carboxylate (0.256 g, 1 mmol) was dissolved in CH$_2$Cl$_2$ (4.00 ml). TFA (0.770 ml, 10.00 mmol) was added, and the mixture was stirred, with monitoring by LCMS. At 2 hours the reaction was complete; volatiles were evaporated. The assumed product was the bis TFA salt plus residual TFA. MS[M+H]$^+$: 157.

Intermediate C3

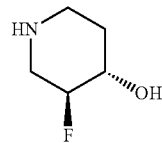

(3S,4S)-3-fluoropiperidin-4-ol (3S,4S)-benzyl 3-fluoro-4-hydroxypiperidine-1-carboxylate (150 mg, 0.592 mmol) was dissolved in MeOH (6 mL). The mixture was evacuated and charged 3× with nitrogen, then 10% Pd—C(47.3 mg, 0.044 mmol) was added, then evacuated and charged 3× with hydrogen and stirred overnight. The reaction was filtered over Celite®, the filter bed washed with MeOH, and the filtrate was evaporated to give the target compound. $^1$H NMR (500 MHz, CDCl$_3$): δ 4.34 (m, 0.5H), 4.23 (m, 0.5H), 3.76 (m, 1H), 3.32 (m, 1H), 3.02 (m, 1H), 2.62 (m, 2H), 2.04 (m, 1H), 1.51 (m, 1H).

Intermediate C4

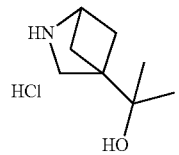

2-(2-azabicyclo[2.1.1]hexan-4-yl)propan-2-ol, HCl salt

Step 1: 2-tert-butyl 4-methyl 2-azabicyclo[2.1.1]hexane-2,4-dicarboxylate (Trimethylsilyl)diazomethane (2.340 mL, 4.68 mmol) was added to a solution of 2-(tert-butoxycarbonyl)-2-azabicyclo[2.1.1]hexane-4-carboxylic acid (0.532 g, 2.34 mmol) in MeOH (5 mL) at room temperature. The reaction was stirred for 1 hour. Additional (trimethylsilyl) diazomethane (2.340 mL, 4.68 mmol) was added until a yellow color persisted, and the solution was stirred overnight. The reaction was quenched with a few drops of acetic acid and a solution of citric acid (2M, 10 mL) was added to give a pH of 2. The mixture was diluted with EtOAc (250 mL), layers were separated, and the organic layer was washed with aqueous sodium hydrogen carbonate (saturated, 2×250 mL) followed by brine (1×250 mL). The organic was dried (Na$_2$SO$_4$), filtered, and the solvent was evaporated under reduced pressure to provide the title compound, which was carried on crude.

Step 2: tert-butyl 4-(2-hydroxypropan-2-yl)-2-azabicyclo[2.1.1]hexane-2-carboxylate 2-Tert-butyl 4-methyl 2-azabicyclo[2.1.1]hexane-2,4-dicarboxylate (4.16 g, 17.24 mmol) was dissolved in THF (69.0 ml) and cooled to 0° C. under nitrogen. After 10 minutes approximately 3.4 M methylmagnesium bromide (13 ml, 44.2 mmol) was added in 2-methyl THF. The mixture was stirred for 1 hour then removed from the bath. Subsequently the mixture was again stirred for 24 hours, then the reaction was quenched with aq. NH₄Cl, then extracted with EtOAc. The organic layer was then washed with water followed by brine, then dried over sodium sulfate, filtered and evaporated. The crude was then pumped under vacuum overnight, then subsequently purified by silica gel chromatography, eluting with EtOAc/hexanes and checking fractions by TLC with ninhydrin dip/heat. The product containing fractions was evaporated to give the title compound. ¹H NMR (500 MHz, CDCl₃): δ 4.34 (br, 2H), 3.26 (s, 2H), 1.83 (d, J=4.5 Hz, 2H), 1.48 (s, 9H), 1.45 (d, J=4.5 Hz, 2H), 1.26 (s, 6H).

Step 3: 2-(2-azabicyclo[2.1.1]hexan-4-yl)propan-2-ol, HCl salt tert-butyl 4-(2-hydroxypropan-2-yl)-2-azabicyclo[2.1.1] hexane-2-carboxylate (3.00 g, 12.43 mmol) was dissolved in dioxane (22 ml) followed by 4N HCl (11 ml, 44.0 mmol) in dioxane and stirred. The reaction was monitored by TLC. At 1 hour, with the reaction partially completed, another 11 mL of 4N HCl in dioxane was added with continued stirring. TLC showed the total reaction completed at 4 hours with complete consumption of starting material and a baseline product (Hex/EtOAc). Subsequent evaporation by rotary evaporation gave the title compound. ¹H NMR (500 MHz, CD₃OD): δ 4.14 (s, 1H), 3.27 (s, 2H), 2.08 (m, 2H) 1.58 (m, 2H), 1.25 (s, 6H).

Intermediate C5

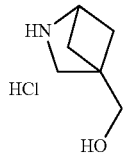

(2-azabicyclo[2.1.1]hexan-4-yl)methanol hydrochloride

Step 1: tert-butyl 4-(hydroxymethyl)-2-azabicyclo[2.1.1]hexane-2-carboxylate 2-tert-butyl 4-methyl 2-azabicyclo[2.1.1]hexane-2,4-dicarboxylate (see Intermediate C4, step 1, 800 mg, 3.32 mmol) was dissolved in THF (5 ml), followed by addition of lithium borohydride (2M) in THF (5.30 ml, 10.61 mmol). The mixture was stirred at room temperature overnight. The reaction was then quenched with water and diluted with ethyl acetate. The organic layer was separated and dried with MgSO₄, filtered, and concentrated to give the title compound. ¹H NMR (500 MHz, CDCl₃): δ 4.34 (br, 2H), 3.83 (s, 2H), 3.25 (s, 2H), 1.92-1.73 (m, 3H), 1.49 (s, 9H).

Step 2: (2-azabicyclo[2.1.1]hexan-4-yl)methanol hydrochloride tert-butyl 4-(hydroxymethyl)-2-azabicyclo[2.1.1]hexane-2-carboxylate (150 mg, 0.703 mmol) was dissolved in dioxane (1.4 mL) followed by 4 N HCl (0.879 mL, 3.52 mmol) in dioxane and stirred overnight at room temperature, then evaporated by rotary evaporation to give the title compound. ¹H NMR (500 MHz, CD₃OD): δ 4.19 (s, 1H), 3.80 (s, 2H), 3.36 (s, 1H), 3.24 (s, 2H), 2.05 (m, 2H), 1.58 (m, 2H).

Intermediate C6

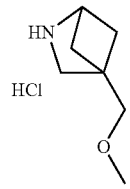

4-(methoxymethyl)-2-azabicyclo[2.1.1]hexane hydrochloride

Step 1: tert-butyl 4-(methoxymethyl)-2-azabicyclo[2.1.1]hexane-2-carboxylate tert-butyl 4-(hydroxymethyl)-2-azabicyclo[2.1.1]hexane-2-carboxylate (see Intermediate C5, step 1, 213 mg, 1.0 mmol) was dissolved in THF (5000 μl) and cooled to 0° C. Sodium hydride (44.0 mg, 1.100 mmol) was added and the mixture was stirred for 20 minutes. Then iodomethane (313 μl, 5.00 mmol) was added and the mixture stirred overnight. The reaction was then quenched with aq. NH₄Cl, and partitioned between water and ethyl acetate. The organic layer was washed again with water, then dried over sodium sulfate, filtered and evaporated, then purified by silica gel chromatography, eluting with EtOAc/hexanes. Fractions were visualized by TLC with ninhydrin stain. The requisite fractions were evaporated to give the title compound. ¹H NMR (500 MHz, CDCl₃): δ 4.34 (br, 1H), 3.57 (s, 2H), 3.38 (s, 3H), 3.25 (s, 2H), 1.81 (s, 2H), 1.58 (s, 2H), 1.48 (s, 9H).

Step 2: 4-(methoxymethyl)-2-azabicyclo[2.1.1] hexane hydrochloride tert-butyl 4-(methoxymethyl)-2-azabicyclo[2.1.1]hexane-2-carboxylate (52 mg, 0.229 mmol) was dissolved in dioxane (0.5 mL) followed by 4 N HCl (0.286 mL, 1.144 mmol) in dioxane and stirred overnight at room temperature. The solvent was evaporated by rotary evaporation to give the title compound. ¹H NMR (500 MHz, CD₃OD): δ 4.19 (s, 1H), 3.64 (s, 2H), 3.38 (s, 3H), 3.36 (s, 1H), 3.24 (s, 2H), 2.07 (m, 2H), 1.58 (m, 2H).

Intermediate C7

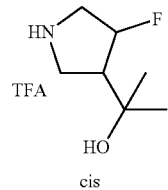

cis

Cis-2-(4-fluoropyrrolidin-3-yl)propan-2-ol, TFA salt

Step 1: Cis-tert-butyl-3-fluoro-4-(2hydroxypropan-2-yl)pyrrolidine-1-carboxylate To a solution of cis-1-tert-butyl 3-methyl 4-fluoropyrrolidine-1,3-dicarboxylate (500 mg, 2.022 mmol) in THF (15 ml), cooled in an ice bath, was added methylmagnesium bromide (3.37 ml, 10.11 mmol) dropwise over approximately 20 minutes. The mixture was brought to room temperature and stirred for 3 hrs. The reaction was monitored by TLC until completion. The mixture was quenched with saturated NH$_4$Cl solution (dropwise at first) (15 ml). The organic phase was separated and the aqueous phase extracted with EtOAc (2×10 mL). The organic extracts were combined, washed with water (10 mL) and brine (10 ml), dried over MgSO$_4$ and then concentrated to dryness to obtain the target compound. The product was used as is without characterization.

Step 2: Cis-2-(4-fluoropyrrolidin-3-yl)propan-2-ol, TFA salt

To a solution of tert-butyl 3-fluoro-4-(2-hydroxypropan-2-yl)pyrrolidine-1-carboxylate (100 mg, 0.404 mmol) in CH$_2$Cl$_2$ (2 ml) was added TFA (0.2 mL). The mixture was stirred at room temperature for 2-3 hours. The reaction was monitored by LCMS. As soon as the starting material is consumed the reaction mixture was dried under N$_2$ stream and used immediately for the next step. MS[M+H]$^+$: 148.

Intermediate C9

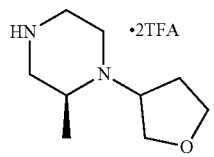

(2S)-2-methyl-1-(tetrahydrofuran-3-yl)piperazine bis TFA salt

Step 1: tert-butyl (3S)-3-methyl-4-(tetrahydrofuran-3-yl)piperazine-1-carboxylate (S)-Tert-butyl 3-methylpiperazine-1-carboxylate (601 mg, 3 mmol) and dihydrofuran-3(2H)-one (501 mg, 5.82 mmol) were dissolved in DCE (12 mL). 4 A Molecular Sieves (1000 mg, powdered and dried) were added and the mixture was stirred for 60 minutes. Sodium triacetoxyborohydride (1208 mg, 5.70 mmol) was then added portionwise over 10 minutes. The reaction was allowed to stir overnight. The reaction was filtered and the solid was washed with DCM, partitioned between aq. NaHCO$_3$ and DCM, then the separated organic fraction was dried over sodium sulfate, filtered and evaporated. The residue was purified by silica gel chromatography, eluting with a gradient of 3:1 EtOAc:EtOH in hexanes, and dried in vacuo overnight to give target product. MS[+H]$^+$: 271.

Step 2: (2S)-2-methyl-1-(tetrahydrofuran-3-yl)piperazine bis TFA salt (3S)-tert-butyl 3-methyl-4-(tetrahydrofuran-3-yl)piperazine-1-carboxylate (150 mg, 0.555 mmol) was dissolved in DCM (2.2 mL). TFA (0.427 mL, 5.55 mmol) was added followed by stirring while monitoring by LCMS. At 2 hours the reaction was complete. The volatiles were evaporated to give target product. MS[+H]$^+$: 171.

Intermediate C10

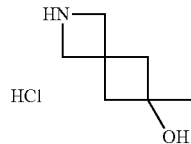

6-methyl-2-azaspiro[3.3]heptan-6-ol hydrochloride

Step 1: tert-butyl 6-hydroxy-6-methyl-2-azaspiro [3.3]heptane-2-carboxylate

Tert-butyl 6-oxo-2-azaspiro[3.3]heptane-2-carboxylate (0.500 g, 2.367 mmol) was dissolved in THF (12 ml) and cooled to 0° C. under nitrogen. After 10 minutes 3.0 M methylmagnesium chloride (1.2 ml, 3.60 mmol) in THF was added. The mixture was stirred for 20 minutes then removed from the bath and stirred overnight. The reaction was quenched with aq. NH$_4$Cl and extracted with ethyl acetate twice. The organics were then washed with water and brine, dried over sodium sulfate, filtered and evaporated. The crude was purified by silica gel chromatography, eluting with a EtOAc in hexanes gradient to provide the target product after rotary evaporation of the target containing fractions. $^1$H NMR (500 MHz, CDCl$_3$): δ 3.92 (d, J=14 Hz, 4H), 2.27 (t, J=13.5 Hz, 4H), 1.44 (s, 9H), 1.33 (s, 3H).

Step 2: 6-methyl-2-azaspiro[3.3]heptan-6-ol hydrochloride tert-butyl 6-hydroxy-6-methyl-2-azaspiro[3.3]heptane-2-carboxylate (0.338 g, 1.487 mmol) was dissolved in 1,4-Dioxane (3 ml). Then added 4.0 M HCl (3.72 ml, 14.87 mmol) in dioxane. Stirred for 20 minutes then checked by TLC (ninhydrin staining). Reaction complete in ~2 hours. Evaporated solvent/HCl and pumped isolate on vacuum to give the target product. $^1$H NMR (500 MHz, CDCl$_3$): δ 3.67 (s, 4H), 2.33 (q, J=28.5, 14 Hz, 2H), 2.08 (m, 2H), 1.33 (d, J=54 Hz, 3H).

Intermediate C11

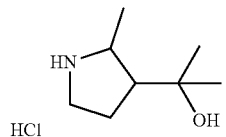

2-(2-methylpyrrolidin-3-yl)propan-2-ol hydrochloride

Step 1: tert-butyl 3-(2-hydroxypropan-2-yl)-2-methylpyrrolidine-1-carboxylate 1-tert-butyl 3-methyl 2-methylpyrrolidine-1,3-dicarboxylate (0.500 g, 2.055 mmol) was dissolved in THF (8.22 ml)

and cooled to 0° C. under nitrogen. After 10 minutes added 3.0 M methylmagnesium chloride (1.667 ml, 5 mmol) in THF was added. The mixture was stirred for 1 hour then bath was removed.

After stirring for 24 hours the reaction was quenched with aq. NH$_4$Cl, extracted with EtOAc, then washed the organic with water followed by brine. The organic layer was dried over sodium sulfate, filtered, evaporated, purified by silica gel chromatography, eluting with EtOAc/hexanes and checking fractions by TLC with ninhydrin dip/heat. Rotary evaporation of the requisite fractions provided the target product. MS[M+H]$^+$: 244.

Step 2: 2-(2-methylpyrrolidin-3-yl)propan-2-ol hydrochloride

Tert-butyl 3-(2-hydroxypropan-2-yl)-2-methylpyrrolidine-1-carboxylate (214 mg, 0.879 mmol) was dissolved in dioxane (1.8 mL) followed by 4N HCl (0.750 mL, 3.00 mmol) in dioxane and stirred. TLC at 4 hours total reaction time showed complete consumption of starting material and a baseline product (7/3 Hex/EtOAc), evaporated the mixture by rotary evaporation to give a yellow oil. The product was used as is without further purification. MS[M+H]$^+$: 144.

Scheme D

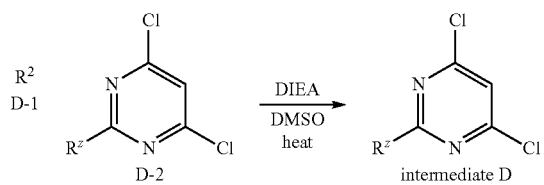

Intermediate D was prepared according to Scheme D by S$_N$Ar reaction of pyrrolidine D-1 and dichloropyrimidine D-2, wherein R$^z$ and R$^2$ in Scheme D is as defined in Formula (I).

Intermediate D1

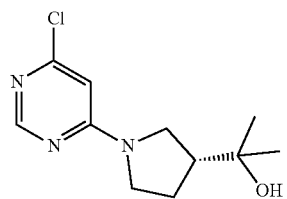 [SMILES: CC(C)(O)[C@@H]1CCN(c2cc(Cl)ncn2)C1]

(R)-2-(1-(6-chloropyrimidin-4-yl)pyrrolidin-3-yl) propan-2-ol (Scheme D)

Step 1: (R)-2-(1-(6-chloropyrimidin-4-yl)pyrrolidin-3-yl)propan-2-ol 4,6-dichloropyrimidine (1.490 g, 10 mmol) was suspended in DMSO (15 ml). (R)-2-(pyrrolidin-3-yl)propan-2-ol hydrochloride (1.822 g, 11.00 mmol) and DIEA (4.37 ml, 25.00 mmol) were added, then the mixture was heated to 90° C. overnight. LCMS after 18 hours showed the reaction complete. The product was then cooled to room temperature, and ethyl acetate was added, filtered, then the filtrate was washed 3× with water, dried over sodium sulfate, filtered again, and evaporated. The product was purified by silica gel chromatography. Eluting with 3:1 EtOAc:EtOH in hexanes gave the title compound. $^1$H NMR (500 MHz, CDCl$_3$): δ 8.37 (s, 1H), 6.30 (s, 1H), 3.90 (br, 1H), 3.73 (m, 1H), 3.39 (m, 3H), 2.39 (br, 1H), 2.05 (br, 2H) 1.40 (s, 6H). MS[M+H]$^+$: 242.

The intermediates in table D were prepared according to scheme D using the procedures outlined in the synthesis of intermediate D1. The pyrimidines and amines utilized in this scheme are either commercially available or their synthesis has been described elsewhere in this document.

TABLE D

| Intermediate | Structure | Name | MS [M + H]$^+$ |
|---|---|---|---|
| D2 | 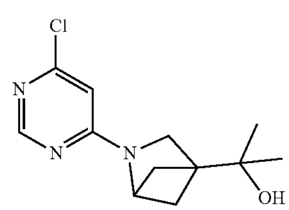 [SMILES: CC(C)(O)C12CC(C1)N(c1cc(Cl)ncn1)C2] | 2-(2-(6-chloropyrimidin-4-yl)-2-azabicyclo[2.1.1]hexan-4-yl)propan-2-ol | 254 |
| D3 | 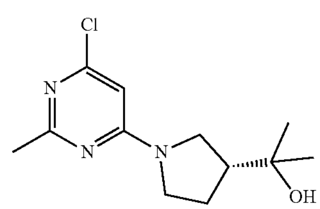 [SMILES: Cc1nc(Cl)cc(N2CC[C@@H](C(C)(C)O)C2)n1] | (R)-2-(1-(6-chloro-2-methylpyrimidin-4-yl)pyrrolidin-3-yl)propan-2-ol | 256 |

TABLE D-continued

| Intermediate | Structure | Name | MS [M + H]+ |
|---|---|---|---|
| D4 | 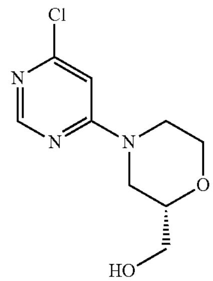 [SMILES: OC[C@@H]1CN(c2cc(Cl)ncn2)CCO1] | (S)-(4-(6-chloropyrimidin-4-yl)morpholin-2-yl)methanol | 230 |
| D5 | 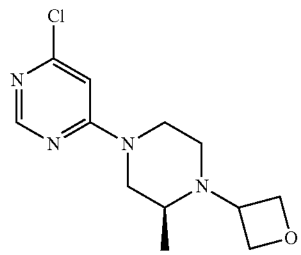 [SMILES: C[C@H]1CN(c2cc(Cl)ncn2)CCN1C1COC1] | (S)-4-chloro-6-(3-methyl-4-(oxetan-3-yl)piperazin-1-yl)pyrimidine | NMR* |
| D6 | 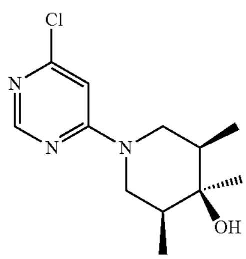 [SMILES: C[C@@H]1CN(c2cc(Cl)ncn2)C[C@H](C)[C@]1(C)O] | (3S,4s,5R and 3R,4s,5S)-1-(6-chloropyrimidin-4-yl)-3,4,5-trimethylpiperidin-4-ol | 256 |
| D7 | 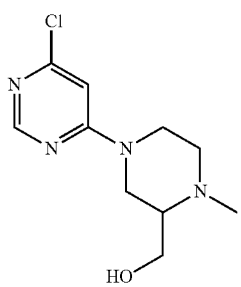 [SMILES: CN1CCN(c2cc(Cl)ncn2)CC1CO] | (4-(6-chloropyrimidin-4-yl)-1-methylpiperazin-2-yl)methanol | 243 |
| D8 | 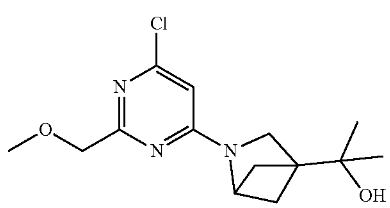 [SMILES: COCc1nc(Cl)cc(N2CC3(C(C)(C)O)CC2C3)n1] | 2-(2-(6-chloro-2-(methoxymethyl)pyrimidin-4-yl)-2-azabicyclo[2.1.1]hexan-4-yl)propan-2-ol | 298 |
| D9 | 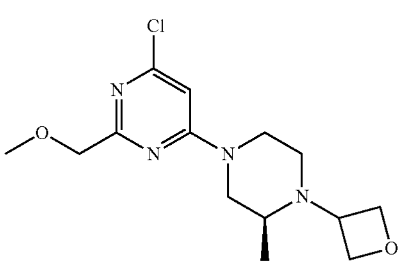 [SMILES: COCc1nc(Cl)cc(N2CCN(C3COC3)[C@@H](C)C2)n1] | (S)-4-chloro-2-(methoxymethyl)-6-(3-methyl-4-(oxetan-3-yl)piperazin-1-yl)pyrimidine | 313 |

TABLE D-continued

| Intermediate | Name | MS [M + H]+ |
|---|---|---|
| D10 | 2-(2-(6-chloro-2-(methylthio)pyrimidin-4-yl)-2-azabicyclo[2.1.1]hexan-4-yl)propan-2-ol | 300 |
| D11 | 2-(1-(6-chloropyrimidin-4-yl)azetidin-3-yl)propan-2-ol | 228 |
| D12 | 1-(6-chloropyrimidin-4-yl)-3-methylazetidin-3-ol | 200 |
| D13 | 4-chloro-6-(3-methoxy-3-methylazetidin-1-yl)pyrimidine | 214 |
| D14 | 1-(6-chloropyrimidin-4-yl)-3-cyclopropylazetidin-3-ol | 226 |
| D15 | 2-(6-chloropyrimidin-4-yl)-8-methyl-5-oxa-2,8-diazaspiro[3.5]nonane | 255 |

*$^1$H-NMR (CDCl3, 500 MHz) δ 8.38 (s, 1H), 6.50 (s, 1H), 4.74-4.60 (m, 4H), 3.94 (br, 2H), 3.76 (m, 2H), 3.40 (t, J = 9.8 Hz, 1H), 3.10 (m, 1H), 2.71 (m, 1H), 2.43 (m, 1H), 2.17 (m, 1H), 1.26 (m, 2H), 0.96 (d, J = 6.5 Hz, 3H).

Intermediates D16 and D17

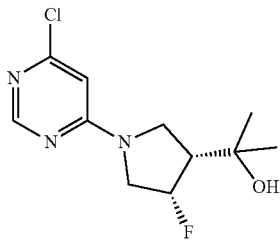

2-((3R,4S or 3S,4R)-1-(6-chloropyrimidin-4-yl)-4-fluoropyrrolidin-3-yl)propan-2-ol (Cis Isomer 1) and 2-((3S,4R or 3R,4S)-1-(6-chloropyrimidin-4-yl)-4-fluoropyrrolidin-3-yl)propan-2-ol (Cis Isomer 2)

To a suspension of 4,6-dichloropyrimidine (0.570 g, 3.83 mmol) and cis-2-(4-fluoropyrrolidin-3-yl)propan-2-ol TFA salt (1 g, 3.83 mmol) in DMSO (2 ml) in a 25 mL microwave vial, was added DIEA (2.67 ml, 15.31 mmol). The mixture was stirred at 80° C. overnight. The mixture was diluted with water (5 ml) and extracted with DCM (3×5 mL). The extracts were combined, dried over MgSO$_4$ and concentrated to dryness, then purified by silica gel chromatography, eluting with ethyl acetate and hexanes, to give the mixed cis products. This material was then purified by SFC on a AD-H (21×250 mm) column (CO$_2$/EtOH) to separate the (3R,4S) and (3S,4R) compounds. Absolute stereoconfiguration was not determined; the compounds are identified as Cis Isomer 1 and Cis Isomer 2. MS of mixed cis product [M+H]$^+$: 260.

Intermediate D18

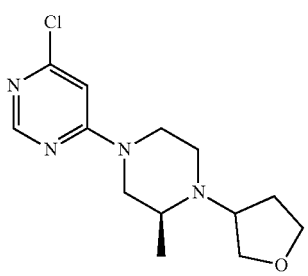 [SMILES: C[C@H]1CN(c2cc(Cl)ncn2)CCN1C1CCOC1]

4-chloro-6-((3S)-3-methyl-4-(tetrahydrofuran-3-yl)piperazin-1-yl)pyrimidine 4,6-dichloropyrimidine (0.083 g, 0.555 mmol), (2S)-2-methyl-1-(tetrahydrofuran-3-yl)piperazine (INTERMEDIATE C, 0.202 g, 0.555 mmol) (bis TFA salt mixed with residual TFA) and DIEA (0.726 ml, 4.16 mmol) were suspended/dissolved in DMSO (2.5 ml) then heated to 90° C. LCMS at 45 minutes showed the reaction was complete. The mixture was cooled to room temperature and ethyl acetate was added. The mixture was filtered, then washed filtrate 3× with water, dried over sodium sulfate, filtered and evaporated. The product was used as is without purification. MS[M+H]$^+$: 283.

Intermediates D19 and D20

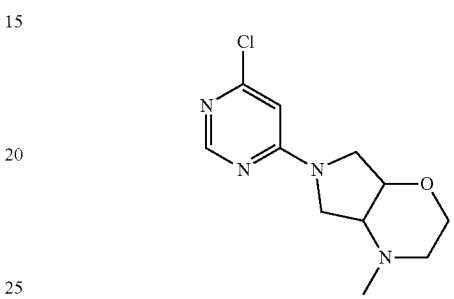

6-(6-chloropyrimidin-4-yl)-4-methyloctahydropyrrolo[3,4-b][1,4]oxazine, peak 1(D19) and peak 2 (D20)

A solution of 4-methyloctahydropyrrolo[3,4-b][1,4]oxazine (550 mg, 3.87 mmol) in DCM (10 ml) was treated with 4,6-dichloropyrimidine (650 mg, 4.36 mmol) and stirred overnight at 20° C., diluted with DCM, washed with water, dried (Na$_2$SO$_4$) and concentrated to dryness. Purification by silica gel chromatography on SiO$_2$ (MeOH/DCM gradient) gave the racemic product. The compounds were resolved by SFC chromatography on a chiral stationary phase (Lux-2, 21×250 mm) under the conditions below to give two compounds.

Peak 1: 5.3 min MS[M+11]$^+$:255.1

Peak 2: 6.1 min MS[M+11]$^+$:255.1

Column & dimensions (mm): Lux-2, 21×250

Outlet Pressure (bar): 100

UV wavelength (nm): 252

Flow rate (ml/min): 70

Modifier: MeOH w/0.25% DMEA

% modifier in CO2: 20

Sample amount (mg): 885

Diluent: 1:1 MeOH/CH3CN

Diluent volume (mL): 40

Injection volume (mL): 0.25

Retention time (min): 5.3, 6.1

Instrument: Sepiatec

The intermediates in Table D2 were prepared according to Scheme D using the procedures outlined in the synthesis of intermediate D1. The pyrimidines and amines utilized in this scheme are either commercially available or their synthesis has been described elsewhere in this document.

TABLE D2

| Intermediate | Structure | Name | MS [M + H]+ |
|---|---|---|---|
| D21 | 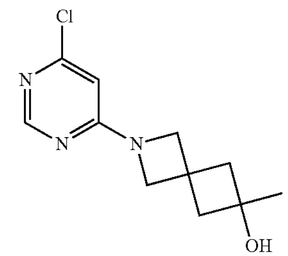 [SMILES: CC1(O)CC2(CN(c3cc(Cl)ncn3)C2)C1] | 2-(6-chloropyrimidin-4-yl)-6-methyl-2-azaspiro[3.3]heptan-6-ol | 240 |
| D22 | 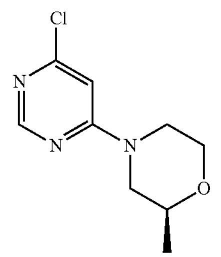 | (S)-4-(6-chloropyrimidin-4-yl)-2-methylmorpholine | 214 |
| D23 | 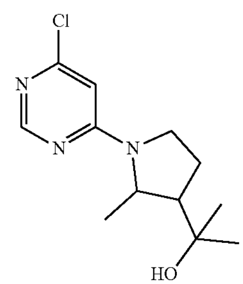 [SMILES: CC1C(C(C)(C)O)CCN1c1cc(Cl)ncn1] | 2-(1-(6-chloropyrimidin-4-yl)-2-methylpyrrolidin-3-yl)propan-2-ol | 256 |
| D24 | 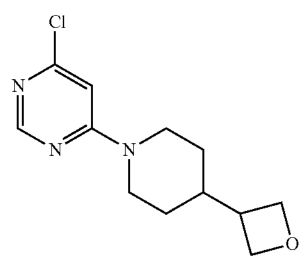 [SMILES: Clc1cc(N2CCC(C3COC3)CC2)ncn1] | 4-chloro-6-(4-(oxetan-3-yl)piperidin-1-yl)pyrimidine | 254 |
| D25 | 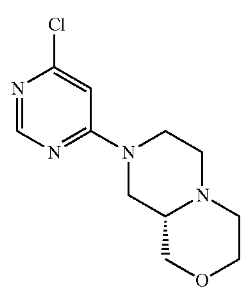 [SMILES: Clc1cc(N2CCN3CCOC[C@@H]3C2)ncn1] | (S)-8-(6-chloropyrimidin-4-yl)octahydropyrazino[2,1-c][1,4]oxazine | 255 |

TABLE D2-continued

| Intermediate | Structure | Name | MS [M + H]+ |
|---|---|---|---|
| D26 | 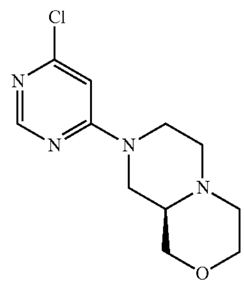 [SMILES: Clc1cc(N2CCN3CCOC[C@H]3C2)ncn1] | (R)-8-(6-chloropyrimidin-4-yl)octahydropyrazino[2,1-c][1,4]oxazine | 255 |
| D27 | 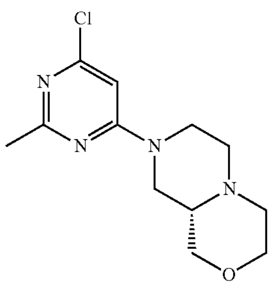 [SMILES: Cc1nc(Cl)cc(N2CCN3CCOC[C@@H]3C2)n1] | (S)-8-(6-chloro-2-methylpyrimidin-4-yl)octahydropyrazino[2,1-c][1,4]oxazine | 269 |

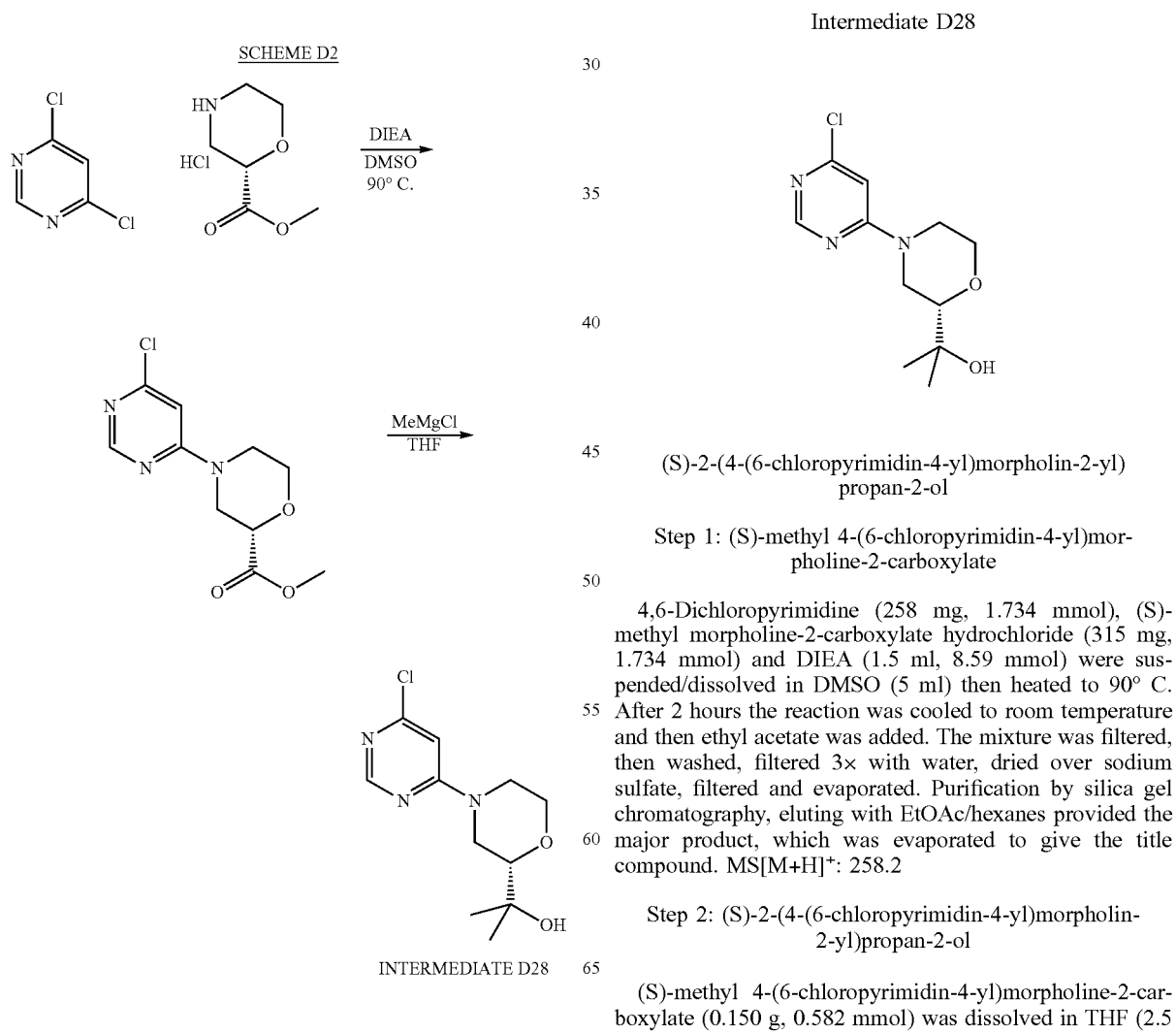

Intermediate D28

(S)-2-(4-(6-chloropyrimidin-4-yl)morpholin-2-yl)propan-2-ol

Step 1: (S)-methyl 4-(6-chloropyrimidin-4-yl)morpholine-2-carboxylate 4,6-Dichloropyrimidine (258 mg, 1.734 mmol), (S)-methyl morpholine-2-carboxylate hydrochloride (315 mg, 1.734 mmol) and DIEA (1.5 ml, 8.59 mmol) were suspended/dissolved in DMSO (5 ml) then heated to 90° C. After 2 hours the reaction was cooled to room temperature and then ethyl acetate was added. The mixture was filtered, then washed, filtered 3× with water, dried over sodium sulfate, filtered and evaporated. Purification by silica gel chromatography, eluting with EtOAc/hexanes provided the major product, which was evaporated to give the title compound. MS[M+H]+: 258.2

Step 2: (S)-2-(4-(6-chloropyrimidin-4-yl)morpholin-2-yl)propan-2-ol (S)-methyl 4-(6-chloropyrimidin-4-yl)morpholine-2-carboxylate (0.150 g, 0.582 mmol) was dissolved in THF (2.5 ml) and cooled to 0° C. under nitrogen. After 10 minutes 3.0 M methylmagnesium chloride (0.450 ml, 1.350 mmol) in THF was added. After 90 minutes the reaction was quenched with aq. NH$_4$Cl, extracted with EtOAc, then washed the organic with water followed by brine, dried over sodium sulfate, filtered and evaporated. The residue was purified by silica gel chromatography, eluting with EtOAc/hexanes. The major peak was isolated to give the title compound. MS[M+H]$^+$: 258.

SCHEME E

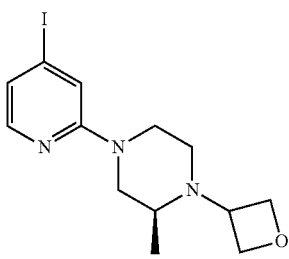 [SMILES: C[C@H]1CN(c2cc(I)ccn2)CCN1C1COC1]

Intermediate E1

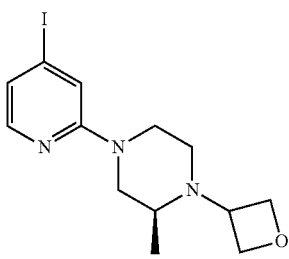 [SMILES: C[C@H]1CN(c2cc(I)ccn2)CCN1C1COC1]

(S)-4-(4-iodopyridin-2-yl)-2-methyl-1-(oxetan-3-yl) piperazine (Scheme E)

Step 1: (S)-4-(4-iodopyridin-2-yl)-2-methyl-1-(oxetan-3-yl)piperazine 2-fluoro-4-iodopyridine (223 mg, 1 mmol) was suspended in DMSO (4 mL). (S)-2-methyl-1-(oxetan-3-yl)piperazine (INTERMEDIATE C2, 350 mg, 1.000 mmol) (bis TFA salt) and DIEA (1310 μl, 7.50 mmol) were added, then the mixture was heated to 150° C. until the reaction was complete. It was then cooled to room temperature and ethyl acetate was added. The product was then filtered, washed filtrate 3× with water, dried over sodium sulfate, filtered again, then evaporated. Purification by silica gel chromatography, eluting with 3:1 EtOAc:EtOH/hexanes, gave the title compound. $^1$H-NMR (CDCl$_3$, 500 MHz) δ 7.83 (d, J=5 Hz, 1H), 7.01 (s, 1H), 6.96 (d, J=5.5 Hz, 1H), 4.74 (q, 2H), 4.63 (m, 2H), 3.86 (dd, J=25.8 Hz, 13 Hz, 1H), 3.74 (m, 1H+EtOH), 3.23 (m, 1H), 2.90 (m, 1H), 2.72 (m, 1H), 2.40 (m, 1H), 2.18 (m, 1H), 1.24 (m, 1H+EtOH), 0.96 (d, J=6.5 Hz, 3H). MS[M+H]$^+$: 360.

Intermediate E2 in Table E was made in the same fashion as intermediate E1.

TABLE E

| Intermediate | Structure | Name | MS [M + H]$^+$ |
|---|---|---|---|
| E2 | 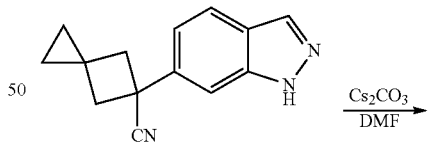 | (2-(4-iodo-pyridin-2-yl)-2-azabicyclo[2.1.1]hexan-4-yl)methanol | 317 |

Schemes

The compounds of the present invention can be prepared in a variety of ways. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. In some cases where there is a stereocenter present, an additional chiral resolution may be carried out to provide enantiomeric products. These examples are illustrative only and should not be construed as limiting the invention in any way.

SCHEME 1

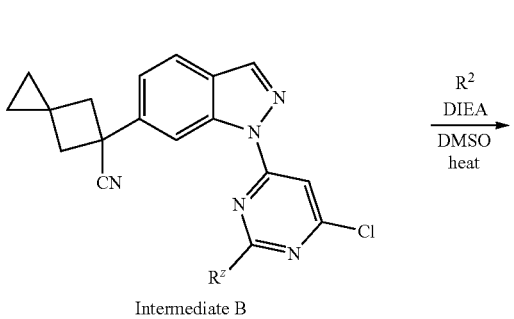

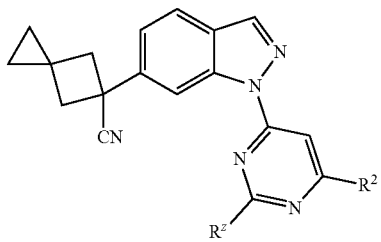

Examples 1-9

Examples 1-9 were prepared by coupling a dichloropyrimidine with Intermediate A1. After separating out the correct regioisomer to give Intermediate B, substituted cyclic amines were coupled with Intermediate B in the presence of a tertiary amine base and heat to give Examples 1-9.

SCHEME 2

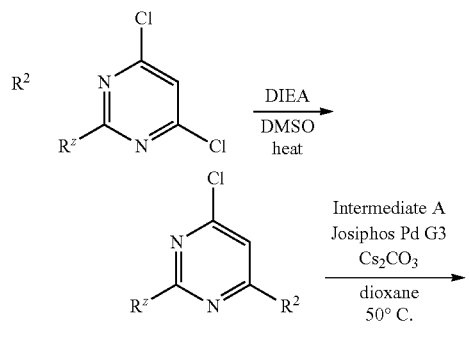

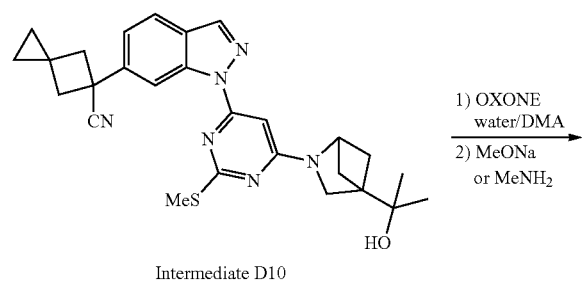

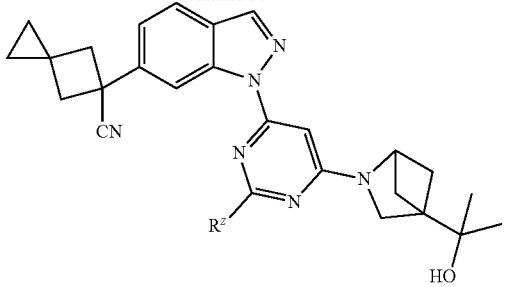

R$^z$ = NHMe (Example 29)
R$^z$ = OMe (Example 30)

Examples 10-28 and 33-56 were prepared by first coupling substituted cyclic amines (either Intermediate C1-C11 or commercial amines) to dichloropyrimidines to give Intermediates D1-D28. In some instances further functional group manipulation was undertaken. These intermediates were then coupled with Intermediate A1-A4 in the presence of Cs$_2$CO$_3$ to give the final product(s). Most of the couplings were done in the presence of Josiphos Pd G3, which suppresses formation of the N(2) regiosiomer. Examples 29 and 30 were prepared from the 2-methylthiopyrimidine intermediate D10 and intermediate A1, which was then oxidized to the sulfone and treated with methylamine and sodium methoxide respectively to give Examples 29 and 30.

SCHEME 3

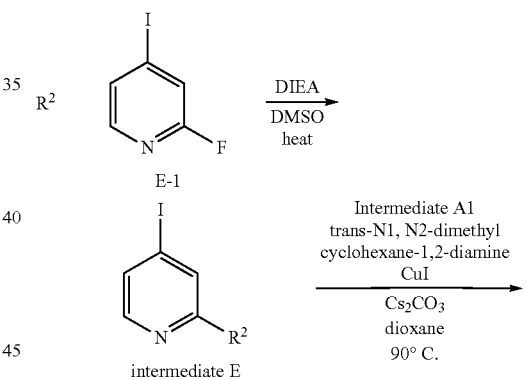

Examples 31-32

Examples 31 and 32 were synthesized by a copper (I) mediated base coupling of Intermediate A1 and Intermediate E1 and E2 respectively, wherein, in Scheme 3, R$^2$ is as defined in Formula (I).

EXAMPLES

Example compounds of the present invention can be synthesized according to the schemes and procedures out-

Example 1

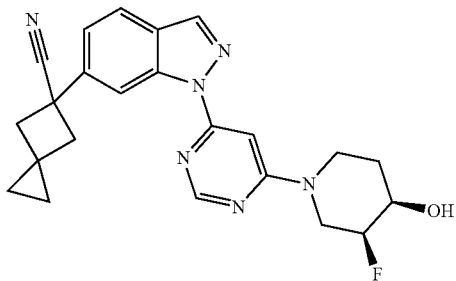 [SMILES: N#CC1(c2ccc3cnn(-c4cc(N5CC[C@@H](O)[C@@H](F)C5)ncn4)c3c2)CC2(CC2)C1]

5-(1-(6-((3S,4R)-3-fluoro-4-hydroxypiperidin-1-yl)pyrimidin-4-yl)-1H-indazol-6-yl)spiro[2.3]hexane-5-carbonitrile 5-(1-(6-chloropyrimidin-4-yl)-1H-indazol-6-yl)spiro[2.3]hexane-5-carbonitrile (INTERMEDIATE B1, 33.6 mg, 0.1 mmol) was suspended in DMSO (0.5 ml). (3S,4R)-3-fluoropiperidin-4-ol hydrochloride (18.67 mg, 0.120 mmol) and DIEA (0.087 ml, 0.500 mmol) were added, then the mixture was heated to 90° C. for 90 minutes, then cooled to 60° C. overnight. The mixture was then cooled to room temperature and then diluted with EtOAc and partitioned with water. The organic layer was washed 3× with water, dried over sodium sulfate, filtered and evaporated, then purified by silica gel chromatography, eluting with 3:1 EtOAc:EtOH/hexanes. The major peak was collected to give the title compound. $^1$H-NMR (CDCl$_3$, 500 MHz): δ 9.16 (s, 1H), 8.61 (s, 1H), 8.21 (s, 1H), 7.80 (d, J=8.5 Hz, 1H), 7.47 (dd, J=8.5, 1.5 Hz, 1H), 7.25 (s, 1H), 4.76 (dd, J=48 Hz, 6 Hz, 1H), 4.29 (m, 1H), 4.10 (m, 1H), 4.02 (m, 1H), 3.87 (m, 1H), 3.58 (m, 1H), 3.10 (d, J=13 Hz, 2H), 2.89 (d, J=13 Hz, 2H), 2.09 (d, J=6 Hz, 1H), 2.06-1.90 (m, 2H), 0.80 (dd, J=8 Hz, 9.5 Hz, 2H), 0.66 (dd, J=7.5 Hz, 9.8 Hz, 2H). MS[M+H]$^+$: 419 LRRK2 IC$_{50}$: 4.4 nM.

Example 2

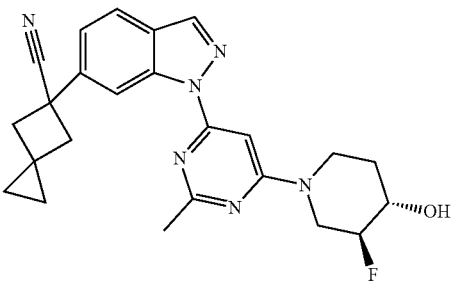 [SMILES: Cc1nc(N2CC[C@H](O)[C@@H](F)C2)cc(-n2ncc3ccc(C4(C#N)CC5(CC5)C4)cc32)n1]

5-(1-(6-((3S,4S)-3-fluoro-4-hydroxypiperidin-1-yl)-2-methylpyrimidin-4-yl)-1H-indazol-6-yl)spiro[2.3]hexane-5-carbonitrile 5-(1-(6-chloro-2-methylpyrimidin-4-yl)-1H-indazol-6-yl)spiro[2.3]hexane-5-carbonitrile (INTERMEDIATE B2, 29.0 mg, 0.083 mmol) was suspended in DMSO (0.5 ml). (3S,4S)-3-fluoropiperidin-4-ol (INTERMEDIATE C3, 21.73 mg, 0.182 mmol) and DIEA (0.072 ml, 0.415 mmol) were added, then the mixture was heated to 75° C. overnight. The mixture was then partitioned between ethyl acetate and water. The organic was washed with water 2× more, then the organic layer was dried over sodium sulfate, filtered and evaporated. The crude was then purified via silica gel chromatography, eluting with 3:1 EtOAc:EtOH in hexanes. The major peak was isolated to give the target compound. $^1$H-NMR (CDCl$_3$, 500 MHz): δ 9.22 (s, 1H), 8.20 (s, 1H), 7.80 (d, J=8.5 Hz, 1H), 7.51 (dd, J=8.5, 1.5 Hz, 1H), 7.07 (s, 1H), 4.71 (m, 1H), 4.46 (m, 1H), 4.37 (m, 1H), 4.29 (d, J=13.5 Hz, 1H), 3.99 (m, 1H), 3.25 (m, 2H), 3.11 (d, J=13 Hz, 2H), 2.88 (d, J=13 Hz, 2H), 2.64 (s, 3H), 2.29 (d, J=3 Hz, 1H), 2.16 (m, 1H), 0.80 (dd, J=8 Hz, 9.5 Hz, 2H), 0.67 (dd, J=6.5 Hz, 9.5 Hz, 2H). MS[M+H]$^+$: 433 LRRK2 IC$_{50}$: 5.1 nM.

The following compounds were prepared according to the general procedure provided in examples 1 and 2, utilizing cyclic amines that are either commercially available or whose preparation is outlined in Scheme C and enumerated as intermediates C1-C7.

TABLE 1

| Example | Structure | Name | MS [M + H]$^+$ | LRRK2 IC$_{50}$ |
|---|---|---|---|---|
| 3 | 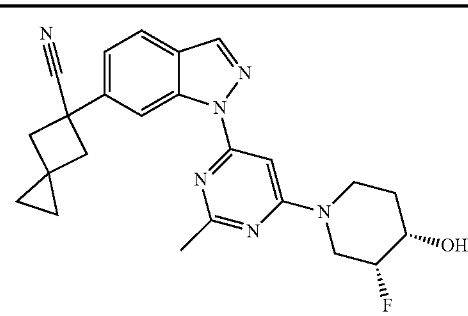 | 5-(1-(6-((3R,4S)-3-fluoro-4-hydroxypiperidin-1-yl)-2-methylpyrimidin-4-yl)-1H-indazol-6-yl)spiro[2.3]hexane-5-carbonitrile | 433 | 18.0 nM |

TABLE 1-continued

| Example | Structure | Name | MS [M + H]+ | LRRK2 IC$_{50}$ |
|---|---|---|---|---|
| 4 | 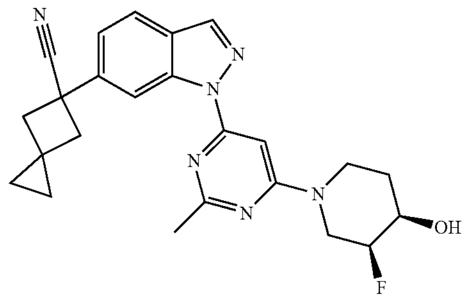 [SMILES: Cc1nc(N2CC[C@@H](O)[C@@H](F)C2)cc(-n2ncc3ccc(C4(C#N)CC5(CC5)C4)cc32)n1] | 5-(1-(6-((3S,4R)-3-fluoro-4-hydroxypiperidin-1-yl)-2-methylpyrimidin-4-yl)-1H-indazol-6-yl)spiro[2.3]hexane-5-carbonitrile | 433 | 7.4 nM |
| 5 | 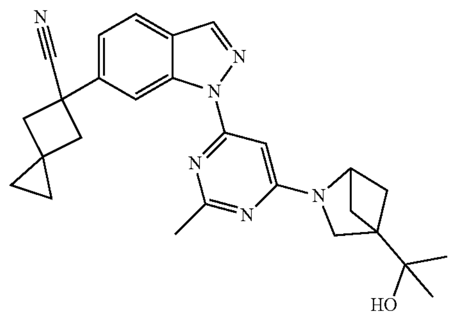 [SMILES: Cc1nc(N2CC3(C(C)(C)O)CC2C3)cc(-n2ncc3ccc(C4(C#N)CC5(CC5)C4)cc32)n1] | 5-(1-(6-(4-(2-hydroxypropan-2-yl)-2-azabicyclo[2.1.1]hexan-2-yl)-2-methylpyrimidin-4-yl)-1H-indazol-6-yl)spiro[2.3]hexane-5-carbonitrile | 455 | 12.3 nM |
| 6 | 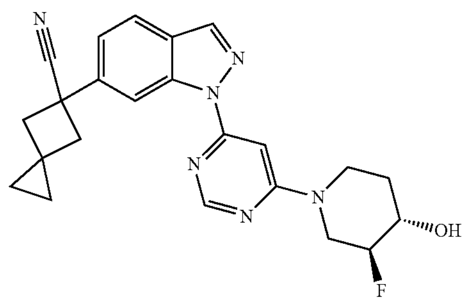 [SMILES: N#CC1(c2ccc3cnn(-c4cc(N5CC[C@H](O)[C@@H](F)C5)ncn4)c3c2)CC2(CC2)C1] | 5-(1-(6-((3S,4S)-3-fluoro-4-hydroxypiperidin-1-yl)pyrimidin-4-yl)-1H-indazol-6-yl)spiro[2.3]hexane-5-carbonitrile | 419 | 6.2 nM |
| 7 | 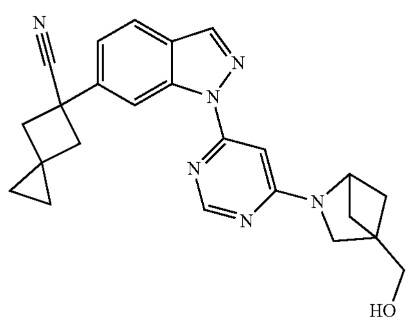 [SMILES: N#CC1(c2ccc3cnn(-c4cc(N5CC6(CO)CC5C6)ncn4)c3c2)CC2(CC2)C1] | 5-(1-(6-(4-(hydroxymethyl)-2-azabicyclo[2.1.1]hexan-2-yl)pyrimidin-4-yl)-1H-indazol-6-yl)spiro[2.3]hexane-5-carbonitrile | 413 | 1.5 nM |
| 8 | 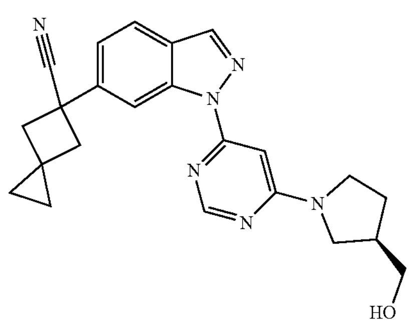 [SMILES: N#CC1(c2ccc3cnn(-c4cc(N5CC[C@@H](CO)C5)ncn4)c3c2)CC2(CC2)C1] | (R)-5-(1-(6-(3-(hydroxymethyl)pyrrolidin-1-yl)pyrimidin-4-yl)-1H-indazol-6-yl)spiro[2.3]hexane-5-carbonitrile | 401 | 2.9 nM |

TABLE 1-continued

| Example | Structure | Name | MS [M + H]+ | LRRK2 IC$_{50}$ |
|---|---|---|---|---|
| 9 | 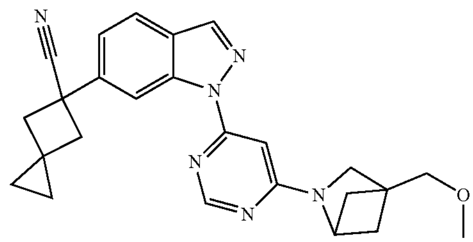 [SMILES: COCC12CC(C1)N(c1cc(-n3ncc4ccc(C5(C#N)CC6(CC6)C5)cc43)ncn1)C2] | 5-(1-(6-(4-(methoxymethyl)-2-azabicyclo[2.1.1]hexan-2-yl)pyrimidin-4-yl)-1H-indazol-6-yl)spiro[2.3]hexane-5-carbonitrile | 427 | 9.3 nM |

Example 10

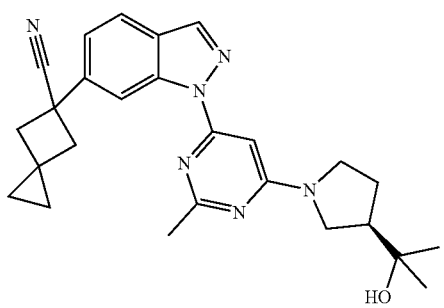 [SMILES: Cc1nc(N2CC[C@@H](C(C)(C)O)C2)cc(-n2ncc3ccc(C4(C#N)CC5(CC5)C4)cc32)n1]

(R)-5-(1-(6-(3-(2-hydroxypropan-2-yl)pyrrolidin-1-yl)-2-methylpyrimidin-4-yl)-1H-indazol-6-yl)spiro[2.3]hexane-5-carbonitrile (R)-2-(1-(6-chloro-2-methylpyrimidin-4-yl)pyrrolidin-3-yl)propan-2-ol (INTERMEDIATE D3, 144 mg, 0.564 mmol) and 5-(1H-indazol-6-yl)spiro[2.3]hexane-5-carbonitrile (INTERMEDIATE A1, 120 mg, 0.537 mmol) were dissolved in DMF (2 mL). Cs$_2$CO$_3$ (263 mg, 0.806 mmol) was added, and the mixture was heated to 80° C. for 2.5 hours. The temperature was then increased to 120° C., and the reaction allowed to run overnight, after which time the reaction was observed to be approximately 50% complete. The product was then partitioned between EtOAc and water. The organic was washed 2× more with water, dried over Na$_2$SO$_4$, filtered and evaporated, then purified by reverse phase HPLC, eluting with a gradient of CH$_3$CN in water (0.1% TFA) to give the title compound and a second product of the same molecular weight. N(1) regioisomer (Title Compound): $^1$H-NMR (CDCl$_3$, 500 MHz): δ 9.25 (s, 1H), 8.20 (s, 1H), 7.80 (d, J=8.5 Hz, 1H), 7.49 (d, J=8.5 Hz, 1H), 6.74 (s, 1H), 4.2-3.3 (m, 4H), 3.11 (d, J=13 Hz, 2H), 2.89 (d, J=13 Hz, 2H), 2.64 (s, 3H), 2.41 (m, 1H), 2.08 (m, 2H), 1.33 (d, J=5 Hz, 6H), 0.80 (dd, J=8 Hz, 9.5 Hz, 2H), 0.67 (dd, J=6.5 Hz, 9.5 Hz, 2H). MS[+H]$^+$: 443 LRRK2 IC$_{50}$: 3.8 nM.

Example 11

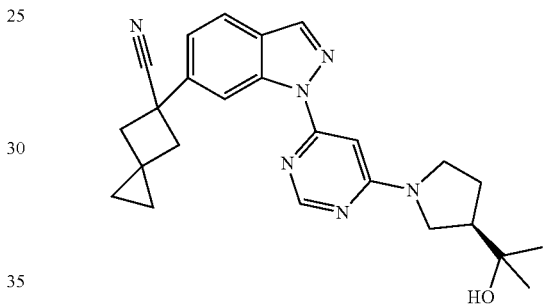

(R)-5-(1-(6-(3-(2-hydroxypropan-2-yl)pyrrolidin-1-yl)pyrimidin-4-yl)-1H-indazol-6-yl)spiro[2.3]hexane-5-carbonitrile (R)-2-(1-(6-chloropyrimidin-4-yl)pyrrolidin-3-yl)propan-2-ol (INTERMEDIATE D1, 846 mg, 3.50 mmol) and 5-(1H-indazol-6-yl)spiro[2.3]hexane-5-carbonitrile (INTERMEDIATE A1, 781 mg, 3.5 mmol), Cs$_2$CO$_3$ (3.42 g, 10.50 mmol) and Josiphos Pd G3 (323 mg, 0.350 mmol) were placed in a vessel which was evacuated and charged 3× with nitrogen. The mixture was suspended/dissolved in dioxane (17.5 mL), stirred at 50° C. overnight, then partitioned between ethyl acetate and water. The organic was washed with water twice more. The organic was dried over sodium sulfate, filtered and evaporated. The crude was purified by silica gel chromatography, eluting with a gradient of 3:1 EtOAc:EtOH in hexanes to give the title compound and a small amount of the regioisomer. The product was purified again, eluting with a gradient of EtOAc in DCM to give the title compound as a single regioisomer. $^1$H-NMR (CDCl$_3$, 500 MHz): δ 9.18 (s, 1H), 8.60 (s, 1H), 8.21 (s, 1H), 7.80 (d, J=13.5 Hz, 1H), 7.47 (dd, J=8.5, 1.5 Hz, 1H), 6.92 (s, 1H), 4.10-3.35 (br, 4H), 3.09 (d, J=12.5 Hz, 2H), 2.89 (d, J=12 Hz, 2H), 2.43 (br, 1H), 2.12 (br, 2H), 1.30 (s, 6H), 0.80 (m, 2H), 0.66 (m, 2H). MS[+H]$^+$: 429 LRRK2 IC$_{50}$: 0.9 nM.

Example 12

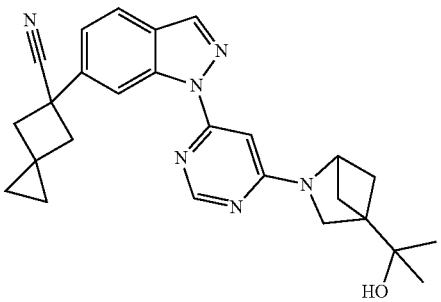 [SMILES: CC(C)(O)C12CC(C1)N(c1cc(-n3ncc4ccc(C5(C#N)CC6(CC6)C5)cc43)ncn1)C2]

5-(1-(6-(4-(2-hydroxypropan-2-yl)-2-azabicyclo[2.1.1]hexan-2-yl)pyrimidin-4-yl)-1H-indazol-6-yl)spiro[2.3]hexane-5-carbonitrile 2-(2-(6-chloropyrimidin-4-yl)-2-azabicyclo[2.1.1]hexan-4-yl)propan-2-ol (INTERMEDIATE D2, 0.781 g, 3.08 mmol) and 5-(1H-indazol-6-yl)spiro[2.3]hexane-5-carbonitrile (INTERMEDIATE A1) 0.688 g, 3.08 mmol), Cs$_2$CO$_3$ (3.01 g, 9.24 mmol), and Josiphos Pd G3 (0.285 g, 0.308 mmol) were mixed, evacuated, and charged 3× with nitrogen, then suspended/dissolved in dioxane (15.40 ml). The mixture was stirred at 50° C. overnight. At 21 hours the reaction temperature was increased to 65° C. At 24 hours the mixture was partitioned between ethyl acetate and water. The organic layer was washed with water twice more, then dried over sodium sulfate, filtered and evaporated, then purified by silica gel chromatography, eluting with a gradient of EtOAc in DCM to give the target compound. $^1$H-NMR (CDCl$_3$, 500 MHz): δ 9.17 (s, 1H), 8.56 (s, 1H), 8.21 (s, 1H), 7.80 (d, J=8.5 Hz, 1H), 7.47 (d, J=8 Hz, 1H), 6.96 (br s, 1H), 5.20-4.80 (br, 2H), 3.51 (br, 2H), 3.10 (d, J=13 Hz, 2H), 2.90 (d, J=12.5 Hz, 2H), 2.03 (s, 2H), 1.59 (d, J=4.5 Hz, 1H), 1.33 (s, 6H), 0.80 (m, 2H), 0.66 (m, 2H). MS[M+H]$^+$: 441 LRRK2 IC$_{50}$: 2.6 nM.

Example 13

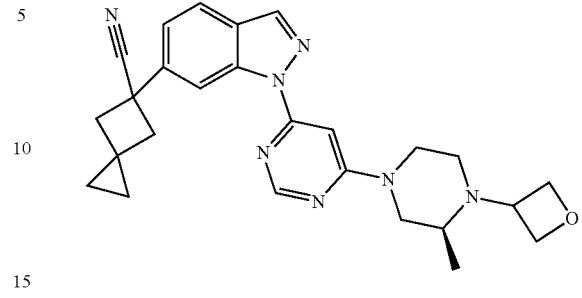

(S)-5-(1-(6-(3-methyl-4-(oxetan-3-yl)piperazin-1-yl)pyrimidin-4-yl)-1H-indazol-6-yl)spiro[2.3]hexane-5-carbonitrile (S)-4-chloro-6-(3-methyl-4-(oxetan-3-yl)piperazin-1-yl)pyrimidine (INTERMEDIATE D5, 81 mg, 0.300 mmol) and 5-(1H-indazol-6-yl)spiro[2.3]hexane-5-carbonitrile (INTERMEDIATE A1, 67.0 mg, 0.3 mmol), Cs$_2$CO$_3$ (293 mg, 0.900 mmol) and Josiphos Pd G3 (27.7 mg, 0.030 mmol) were mixed, evacuated, and charged 3× with nitrogen, then suspended/dissolved in dioxane (1500 μl). The mixture was then stirred at room temperature overnight. LCMS indicated no reaction, so the temperature was raised to 50° C. and stirred overnight to completion. The reaction product was then cooled to room temperature and partitioned between ethyl acetate and water. The organic was washed with water twice more, then dried over sodium sulfate, filtered and evaporated, purified by silica gel chromatography, eluted with 3:1 EtOAc:EtOH in DCM, then evaporated with diethyl ether. Evaporation gave the title compound. $^1$H-NMR (CDCl$_3$, 500 MHz): δ 9.16 (s, 1H), 8.59 (s, 1H), 8.21 (s, 1H), 7.80 (d, J=8.5 Hz, 1H), 7.47 (dd, J=8.5, 1.5 Hz, 1H), 7.16 (s, 1H), 4.74 (m, 2H), 4.65 (m, 2H), 4.08 (br, 1H), 3.78 (m, 1H), 3.45 (m, 1H), 3.14 (m, 1H), 3.10 (d, J=12 Hz, 2H), 2.90 (d, J=12.5 Hz, 2H), 2.75 (m, 1H), 2.46 (t, J=6 Hz, 1H), 2.22 (m, 1H), 1.00 (d, J=6.5 Hz, 3H), 0.81 (m, 2H), 0.66 (m, 2H). MS[M+H]$^+$: 456 LRRK2 IC$_{50}$: 1.0 nM.

The following compounds were prepared according to the general procedure provided in examples 11 and 12, utilizing intermediates D1-D17, whose preparations are outlined in scheme D.

TABLE 2

| Example | Structure | Name | MS [M + H]$^+$ | LRRK2 IC$_{50}$ |
|---------|-----------|------|----------------|-----------------|
| 14 | 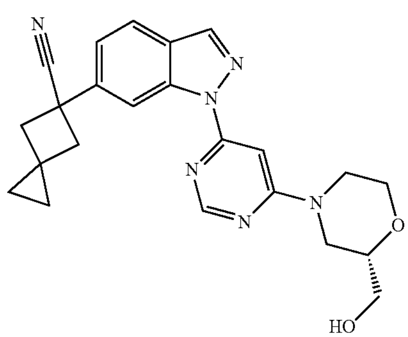 [SMILES: N#CC1(c2ccc3cnn(-c4cc(N5CCO[C@H](CO)C5)ncn4)c3c2)CC2(CC2)C1] | (S)-5-(1-(6-(2-(hydroxymethyl)morpholino)pyrimidin-4-yl)-1H-indazol-6-yl)spiro[2.3]hexane-5-carbonitrile | 417 | 2.9 nM |

TABLE 2-continued

| Example | Structure | Name | MS [M + H]+ | LRRK2 IC$_{50}$ |
|---|---|---|---|---|
| 15 | 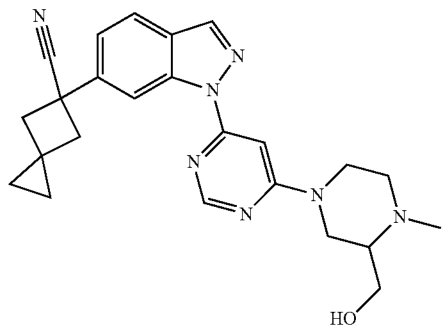 [SMILES: CN1CCN(c2cc(-n3ncc4ccc(C5(C#N)CC6(CC6)C5)cc43)ncn2)CC1CO] | 5-(1-(6-(3-(hydroxymethyl)-4-methylpiperazin-1-yl)pyrimidin-4-yl)-1H-indazol-6-yl)spiro[2.3]hexane-5-carbonitrile, isomer 1 | 430 | 3.8 nM |
| 16 | 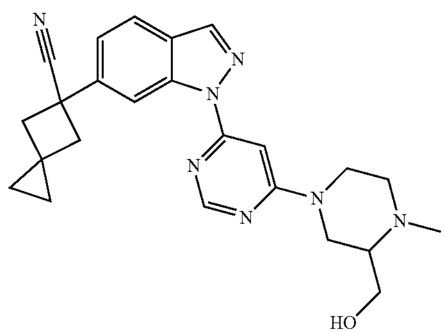 [SMILES: CN1CCN(c2cc(-n3ncc4ccc(C5(C#N)CC6(CC6)C5)cc43)ncn2)CC1CO] | 5-(1-(6-(3-(hydroxymethyl)-4-methylpiperazin-1-yl)pyrimidin-4-yl)-1H-indazol-6-yl)spiro[2.3]hexane-5-carbonitrile, isomer 2 | 430 | 1.2 nM |
| 17 | 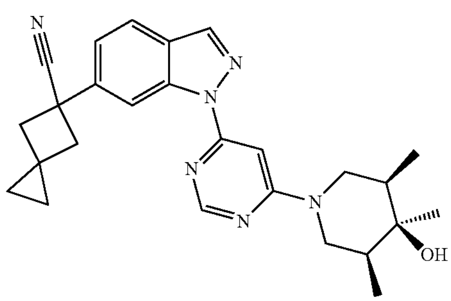 [SMILES: C[C@@H]1CN(c2cc(-n3ncc4ccc(C5(C#N)CC6(CC6)C5)cc43)ncn2)C[C@H](C)[C@]1(C)O] | 5-(1-(6-((3S,4s,5R and 3R,4s,5S)-4-hydroxy-3,4,5-trimethylpiperidin-1-yl)pyrimidin-4-yl)-1H-indazol-6-yl)spiro[2.3]hexane-5-carbonitrile* | 443 | 8.9 nM |
| 18 | 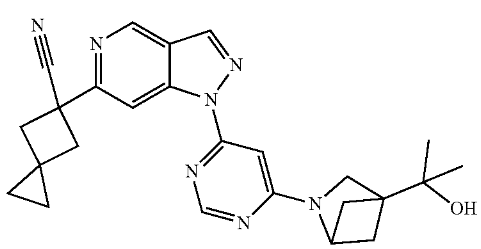 [SMILES: CC(C)(O)C12CC(C1)N(c1cc(-n3ncc4cnc(C5(C#N)CC6(CC6)C5)cc43)ncn1)C2] | 5-(1-(6-(4-(2-hydroxypropan-2-yl)-2-azabicyclo[2.1.1]hexan-2-yl)pyrimidin-4-yl)-1H-pyrazolo[4,3-c]pyridin-6-yl)spiro[2.3]hexane-5-carbonitrile | 442 | 19.2 nM |
| 19 | 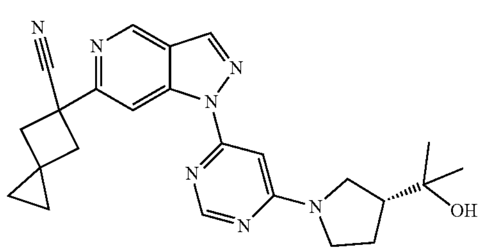 [SMILES: CC(C)(O)[C@@H]1CCN(c2cc(-n3ncc4cnc(C5(C#N)CC6(CC6)C5)cc43)ncn2)C1] | (R)-5-(1-(6-(3-(2-hydroxypropan-2-yl)pyrrolidin-1-yl)pyrimidin-4-yl)-1H-pyrazolo[4,3-c]pyridin-6-yl)spiro[2.3]hexane-5-carbonitrile | 430 | 10.7 nM |

TABLE 2-continued

| Example | Structure | Name | MS [M + H]+ | LRRK2 IC$_{50}$ |
|---|---|---|---|---|
| 20 | 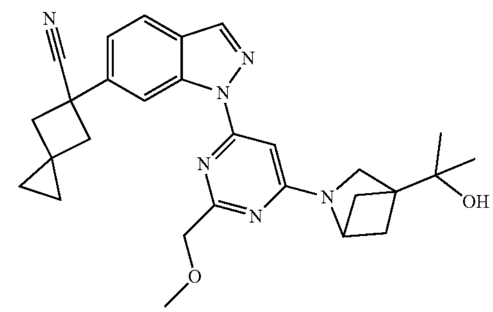 [SMILES: COCc1nc(N2CC3(C(C)(C)O)CC2C3)cc(-n2ncc3ccc(C4(C#N)CC5(CC5)C4)cc32)n1] | 5-(1-(6-(4-(2-hydroxypropan-2-yl)-2-azabicyclo[2.1.1]hexan-2-yl)-2-(methoxymethyl)pyrimidin-4-yl)-1H-indazol-6-yl)spiro[2.3]hexane-5-carbonitrile | 485 | 16.2 nM |
| 21 | 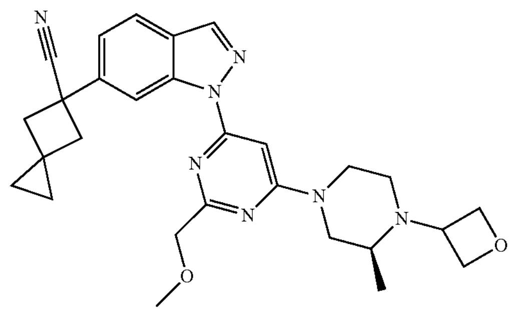 [SMILES: COCc1nc(N2CCN(C3COC3)[C@@H](C)C2)cc(-n2ncc3ccc(C4(C#N)CC5(CC5)C4)cc32)n1] | (S)-5-(1-(2-(methoxymethyl)-6-(3-methyl-4-(oxetan-3-yl)piperazin-1-yl)pyrimidin-4-yl)-1H-indazol-6-yl)spiro[2.3]hexane-5-carbonitrile | 500 | 10.9 nM |
| 22 | 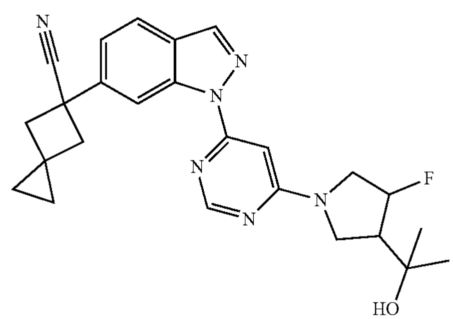 [SMILES: CC(C)(O)C1CN(c2cc(-n3ncc4ccc(C5(C#N)CC6(CC6)C5)cc43)ncn2)CC1F] | 5-(1-(6-(3-fluoro-4-(2-hydroxypropan-2-yl)pyrrolidin-1-yl)pyrimidin-4-yl)-1H-indazol-6-yl)spiro[2.3]hexane-5-carbonitrile, cis isomer 1 | 447 | 3.7 nM |
| 23 | 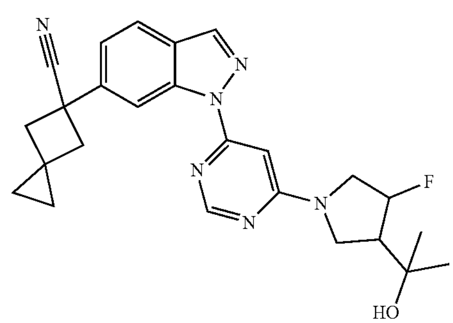 [SMILES: CC(C)(O)C1CN(c2cc(-n3ncc4ccc(C5(C#N)CC6(CC6)C5)cc43)ncn2)CC1F] | 5-(1-(6-(3-fluoro-4-(2-hydroxypropan-2-yl)pyrrolidin-1-yl)pyrimidin-4-yl)-1H-indazol-6-yl)spiro[2.3]hexane-5-carbonitrile, cis isomer 2 | 447 | 4.6 nM |
| 24 | 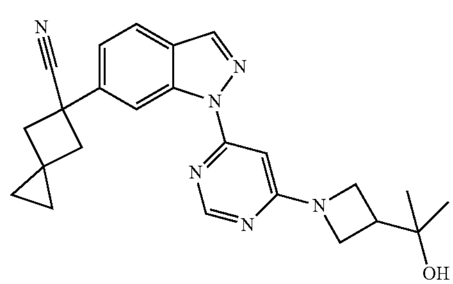 [SMILES: CC(C)(O)C1CN(c2cc(-n3ncc4ccc(C5(C#N)CC6(CC6)C5)cc43)ncn2)C1] | 5-(1-(6-(3-(2-hydroxypropan-2-yl)azetidin-1-yl)pyrimidin-4-yl)-1H-indazol-6-yl)spiro[2.3]hexane-5-carbonitrile | 415 | 2.6 nM |

TABLE 2-continued

| Example | Structure | Name | MS [M + H]+ | LRRK2 IC$_{50}$ |
|---|---|---|---|---|
| 25 | 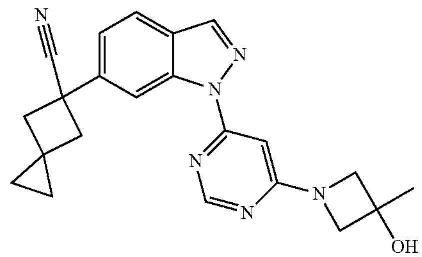 [SMILES: CC1(O)CN(c2cc(-n3ncc4ccc(C5(C#N)CC6(CC6)C5)cc43)ncn2)C1] | 5-(1-(6-(3-hydroxy-3-methylazetidin-1-yl)pyrimidin-4-yl)-1H-indazol-6-yl)spiro[2.3]hexane-5-carbonitrile | 387 | 2.9 nM |
| 26 | 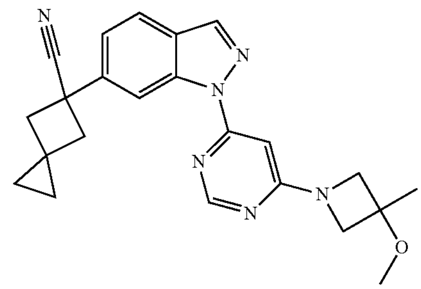 [SMILES: COC1(C)CN(c2cc(-n3ncc4ccc(C5(C#N)CC6(CC6)C5)cc43)ncn2)C1] | 5-(1-(6-(3-methoxy-3-methylazetidin-1-yl)pyrimidin-4-yl)-1H-indazol-6-yl)spiro[2.3]hexane-5-carbonitrile | 401 | 4.3 nM |
| 27 | 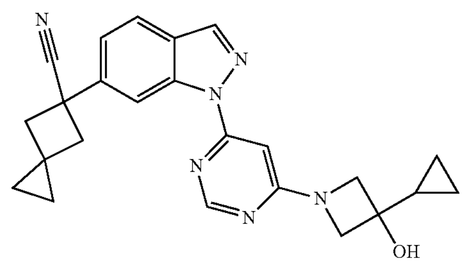 [SMILES: N#CC1(c2ccc3cnn(-c4cc(N5CC(O)(C6CC6)C5)ncn4)c3c2)CC2(CC2)C1] | 5-(1-(6-(3-cyclopropyl-3-hydroxyazetidin-1-yl)pyrimidin-4-yl)-1H-indazol-6-yl)spiro[2.3]hexane-5-carbonitrile | 413 | 7.4 nM |
| 28 | 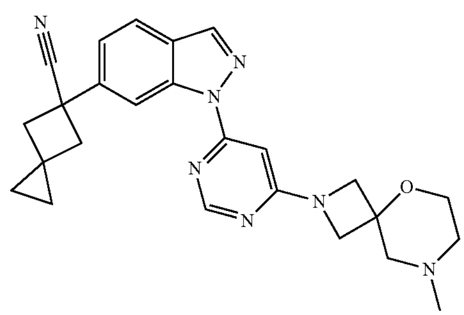 [SMILES: CN1CCOC2(C1)CN(c1cc(-n3ncc4ccc(C5(C#N)CC6(CC6)C5)cc43)ncn1)C2] | 5-(1-(6-(8-methyl-5-oxa-2,8-diazaspiro[3.5]nonan-2-yl)pyrimidin-4-yl)-1H-indazol-6-yl)spiro[2.3]hexane-5-carbonitrile | 442 | 1.3 nM |

*relative configuration.

Example 29

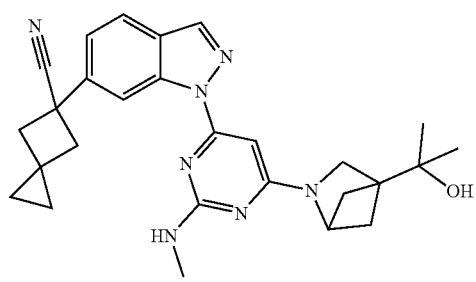 [SMILES: CNc1nc(N2CC3(C(C)(C)O)CC2C3)cc(-n2ncc3ccc(C4(C#N)CC5(CC5)C4)cc32)n1]

5-(1-(6-(4-(2-hydroxypropan-2-yl)-2-azabicyclo[2.1.1]hexan-2-yl)-2-(methylamino)pyrimidin-4-yl)-1H-indazol-6-yl)spiro[2.3]hexane-5-carbonitrile Step 1: 5-(1-(6-(4-(2-hydroxypropan-2-yl)-2-azabicyclo[2.1.1]hexan-2-yl)-2-(methylthio)pyrimidin-4-yl)-1H-indazol-6-yl)spiro[2.3]hexane-5-carbonitrile Utilizing the procedure for Example 12 and substituting intermediate D10 for intermediate D2, the title compound was prepared. MS[M+H]+: 487.

Step 2: 5-(1-(6-(4-(2-hydroxypropan-2-yl)-2-azabi-cyclo[2.1.1]hexan-2-yl)-2-(methylsulfonyl)pyrimidin-4-yl)-1H-indazol-6-yl)spiro[2.3]hexane-5-carbonitrile 5-(1-(6-(4-(2-Hydroxypropan-2-yl)-2-azabicyclo[2.1.1]hexan-2-yl)-2-(methylthio)pyrimidin-4-yl)-1H-indazol-6-yl)spiro[2.3]hexane-5-carbonitrile (250 mg, 0.514 mmol) was suspended in DMA (3 ml). OXONE™ (695 mg, 1.130 mmol) was added, followed by water (1.000 ml). Another 1 eq of OXONE™ (350 mg) was added after 5 hours and the mixture was stirred overnight, then quenched with saturated NH$_4$Cl (10 ml), then extracted with ethyl acetate (3×15 ml). The EtOAc extracts were combined, dried over MgSO$_4$, filtered and evaporated to dryness. The residue was purified by silica gel chromatography eluting with ethyl acetate/hexanes to give the title compound. MS[M+H]$^+$: 519.

Step 3: 5-(1-(6-(4-(2-hydroxypropan-2-yl)-2-azabi-cyclo[2.1.1]hexan-2-yl)-2-(methylamino) pyrimidin-4-yl)-1H-indazol-6-yl)spiro[2.3]hexane-5-carbonitrile A suspension of 5-(1-(6-(4-(2-hydroxypropan-2-yl)-2-azabicyclo[2.1.1]hexan-2-yl)-2-(methylsulfonyl)pyrimidin-4-yl)-1H-indazol-6-yl)spiro[2.3]hexane-5-carbonitrile (50 mg, 0.096 mmol), methylamine hydrochloride (52.1 mg, 0.771 mmol), and Cs$_2$CO$_3$ (314 mg, 0.964 mmol) in DMSO (1 ml) was heated in a 2 ml vial at 80° C. for 6 hrs. The mixture was filtered and purified by reverse phase HPLC, eluting with CH$_3$CN/water (0.1% TFA) to give the title compound. $^1$H-NMR (CD$_3$OD, 500 MHz): δ 9.07 (s, 1H), 8.31 (s, 1H), 7.92 (d, J=8 Hz, 1H), 7.58 (dd, J=8.5, 1.5 Hz, 1H), 6.54 (br, 1H), 3.52 (s, 2H), 3.14 (s, 3H), 2.96 (m, 4H), 2.06 (s, 2H), 1.57 (s, 2H) 1.30 (s, 6H), 0.81 (m, 2H), 0.65 (m, 2H). MS[+H]$^+$: 470 LRRK2 IC$_{50}$: 16.7 nM.

Example 30

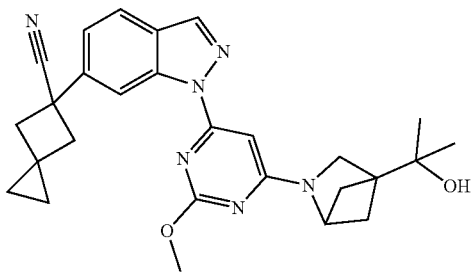 [SMILES: COc1nc(N2CC3(C(C)(C)O)CC2C3)cc(-n2ncc3ccc(C4(C#N)CC5(CC5)C4)cc32)n1]

5-(1-(6-(4-(2-hydroxypropan-2-yl)-2-azabicyclo[2.1.1]hexan-2-yl)-2-methoxypyrimidin-4-yl)-1H-indazol-6-yl)spiro[2.3]hexane-5-carbonitrile To a 2 mL vial containing 5-(1-(6-(4-(2-hydroxypropan-2-yl)-2-azabicyclo[2.1.1]hexan-2-yl)-2-(methylsulfonyl)pyrimidin-4-yl)-1H-indazol-6-yl)spiro[2.3]hexane-5-carbonitrile (see Example 21 step 2, 50 mg, 0.096 mmol) was added sodium methoxide (1.543 ml, 0.771 mmol) solution in MeOH (0.5 M). The vial was sealed and stirred at 80° C. for 4 hrs. The reaction mixture was evaporated, then purified by reverse phase HPLC, eluting with CH$_3$CN/water (0.1% TFA) to give the title compound. $^1$H-NMR (CD$_3$OD, 500 MHz): δ 8.90 (s, 1H), 8.24 (s, 1H), 7.85 (d, J=8 Hz, 1H), 7.59 (dd, J=8.5, 1.5 Hz, 1H), 6.62 (br, 1H), 4.10 (s, 3H), 3.51 (s, 2H), 2.98 (d, J=13 Hz, 2H), 2.88 (d, J=12.5 Hz, 2H). 2.08 (s, 2H), 1.60 (s, 2H) 1.31 (s, 6H), 0.80 (m, 2H), 0.65 (m, 2H). MS[M+H]$^+$: 471 LRRK2 IC$_{50}$: 12.3 nM.

Example 31

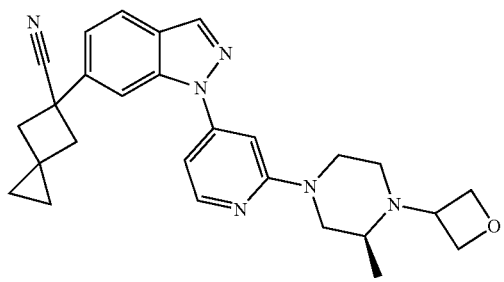 [SMILES: C[C@H]1CN(c2cc(-n3ncc4ccc(C5(C#N)CC6(CC6)C5)cc43)ccn2)CCN1C1COC1]

(S)-5-(1-(2-(3-methyl-4-(oxetan-3-yl)piperazin-1-yl)pyridin-4-yl)-1H-indazol-6-yl)spiro[2.3]hexane-5-carbonitrile (S)-4-(4-iodopyridin-2-yl)-2-methyl-1-(oxetan-3-yl)piperazine (INTERMEDIATE E1, 78 mg, 0.216 mmol) and 5-(1H-indazol-6-yl)spiro[2.3]hexane-5-carbonitrile (INTERMEDIATE A1, 40.2 mg, 0.18 mmol), Cs$_2$CO$_3$ (176 mg, 0.540 mmol), trans-N1,N2-dimethylcyclohexane-1,2-diamine (10.24 mg, 0.072 mmol) and copper(I) iodide (6.86 mg, 0.036 mmol) were added to a reaction vial, which was then evacuated and charged 3× with nitrogen. The mixture was suspended/dissolved in dioxane (900 µl), then degassed by evacuation and recharged with nitrogen (3×), then stirred at 90° C. overnight. The product was cooled to room temperature, then partitioned between ethyl acetate and water. The organic was washed with water twice more, then dried the organic over sodium sulfate, filtered and evaporated, then purified by silica gel chromatography, eluting with 3:1 EtOAc:EtOH in hexanes to give the title compound after evaporation of the requisite product fractions. $^1$H-NMR (CDCl$_3$, 500 MHz): δ 8.33 (d, J=5.5 Hz, 1H), 8.24 (s, 1H), 8.06 (s, 1H), 7.88 (d, J=8.5 Hz, 1H), 7.52 (d, J=8.5, 1H), 7.07 (d, J=5.5 Hz, 1H), 7.05 (s, 1H), 4.75 (m, 2H), 4.65 (m, 2H), 4.05 (d, J=12.5 Hz, 1H), 3.99 (d, J=12.5 Hz, 1H), 3.78 (m, 1H), 3.32 (m, 1H), 3.08 (d, J=13 Hz, 2H), 3.01 (m, 1H), 2.83 (d, J=12.5 Hz, 2H), 2.77 (d, J=11.5 Hz, 1H), 2.47 (t, J=6 Hz, 1H), 2.25 (m, 1H), 1.01 (d, J=6.5 Hz, 3H), 0.82 (m, 2H), 0.65 (m, 2H). MS[M+H]$^+$: 455 LRRK2 IC$_{50}$: 11.3 nM.

Example 32

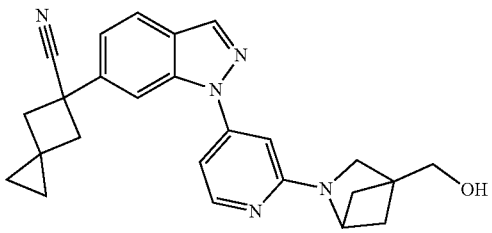 [SMILES: N#CC1(c2ccc3cnn(-c4ccnc(N5CC6(CO)CC5C6)c4)c3c2)CC2(CC2)C1]

5-(1-(2-(4-(hydroxymethyl)-2-azabicyclo[2.1.1]hexan-2-yl)pyridin-4-yl)-1H-indazol-6-yl)spiro[2.3]hexane-5-carbonitrile (2-(4-iodopyridin-2-yl)-2-azabicyclo[2.1.1]hexan-4-yl)methanol (INTERMEDIATE E2, 80 mg, 0.252 mmol), 5-(1H-indazol-6-yl)spiro[2.3]hexane-5-carbonitrile (INTERMEDIATE A1, 46.9 mg, 0.21 mmol), $Cs_2CO_3$ (205 mg, 0.630 mmol), trans-N1,N2-dimethylcyclohexane-1,2-diamine (0.013 ml, 0.084 mmol) and copper(I) iodide (8.00 mg, 0.042 mmol) were added to a reaction vial, which was then evacuated and charged 3× with nitrogen. The mixture was then suspended/dissolved in dioxane (1.0 ml), then degassed by 3× evacuation and recharge with nitrogen, then stirred at 90° C. overnight, then cooled to room temperature. The resulting mixture was partitioned between ethyl acetate and water. The organic layer was washed with water 2× more, then dried over sodium sulfate, filtered and evaporated, then purified by silica gel chromatography, eluting with 3:1 EtOAc:EtOH in hexanes to give the target compound after evaporation of the product containing fractions. $^1$H-NMR (CDCl$_3$, 500 MHz): δ 8.30 (d, J=5.5 Hz, 1H), 8.24 (s, 1H), 8.14 (s, 1H), 7.89 (d, J=8.5 Hz, 1H), 7.54 (d, J=8.5, 1H), 7.04 (d, J=5 Hz, 1H), 6.90 (s, 1H), 4.88 (s, 1H), 3.93 (d, J=5.5 Hz, 2H), 3.51 (s, 2H), 3.09 (d, J=12.5 Hz, 2H), 2.84 (d, J=12.5 Hz, 2H), 1.95 (s, 2H), 1.73 (t, J=6 Hz, 1H), 1.64 (s, 2H), 0.81 (m, 2H), 0.67 (m, 2H). MS[M+H]$^+$: 412 LRRK2 IC$_{50}$: 10.0 nM.

Example 33

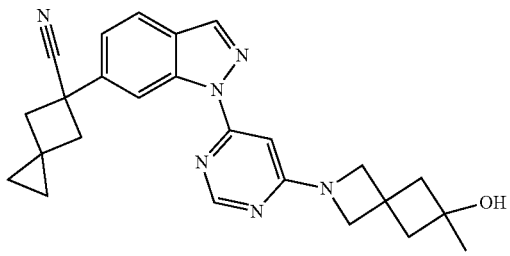 [SMILES: CC1(O)CC2(CN(c3cc(-n4ncc5ccc(C6(C#N)CC7(CC7)C6)cc54)ncn3)C2)C1]

5-(1-(6-(6-hydroxy-6-methyl-2-azaspiro[3.3]heptan-2-yl)pyrimidin-4-yl)-1H-indazol-6-yl)spiro[2.3]hexane-5-carbonitrile A vial containing 2-(6-chloropyrimidin-4-yl)-6-methyl-2-azaspiro[3.3]heptan-6-ol (INTERMEDIATE D21, 47.9 mg, 0.200 mmol) and 5-(1H-indazol-6-yl)spiro[2.3]hexane-5-carbonitrile (INTERMEDIATE A1, 44.7 mg, 0.200 mmol), $Cs_2CO_3$ (195 mg, 0.600 mmol) and Josiphos Pd G3 (18.5 mg, 0.020 mmol) was evacuated and charged 3× with nitrogen. The mixture was suspended/dissolved in dioxane (10 mL), stirred at 50° C. overnight, cooled to room temperature, then partitioned between ethyl acetate and water. The organic layer was washed with water 2× more, then dried the organic over sodium sulfate, filtered and evaporated. Purification by silica gel chromatography, followed by eluting with 3:1 EtOAc:EtOH in hexanes gave the title compound.

$^1$H-NMR (CDCl$_3$, 500 MHz): δ 9.16 (s, 1H), 8.57 (s, 1H), 8.21 (s, 1H), 7.79 (d, J=8 Hz, 1H), 7.47 (d, J=9 Hz, 1H), 6.77 (s, 1H), 4.19 (d, J=16.5 Hz, 4H), 3.09 (d, J=12 Hz, 2H), 2.89 (d, J=12 Hz, 2H), 2.41 (s, 4H), 1.67 (s, 1H), 1.41 (s, 3H), 0.80 (m, 2H), 0.65 (m, 2H). MS[M+H]$^+$: 427 LRRK2 IC$_{50}$: 1.0 nM.

Examples 34 and 35

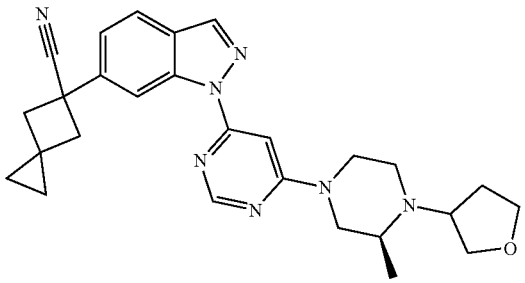 [SMILES: C[C@H]1CN(c2cc(-n3ncc4ccc(C5(C#N)CC6(CC6)C5)cc43)ncn2)CCN1C1CCOC1]

5-(1-(6-((3S)-3-methyl-4-(tetrahydrofuran-3-yl)piperazin-1-yl)pyrimidin-4-yl)-1H-indazol-6-yl)spiro[2.3]hexane-5-carbonitrile, Isomer 1 (EXAMPLE 34) and Isomer 2 (EXAMPLE 35)

A vial containing 4-chloro-6-((3S)-3-methyl-4-(tetrahydrofuran-3-yl)piperazin-1-yl)pyrimidine (INTERMEDIATE D18, 58 mg, 0.205 mmol) and 5-(1H-indazol-6-yl)spiro[2.3]hexane-5-carbonitrile (INTERMEDIATE A1, 45.8 mg, 0.205 mmol), $Cs_2CO_3$ (200 mg, 0.615 mmol) and Josiphos Pd G3 (18.95 mg, 0.021 mmol) was evacuated and charged 3× with nitrogen, suspended/dissolved in dioxane (1025 µl), stirred at 50° C. overnight, cooled to room temperature, then partitioned between ethyl acetate and water. The organic layer was washed with water 2× more, then dried the organic over sodium sulfate, filtered and evaporated. Purification by silica gel chromatography eluting with EtOAc in hexanes, followed by 3:1 EtOAc:EtOH in hexanes gave the racemic product. Chiral purification was done on an AD-H column, followed by eluting with 40% 1:1 ACN:MeOH in CO$_2$, with 0.1% DIPA as modifier, to give two isomeric products.

5-(1-(6-((3S)-3-methyl-4-(tetrahydrofuran-3-yl)piperazin-1-yl)pyrimidin-4-yl)-1H-indazol-6-yl)spiro[2.3]hexane-5-carbonitrile, isomer 1 (time 3.6 min) $^1$H-NMR (CDCl$_3$, 500 MHz): δ 9.16 (s, 1H), 8.59 (s, 1H), 8.21 (s, 1H), 7.79 (d, J=8 Hz, 1H), 7.47 (d, J=8.5 Hz, 1H), 7.15 (s, 1H), 3.99 (m, 1H), 3.82-3.65 (m, 5H), 3.53 (m, 1H), 3.10 (d, J=12 Hz, 2H), 2.90 (d, J=12 Hz, 2H), 2.85 (m, 2H), 2.62 (m, 1H), 2.18 (m, 1H), 1.93 (m, 1H), 1.14 (d, J=6.5 Hz, 3H), 0.80 (m, 2H), 0.66 (m, 2H). MS[M+H]$^+$: 470 LRRK2 IC$_{50}$: 0.9 nM. 5-(1-(6-((3 S)-3-methyl-4-(tetrahydrofuran-3-yl)piperazin-1-yl)pyrimidin-4-yl)-1H-indazol-6-yl)spiro[2.3]hexane-5-carbonitrile, isomer 2 (time 4.14 min) $^1$H-NMR (CDCl$_3$, 500 MHz): δ 9.16 (s, 1H), 8.59 (s, 1H), 8.21 (s, 1H), 7.79 (d, J=8 Hz, 1H), 7.47 (d, J=8.5 Hz, 1H), 7.16 (s, 1H), 3.99 (m, 1H), 3.76 (m, 2H), 3.66 (m, 2H), 3.60 (m, 2H), 3.39 (m, 1H), 3.10 (d, J=11.5 Hz, 2H), 2.91 (br, 1H), 2.90 (d, J=12 Hz, 2H), 2.82 (m, 1H), 2.42 (t, J=8.5 Hz, 1H), 1.95 (m, 1H), 1.89 (m, 1H), 1.16 (d, J=6.5 Hz, 3H), 0.80 (m, 2H), 0.66 (m, 2H). MS[M+H]$^+$: 470 LRRK2 IC$_{50}$: 3.5 nM.

Examples 36, 37, 38 and 39

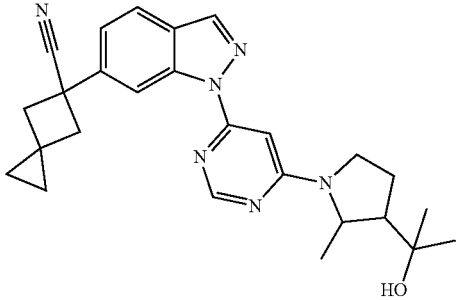 [SMILES: CC1C(C(C)(C)O)CCN1c1cc(-n2ncc3ccc(C4(C#N)CC5(CC5)C4)cc32)ncn1]

5-(1-(6-(3-(2-hydroxypropan-2-yl)-2-methylpyrrolidin-1-yl)pyrimidin-4-yl)-1H-indazol-6-yl)spiro[2.3]hexane-5-carbonitrile, Enantiomer 1 (EXAMPLE 36), Enantiomer 2 (EXAMPLE 37), Enantiomer 3 (EXAMPLE 38) and Enantiomer 4 (EXAMPLE 39)

A vial containing 2-(1-(6-chloropyrimidin-4-yl)-2-methylpyrrolidin-3-yl)propan-2-ol (INTERMEDIATE D23, 151 mg, 0.590 mmol) and 5-(1H-indazol-6-yl)spiro[2.3]hexane-5-carbonitrile (INTERMEDIATE A1, 132 mg, 0.59 mmol), $Cs_2CO_3$ (577 mg, 1.770 mmol) and Josiphos Pd G3 (54.5 mg, 0.059 mmol) was evacuated and charged 3× with nitrogen, then suspended/dissolved in dioxane (3 ml), stirred at 50° C. overnight, cooled to room temperature, and then partitioned between ethyl acetate and water. The organic was washed with water 2× more, then dried the organic over sodium sulfate, filtered and evaporated. The product was purified by silica gel chromatography, followed by eluting with a gradient of 3:1 EtOAc:EtOH in hexanes. Separation was achieved, but only a single product peak was seen; the major peak was isolated and the isolate was pumped on vacuum overnight to give a yellowish oil. Chiral SFC was used to initially separate the diastereomers. Conditions: Whelko-1 column, 35% EtOH (0.2% DIPA) in supercritical $CO_2$. 6.2 mg/mL crude in MeOH, 0.5 mL injection volume gave a gave 1:1 separation of diastereomers.

Whelcko Peak1 (RT: 3.23 min) was then purified on an AD-H column with 45% EtOH (0.2% DIPA) in supercritical $CO_2$ as eluent to give 2 isomers in an approximate 1:1 ratio.

Peak 1 (RT: 3.04 min) corresponds to EXAMPLE 36. $^1$H-NMR (CDCl$_3$, 500 MHz): δ 9.17 (s, 1H), 8.59 (s, 1H), 8.21 (s, 1H), 7.79 (d, J=8 Hz, 1H), 7.46 (dd, J=8.25 Hz, 2 Hz, 1H), 6.93 (s, 1H), 4.23 (m, 1H), 3.55 (m, 1H), 3.09 (d, J=13 Hz, 1H), 3.08 (t, J=10.5 Hz, 1H), 2.90 (d, J=12 Hz, 2H), 2.23 (m, 1H), 2.10 (m, 1H), 2.02 (m, 1H), 1.37 (d, J=6.5 Hz, 3H), 1.34, (s, 1H), 1.29-1.20 (m, 6H), 0.80 (m, 2H), 0.66 (m, 2H). MS[M+H]$^+$: 443 LRRK2 IC$_{50}$: 3.2 nM.

Peak 2 (RT=3.57 min) corresponds to EXAMPLE 37. $^1$H-NMR (CDCl$_3$, 500 MHz): δ 9.17 (s, 1H), 8.59 (s, 1H), 8.21 (s, 1H), 7.79 (d, J=8 Hz, 1H), 7.46 (dd, J=8.25 Hz, 2 Hz, 1H), 6.93 (s, 1H), 4.22 (m, 1H), 3.55 (m, 1H), 3.09 (d, J=13 Hz, 1H), 3.08 (dt, J=12 Hz, 2 Hz, 1H), 2.90 (d, J=12 Hz, 2H), 2.23 (m, 1H), 2.10 (m, 1H), 2.02 (m, 1H), 1.37 (d, J=6.5 Hz, 3H), 1.34, (s, 1H), 1.29-1.20 (m, 6H), 0.80 (m, 2H), 0.66 (m, 2H). MS[M+H]$^+$: 443 LRRK2 IC50=138 nM.

Whelcko Peak 2 (RT: 3.93 min) was purified on an OJ-H column with 20% iPrOH (0.2% DIPA) in supercritical $CO_2$ as eluent to give 2 isomers in an approximate 1:1 ratio.

Peak 1 (RT:2.64 min) corresponds to EXAMPLE 38. $^1$H-NMR (CDCl$_3$, 500 MHz): δ 9.17 (s, 1H), 8.60 (s, 1H), 8.21 (s, 1H), 7.79 (d, J=8.5 Hz, 1H), 7.46 (dd, J=8.25 Hz, 1.5 Hz, 1H), 6.85 (s, 1H), 4.71 (m, 1H), 4.22 (m, 1H), 3.42 (m, 1H), 3.09 (d, J=13 Hz, 2H), 2.91 (d, J=12.5 Hz, 2H), 2.22 (br m, 3H), 1.43 (s, 3H), 1.36 (s, 3H), 1.32, (d, J=6.5 Hz, 3H), 0.80 (m, 2H), 0.66 (m, 2H). MS[M+H]$^+$: 443 LRRK2 IC$_{50}$: 59 nM.

Peak 2 (RT: 2.83 min) corresponds to EXAMPLE 39. $^1$H-NMR (CDCl$_3$, 500 MHz): δ 9.17 (s, 1H), 8.59 (s, 1H), 8.21 (s, 1H), 7.79 (d, J=8 Hz, 1H), 7.46 (dd, J=8.25 Hz, 2 Hz, 1H), 6.85 (s, 1H), 4.71 (m, 1H), 3.62 (m, 1H), 3.42 (m, 1H), 3.09 (d, J=13 Hz, 2H), 2.91 (d, J=12.5 Hz, 2H), 2.22 (br m, 3H), 1.43 (s, 3H), 1.36 (s, 3H), 1.32, (d, J=6.5 Hz, 3H), 0.80 (m, 2H), 0.66 (m, 2H). MS[M+H]$^+$: 443 LRRK2 IC$_{50}$: 1.2 nM The following compounds were prepared according to the general procedure provided in example 1, coupling intermediates A1-A4 with intermediates D18-28, whose preparations are outlined in schemes D and D2.

TABLE 3

| Example | Structure | Name | MS [M + H]$^+$ | LRRK2 IC$_{50}$ |
|---|---|---|---|---|
| 40 | 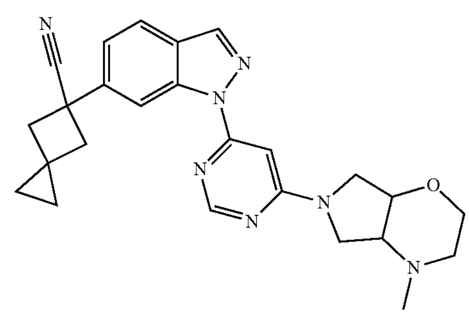 [SMILES: CN1CCOC2CN(c3cc(-n4ncc5ccc(C6(C#N)CC7(CC7)C6)cc54)ncn3)CC21] | 5-(1-(6-(4-methylhexahydropyrrolo[3,4-b][1,4]oxazin-6(2H)-yl)pyrimidin-4-yl)-1H-indazol-6-yl)spiro[2.3]hexane-5-carbonitrile, isomer 1 | 442 | 0.9 nM |

TABLE 3-continued

| Example | Structure | Name | MS [M + H]+ | LRRK2 IC$_{50}$ |
|---|---|---|---|---|
| 41 | 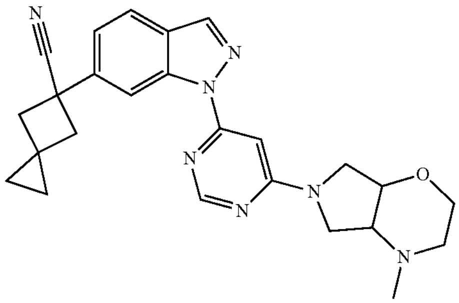 [SMILES: CN1CCOC2CN(c3cc(-n4ncc5ccc(C6(C#N)CC7(CC7)C6)cc54)ncn3)CC21] | 5-(1-(6-(4-ethylhexahydropyrrolo[3,4-b][1,4]oxazin-6(2H)-yl)pyrimidin-4-yl)-1H-indazol-6-yl)spiro[2.3]hexane-5-carbonitrile, isomer 2 | 442 | 1.2 nM |
| 42 | 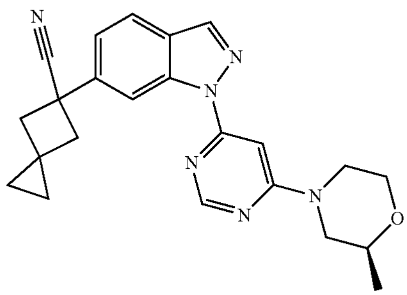 [SMILES: C[C@H]1CN(c2cc(-n3ncc4ccc(C5(C#N)CC6(CC6)C5)cc43)ncn2)CCO1] | (S)-5-(1-(6-(2-methyl-morpholino)pyrimidin-4-yl)-1H-indazol-6-yl)spiro[2.3]hexane-5-carbonitrile | 401 | 5.6 nM |
| 43 | 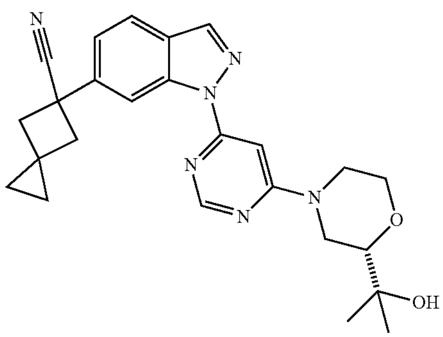 [SMILES: CC(C)(O)[C@@H]1CN(c2cc(-n3ncc4ccc(C5(C#N)CC6(CC6)C5)cc43)ncn2)CCO1] | (S)-5-(1-(6-(2-(2-hydroxypropan-2-yl)morpholino)pyrimidin-4-yl)-1H-indazol-6-yl)spiro[2.3]hexane-5-carbonitrile | 445 | 0.9 nM |
| 44 | 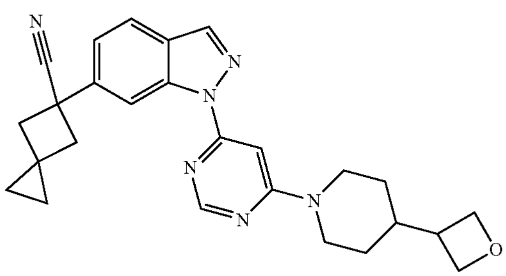 [SMILES: N#CC1(c2ccc3cnn(-c4cc(N5CCC(C6COC6)CC5)ncn4)c3c2)CC2(CC2)C1] | 5-(1-(6-(4-(oxetan-3-yl)piperidin-1-yl)pyrimidin-4-yl)-1H-indazol-6-yl)spiro[2.3]hexane-5-carbonitrile | 441 | 5.0 nM |
| 45 | 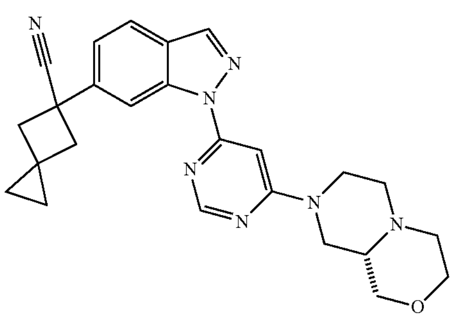 [SMILES: N#CC1(c2ccc3cnn(-c4cc(N5CCN6CCOC[C@@H]6C5)ncn4)c3c2)CC2(CC2)C1] | (S)-5-(1-(6-(hexahydropyrazino[2,1-c][1,4]oxazin-8(1H)-yl)pyrimidin-4-yl)-1H-indazol-6-yl)spiro[2.3]hexane-5-carbonitrile | 442 | 2.0 nM |

TABLE 3-continued

| Example | Structure | Name | MS [M + H]+ | LRRK2 IC$_{50}$ |
|---|---|---|---|---|
| 46 | 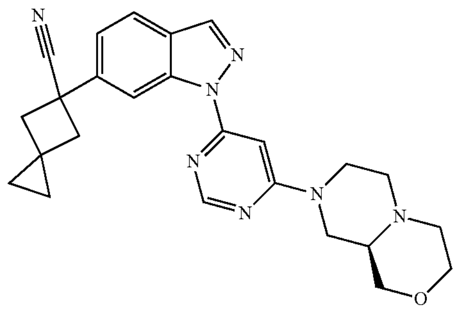 [SMILES: N#CC1(c2ccc3cnn(-c4cc(N5CCN6CCOC[C@H]6C5)ncn4)c3c2)CC2(CC2)C1] | (R)-5-(1-(6-(hexahydropyrazino[2,1-c][1,4]oxazin-8(1H)-yl)pyrimidin-4-yl)-1H-indazol-6-yl)spiro[2.3]hexane-5-carbonitrile | 442 | 7.0 nM |
| 47 | 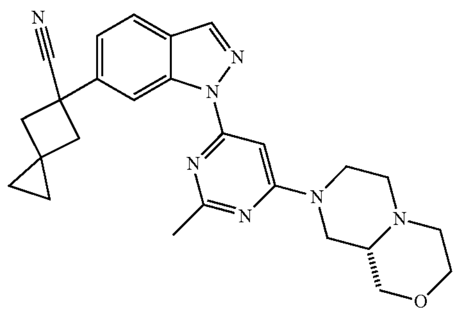 [SMILES: Cc1nc(N2CCN3CCOC[C@@H]3C2)cc(-n2ncc3ccc(C4(C#N)CC5(CC5)C4)cc32)n1] | (S)-5-(1-(6-(hexahydropyrazino[2,1-c][1,4]oxazin-8(1H)-yl)-2-methylpyrimidin-4-yl)-1H-indazol-6-yl)spiro[2.3]hexane-5-carbonitrile | 456 | 3.2 nM |
| 48 | 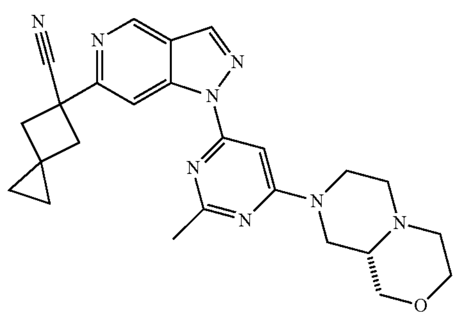 [SMILES: Cc1nc(N2CCN3CCOC[C@@H]3C2)cc(-n2ncc3cnc(C4(C#N)CC5(CC5)C4)cc32)n1] | (S)-5-(1-(6-(hexahydropyrazino[2,1-c][1,4]oxazin-8(1H)-yl)-2-methylpyrimidin-4-yl)-1H-pyrazolo[4,3-c]pyridin-6-yl)spiro[2.3]hexane-5-carbonitrile | 457 | 20.2 nM |
| 49 | 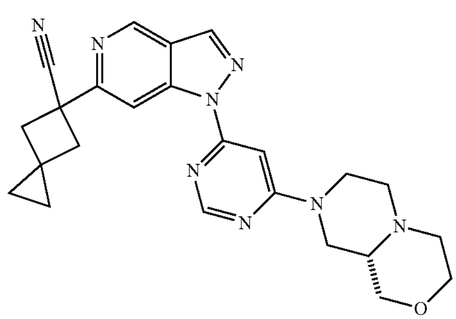 [SMILES: N#CC1(c2cc3c(cn2)cnn3-c2cc(N3CCN4CCOC[C@@H]4C3)ncn2)CC2(CC2)C1] | (S)-5-(1-(6-(hexahydropyrazino[2,1-c][1,4]oxazin-8(1H)-yl)pyrimidin-4-yl)-1H-pyrazolo[4,3-c]pyridin-6-yl)spiro[2.3]hexane-5-carbonitrile | 443 | 8.8 nM |

Examples 50, 51, and 52

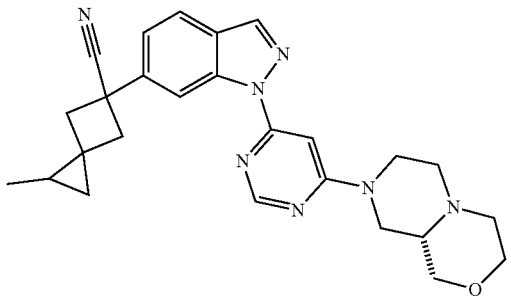 [SMILES: CC1CC12CC(C#N)(c1ccc3cnn(-c4cc(N5CCN6CCOC[C@@H]6C5)ncn4)c3c1)C2]

5-(1-(6-4S)-hexahydropyrazino[2,1-c][1,4]oxazin-8(1H)-yl)pyrimidin-4-yl)-1H-indazol-6-yl)-1-methyl-spiro[2.3]hexane-5-carbonitrile peaks OJ-H-1 (EXAMPLE 50), OJ-H-2 (EXAMPLE 51) and IG-2 (EXAMPLE 52)

A vial containing (S)-8-(6-chloropyrimidin-4-yl)octahydropyrazino[2,1-c][1,4]oxazine (INTERMEDIATE D25, 0.046 g, 0.181 mmol) and 5-(1H-indazol-6-yl)-1-methyl-spiro[2.3]hexane-5-carbonitrile (INTERMEDIATE A4, 0.043 g, 0.181 mmol), $Cs_2CO_3$ (0.177 g, 0.544 mmol) and Josiphos Pd G3 (0.017 g, 0.018 mmol) was evacuated and charged 3× with nitrogen, then suspended/dissolved in dioxane (1.0 ml), stirred at 50° C. overnight, cooled to room temperature, and partitioned between ethyl acetate and water. The organic layer was washed with water 2× more, then dried the organic over sodium sulfate, filtered and evaporated. The product was purified by silica gel chromatography, eluting with 3:1 EtOAc:EtOH in DCM as a gradient, then purified by chiral SFC. SFC Purification Conditions: Co-Solvent: 40% (EtOH+0.2% DIPA), column: IG, 21×250 mm LCMS of the two purified peaks shows a major and minor (RT: 8.24 min) isomer, so they were then each separated by reverse phase HPLC (C18 column, water/CH3CN modified with 0.05% TFA as eluent). The two reverse phase separations were done and the compounds returned as TFA salts. The mixture was partitioned between ethyl acetate and aq. $NaHCO_3$. The organic layer was dried over sodium sulfate, filtered and evaporated to give clean IG peak 1 (RT: 6.82) and IG peak 2 (RT: 8.24 min). Each of these were then resubmitted for chiral SFC. Separation of IG peak 1 was achieved (OJ-H column, 30% (MeOH+0.2% DIPA)). OJ-H Peak 1 (RT: 3.39 min) corresponded to EXAMPLE 50. $^1$H-NMR ($CDCl_3$, 500 MHz): δ 9.14 (s, 1H), 8.60 (s, 1H), 8.21 (s, 1H), 7.79 (d, J=8.5 Hz, 1H), 7.46 (dd, J=8.25 Hz, 2 Hz, 1H), 7.18 (s, 1H), 4.42 (m, 1H), 4.34 (m, 1H), 3.88 (m, 2H), 3.76 (m, 1H), 3.42 (m, 1H), 3.36 (t, J=10.5 Hz, 1H), 3.21 (m, 1H), 3.11 (d, J=12 Hz, 1H), 2.99 (d, J=12 Hz, 1H), 2.90 (d, J=11 Hz, 1H), 2.83 (d, J=12 Hz, 1H), 2.79 (d, J=11.5 Hz, 1H), 2.75 (d, J=12 Hz, 1H), 2.69 (t, J=11.5 Hz, 1H), 2.47-2.32 (m, 3H), 1.05 (d, J=6 Hz, 3H), 0.90 (m, 2H), 0.36 (m, 1H). MS[M+H]$^+$: 456 LRRK2 $IC_{50}$: 4.4 nM.

OJ-H Peak 2 (RT: 4.18 min) corresponded to EXAMPLE 51. $^1$H-NMR ($CDCl_3$, 500 MHz): δ 9.15 (s, 1H), 8.61 (s, 1H), 8.21 (s, 1H), 7.79 (d, J=8.5 Hz, 1H), 7.46 (dd, J=8.25 Hz, 2 Hz, 1H), 7.17 (s, 1H), 4.41 (m, 1H), 4.34 (m, 1H), 3.88 (m, 2H), 3.76 (m, 1H), 3.36 (t, J=11 Hz, 1H), 3.21 (m, 1H), 3.08 (d, J=12 Hz, 1H), 3.00 (d, J=12 Hz, 1H), 2.89 (m, 2H), 2.74 (d, J=12 Hz, 2H), 2.68 (t, J=11.5 Hz, 1H), 2.47-2.32 (m, 3H), 1.13 (d, J=6.5 Hz, 3H), 1.11, (m, 1H), 0.80 (dd, J=8.75 Hz, 5 Hz, 1H), 0.23 (t, J=5.5 Hz, 1H). MS[M+H]$^+$: 456 LRRK2 $IC_{50}$: 9.8 nM.

IG Peak 2 (RT: 8.24 min) corresponds to EXAMPLE 52. $^1$H-NMR ($CDCl_3$, 500 MHz): δ 9.15 (s, 1H), 8.61 (s, 1H), 8.21 (s, 1H), 7.79 (d, J=8.5 Hz, 1H), 7.46 (dd, J=8.25 Hz, 2 Hz, 1H), 7.17 (s, 1H), 4.41 (m, 1H), 4.34 (m, 1H), 3.88 (m, 2H), 3.76 (m, 1H), 3.36 (t, J=11 Hz, 1H), 3.21 (m, 1H), 3.08 (d, J=12 Hz, 1H), 3.00 (d, J=12 Hz, 1H), 2.89 (m, 2H), 2.74 (m, 2H), 2.68 (t, J=12 Hz, 1H), 2.47-2.32 (m, 3H), 1.14 (d, J=6.5 Hz, 3H), 0.99 (m, 1H), 0.80 (dd, J=8.75 Hz, 5 Hz, 1H), 0.23 (t, J=5.5 Hz, 1H). MS[M+H]$^+$: 456 LRRK2 $IC_{50}$: 2.4 nM

Examples 53, 54, 55 and 56

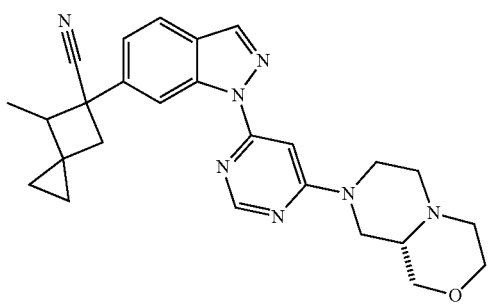 [SMILES: CC1C2(CC2)CC1(C#N)c1ccc2cnn(-c3cc(N4CCN5CCOC[C@@H]5C4)ncn3)c2c1]

5-(1-(6-((S)-hexahydropyrazino[2,1-c][1,4]oxazin-8(1H)-yl)pyrimidin-4-yl)-1H-indazol-6-yl)-4-methyl-spiro[2.3]hexane-5-carbonitrile, Isomer 1 (EXAMPLE 53), Isomer 2 (EXAMPLE 54), Isomer 3 (EXAMPLE 55) and Isomer 4 (EXAMPLE 56)

A vial containing (S)-8-(6-chloropyrimidin-4-yl)octahydropyrazino[2,1-c][1,4]oxazine (INTERMEDIATE D25, 0.078 g, 0.308 mmol) and 5-(1H-indazol-6-yl)-4-methyl-spiro[2.3]hexane-5-carbonitrile (INTERMEDIATE A3, 0.073 g, 0.308 mmol), $Cs_2CO_3$ (0.301 g, 0.923 mmol) and Josiphos Pd G3 (0.028 g, 0.031 mmol) was evacuated and charged 3× with nitrogen, then suspended/dissolved in dioxane (1.50 ml) stirred at 50° C. overnight, cooled to room temperature, and partitioned between ethyl acetate and water. The organic layer was washed with water 2× more, then dried over sodium sulfate, filtered and evaporated. The mixture was purified by silica gel column, eluting with a gradient of 3:1 EtOAc:EtOH in hexanes. The major peak contained a front shoulder; TLC of the requisite fractions showed mixed and clean fractions. Repurification of the mixed fractions was achieved as described above. The pure fractions were separated by chiral SFC (AS-H column, 30% (MeOH+0.2% DIPA) as co-solvent. 3:1 ratio of products isolated). AS-H Peak 1 (major, RT=3.92 min) was further separated as follows: IG column, 40% (MeOH/ACN 1/1+0.2% DIPA). A 1/1 ratio of products (IG Peak 1 (RT=10.97 min) was EXAMPLE 53 and IG Peak 2 (RT=11.32 min) was EXAMPLE 54). The AS-H Peak 2 (minor, RT=4.78 and 5.59 min, which did not separate preparatively) was further separated as follows: OJ-H column, 20% (MeOH+0.2% DIPA). The OJ-H Peak 1 (RT=2.72 min) was EXAMPLE 55. The OJ-H Peak 2 (RT=3.22 min) was EXAMPLE 56.

IG Peak 1 (RT: 10.97 min) corresponded to EXAMPLE 53. $^1$H-NMR (CDCl$_3$, 500 MHz): δ 9.08 (s, 1H), 8.61 (s, 1H), 8.20 (s, 1H), 7.78 (d, J=8.5 Hz, 1H), 7.42 (d, J=8.25 Hz, 1H), 7.17 (s, 1H), 4.41 (m, 1H), 4.35 (m, 1H), 3.88 (m, 2H), 3.76 (m, 1H), 3.36 (t, J=10.5 Hz, 1H), 3.21 (m, 1H), 3.09 (q, J=11.5 Hz, 7 Hz, 1H), 2.99 (d, J=11.5 Hz, 1H), 2.90 (d, J=12 Hz, 1H), 2.82 (d, J=11.5 Hz, 1H), 2.74 (d, J=11.5 Hz, 1H), 2.68 (t, J=12 Hz, 1H), 2.47-2.32 (m, 3H), 1.29 (d, J=7 Hz, 3H), 0.88 (m, 1H), 0.61 (m, 2H), 0.50 (m, 1H). MS[M+H]$^+$: 456 LRRK2 IC$_{50}$: 7.9 nM.

IG Peak 2 (RT: 11.32 min) corresponded to EXAMPLE 54. $^1$H-NMR (CDCl$_3$, 500 MHz): δ 9.08 (s, 1H), 8.61 (s, 1H), 8.20 (s, 1H), 7.78 (d, J=8.5 Hz, 1H), 7.42 (dd, J=8.25 Hz, 1.5 Hz, 1H), 7.17 (s, 1H), 4.41 (m, 1H), 4.35 (m, 1H), 3.88 (m, 2H), 3.76 (m, 1H), 3.36 (t, J=10.5 Hz, 1H), 3.21 (m, 1H), 3.09 (q, J=11.5 Hz, 7 Hz, 1H), 2.99 (d, J=11.5 Hz, 1H), 2.90 (d, J=11.5 Hz, 1H), 2.82 (d, J=12 Hz, 1H), 2.74 (d, J=12 Hz, 1H), 2.68 (t, J=12 Hz, 1H), 2.47-2.32 (m, 3H), 1.29 (d, J=6.5 Hz, 3H), 0.88 (m, 1H), 0.61 (m, 2H), 0.50 (m, 1H). MS[M+H]$^+$: 456 LRRK2 IC$_{50}$: 1.7 nM.

OJ-H Peak 1 (RT: 2.72 min) corresponded to EXAMPLE 55. $^1$H-NMR (CDCl$_3$, 500 MHz): δ 9.17 (s, 1H), 8.59 (s, 1H), 8.21 (s, 1H), 7.79 (d, J=8 Hz, 1H), 7.46 (dd, J=8.5 Hz, 1.5 Hz, 1H), 7.19 (s, 1H), 4.41 (m, 1H), 4.34 (m, 1H), 3.88 (m, 2H), 3.76 (m, 1H), 3.40 (q, J=11.5 Hz, 7 Hz, 1H), 3.36 (t, J=10.5 Hz, 1H), 3.21 (m, 1H), 3.14 (d, J=12.5 Hz, 1H), 2.94 (d, J=12.5 Hz, 1H), 2.90 (d, J=11.5 Hz, 1H), 2.74 (d, J=12 Hz, 1H), 2.68 (t, J=12 Hz, 1H), 2.47-2.32 (m, 3H), 0.79-0.62 (m, 4H), 0.56 (d, J=7 Hz, 3H). MS[M+H]$^+$: 456 LRRK2 IC$_{50}$: 34.0 nM.

OJ-H Peak 2 (RT: 3.22 min) corresponded to EXAMPLE 56. $^1$H-NMR (CDCl$_3$, 500 MHz): δ 9.17 (s, 1H), 8.59 (s, 1H), 8.21 (s, 1H), 7.79 (d, J=8.5 Hz, 1H), 7.46 (dd, J=8.25 Hz, 1.5 Hz, 1H), 7.19 (s, 1H), 4.41 (m, 1H), 4.34 (m, 1H), 3.88 (m, 2H), 3.76 (m, 1H), 3.40 (q, J=11.5 Hz, 7 Hz 1H), 3.36 (t, J=10.5 Hz, 1H), 3.21 (m, 1H), 3.14 (d, J=12 Hz, 1H), 2.94 (d, J=12.5 Hz, 1H), 2.90 (d, J=11 Hz, 1H), 2.74 (d, J=12 Hz, 1H), 2.68 (t, J=12 Hz, 1H), 2.47-2.32 (m, 3H), 0.79-0.62 (m, 4H), 0.56 (d, J=7 Hz, 3H). MS[M+H]$^+$: 456 LRRK2 IC$_{50}$: 3.0 nM.

The compounds of the invention, surprisingly and advantageously, exhibit good potency, in some embodiments exceptional potency, as inhibitors of LRRK2 kinase. The IC$_{50}$ values reported herein were measured as follows.

Biological Assay: LRRK2 Km ATP LanthaScreen™ Assay

The LRRK2 kinase activity reported herein as IC50 values was determined with LanthaScreen™ technology from Life Technologies Corporation (Carlsbad, Calif.) using GST-tagged truncated human mutant G2019S LRRK2 in the presence of the fluorescein-labeled peptide substrate LRRKtide, also from Life Technologies. The data presented for the Km ATP LanthaScreen™ Assay represents mean IC$_{50}$ values based on several test results and may have reasonable deviations depending on the specific conditions and reagents used. Assays were performed in the presence of 134 µM ATP (Km ATP). Upon completion, the assay was stopped and phosphorylated substrate detected with a terbium (Tb)-labeled anti-pERM antibody (cat. no. PV4898). The compound dose response was prepared by diluting a 10 mM stock of compound to a maximum concentration of 9.99 µM in 100% dimethylsulfoxide followed by custom fold serial dilution in dimethylsulfoxide nine times. Twenty nanoliters of each dilution was spotted via a Labcyte Echo onto a 384-well black-sided plate (Corning 3575) followed by 15 µl of a 1.25 nM enzyme solution in 1x assay buffer (50 mM Tris pH 8.5, 10 mM MgCl2, 0.01% Brij-35, 1 mM EGTA, 2 mM dithiothreitol, 0.05 mM sodium orthovanadate) Following a 15-minute incubation at room temperature, the kinase reaction was started with the addition of 5 µl of 400 nM fluorescein-labeled LRRKtide peptide substrate and 134 µM ATP solution in 1x assay buffer. The reaction was allowed to progress at ambient temperature for 90 minutes. The reaction was then stopped by the addition of 20 µl of TR-FRET Dilution Buffer (Life Technologies, Carlsbad, Calif.) containing 2 nM Tb-labeled anti-phospho LRRKtide antibody and 10 mM EDTA (Life Technologies, Carlsbad, Calif.). After an incubation of 1 hour at room temperature, the plate was read on an EnVision multimode plate reader (Perkin Elmer, Waltham, Mass.) with an excitation wavelength of 337 nm (Laser) and a reading emission at both 520 and 495 nm. Compound IC50s were interpolated from nonlinear regression best fits of the log of the final compound concentration, plotted as a function of the 520/495-nm emission ratio using Activity base. Abase uses a 4 parameter (4P) logistic fit based on the Levenberg-Marquardt algorithm.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound having a structural Formula (I):

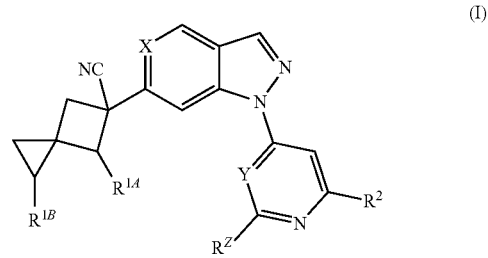

(I)

or a pharmaceutically acceptable salt thereof, wherein:
$R^{1A}$ is H or CH$_3$;
$R^{1B}$ is H or CH$_3$;
X is C($R^X$) or N;
$R^X$ is H, F, Cl, or —(C$_1$-C$_6$)alkyl;
Y is CH or N;
$R^Z$ is H, F, —(C$_1$-C$_6$)alkyl, —NH$_2$, —NH(C$_1$-C$_6$)alkyl, —N((C$_1$-C$_6$)alkyl)$_2$, —O(C$_1$-C$_6$)alkyl, —S(C$_1$-C$_6$)alkyl, —(C$_1$-C$_6$)alkyl-OH, —(C$_1$-C$_6$)alkyl-O—(C$_1$-C$_6$)alkyl,

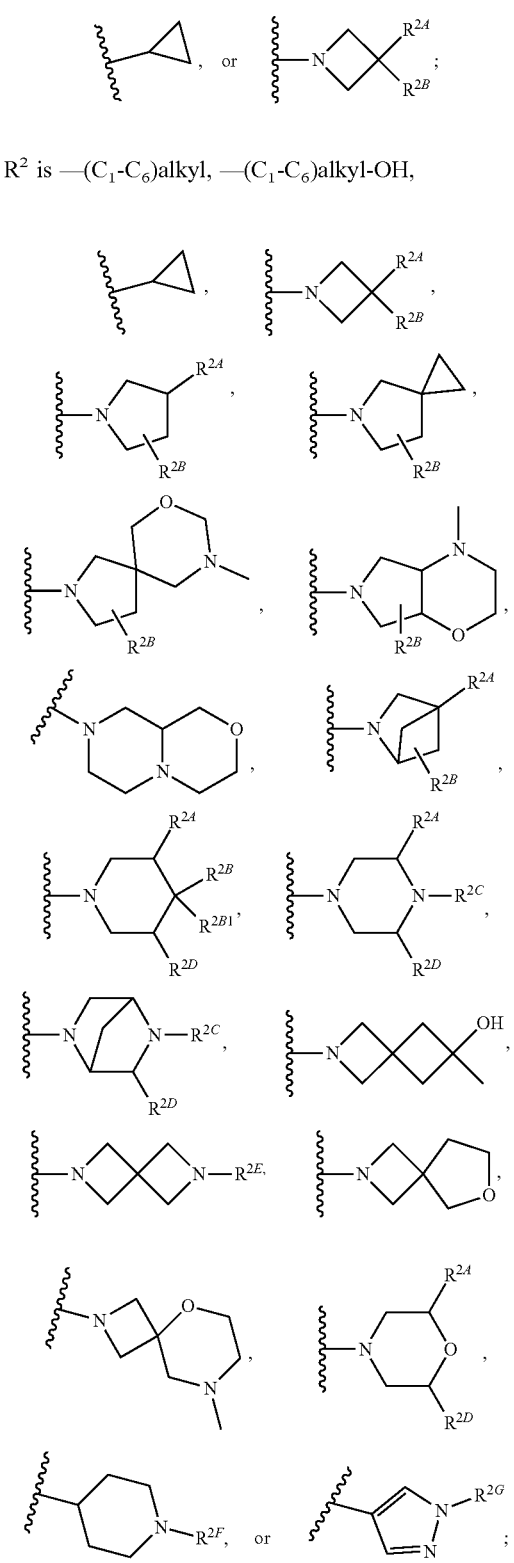

$R^2$ is —($C_1$-$C_6$)alkyl, —($C_1$-$C_6$)alkyl-OH, wherein:
$R^{2A}$ is H, F, —OH, —($C_1$-$C_6$)alkyl, —($C_1$-$C_6$)haloalkyl, —O—($C_1$-$C_6$)alkyl, —C(OH)(($C_1$-$C_6$)alkyl)$_2$, —($C_1$-$C_6$)alkyl-OH, —($C_1$-$C_6$)alkyl-O—($C_1$-$C_6$)alkyl, —C(($C_1$-$C_6$)alkyl)$_2$(OH), cyclopropyl, or

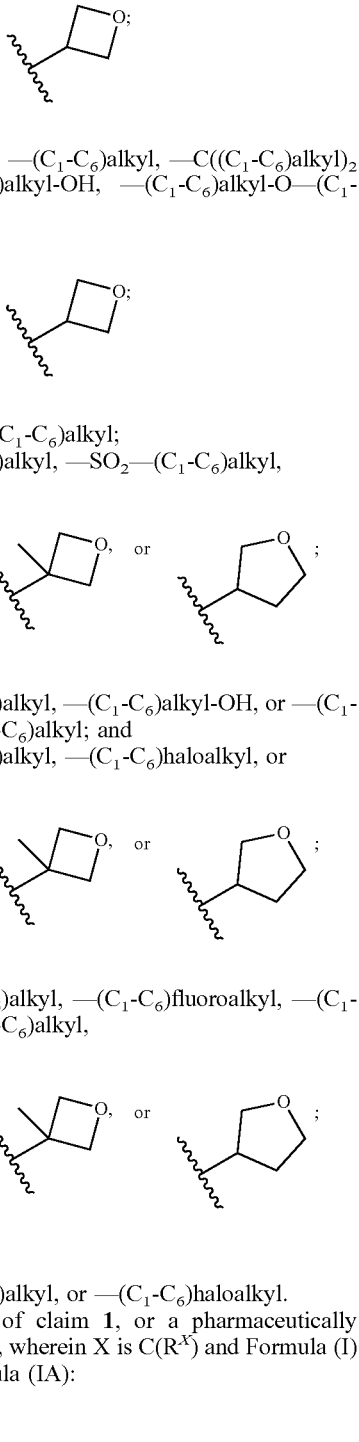

$R^{2B}$ is H, F, —OH, —($C_1$-$C_6$)alkyl, —C(($C_1$-$C_6$)alkyl)$_2$(OH), —($C_1$-$C_6$)alkyl-OH, —($C_1$-$C_6$)alkyl-O—($C_1$-$C_6$)alkyl, or $R^{2B1}$ is H, F, or —($C_1$-$C_6$)alkyl;
$R^{2C}$ is H, —($C_1$-$C_6$)alkyl, —SO$_2$—($C_1$-$C_6$)alkyl, $R^{2D}$ is H, —($C_1$-$C_6$)alkyl, —($C_1$-$C_6$)alkyl-OH, or —($C_1$-$C_6$)alkyl-O—($C_1$-$C_6$)alkyl; and
$R^{2E}$ is H, —($C_1$-$C_6$)alkyl, —($C_1$-$C_6$)haloalkyl, or $R^{2F}$ is H, —($C_1$-$C_6$)alkyl, —($C_1$-$C_6$)fluoroalkyl, —($C_1$-$C_6$)alkyl-O—($C_1$-$C_6$)alkyl, and
$R^{2G}$ is H, —($C_1$-$C_6$)alkyl, or —($C_1$-$C_6$)haloalkyl.

2. The compound of claim 1, or a pharmaceutically acceptable salt thereof, wherein X is C($R^X$) and Formula (I) has a structural Formula (IA):

(IA)

or a pharmaceutically acceptable salt thereof, wherein:
$R^X$ is H, F, Cl, or $CH_3$; and
Y is CH or N.

3. The compound of claim 2, or a pharmaceutically acceptable salt thereof, wherein Y is N.

4. The compound of claim 2, or a pharmaceutically acceptable salt thereof, wherein Y is CH.

5. The compound of claim 1, or a pharmaceutically acceptable salt thereof, wherein Y is N and Formula (I) has a structural Formula (IB):

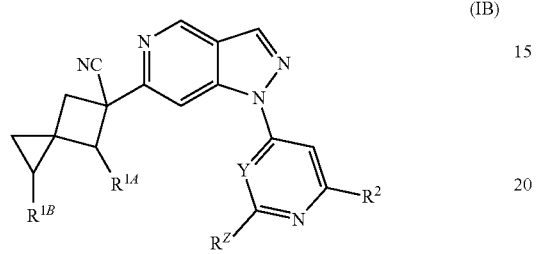

(IB)

or a pharmaceutically acceptable salt thereof, wherein:
Y is CH or N.

6. The compound of claim 5, or a pharmaceutically acceptable salt thereof, wherein Y is N.

7. The compound of claim 5, or a pharmaceutically acceptable salt thereof, wherein Y is CH.

8. A compound of claim 1, or a pharmaceutically acceptable salt thereof, said compound is selected from:

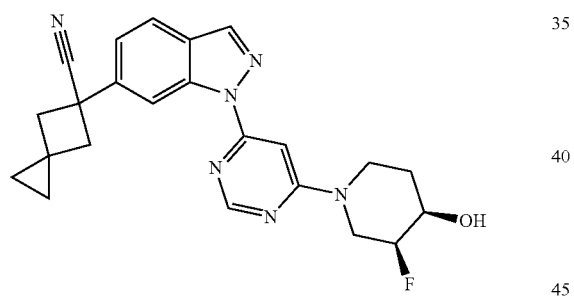

-continued

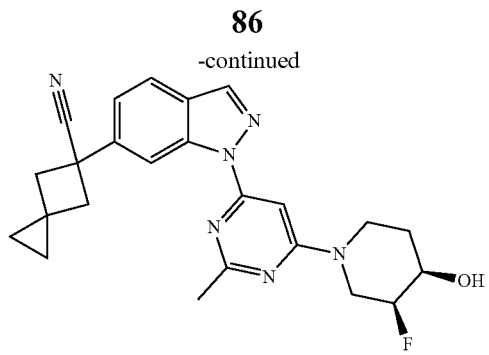

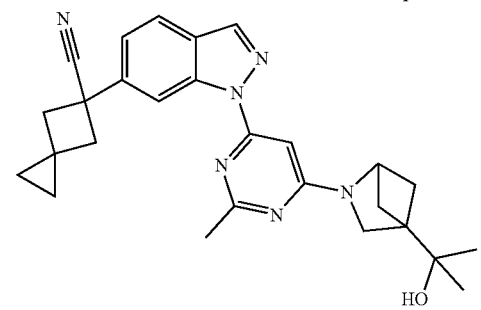

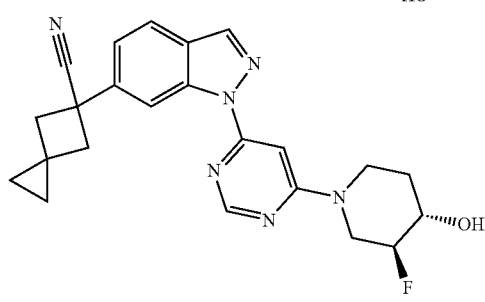

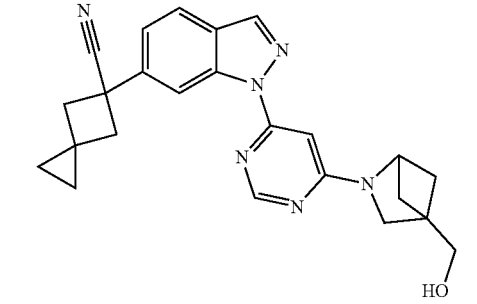

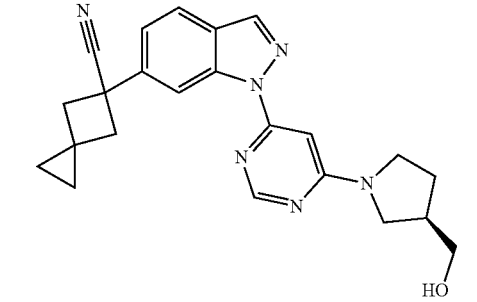

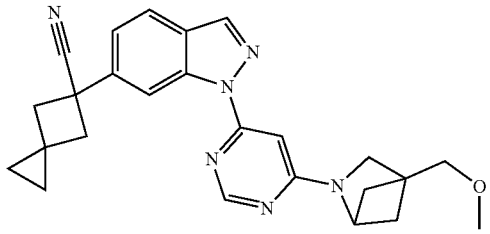

87
-continued
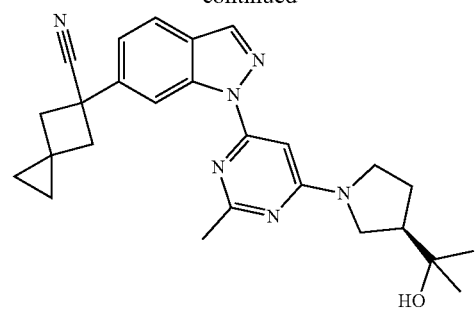
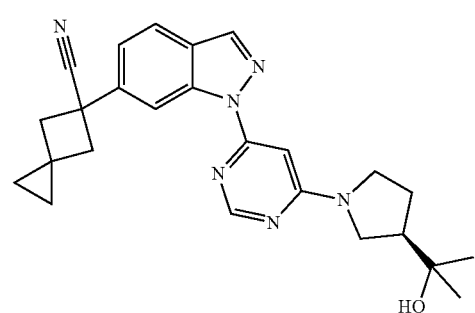
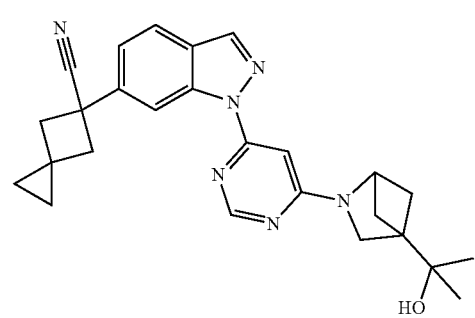
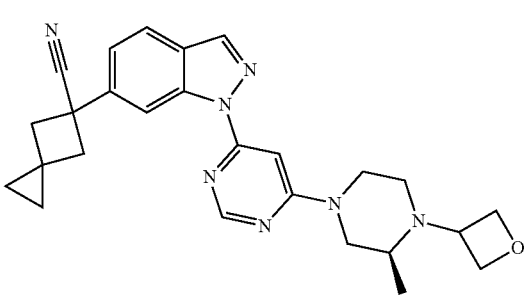
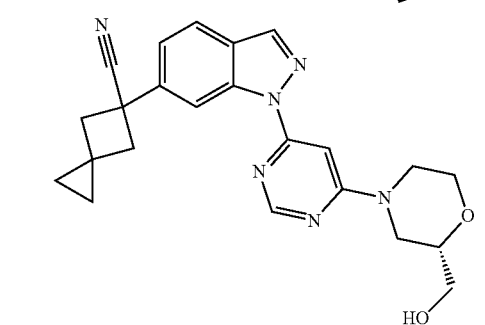
88
-continued
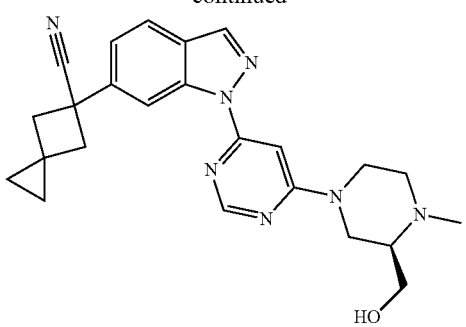
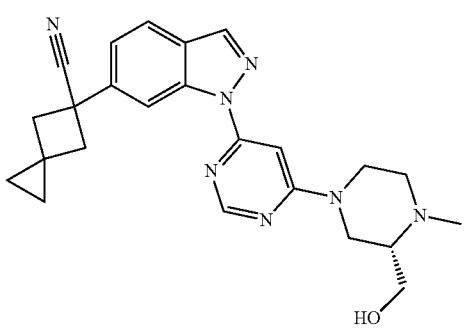
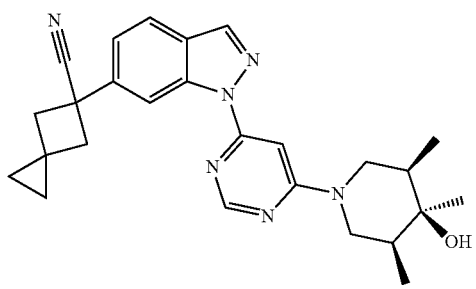
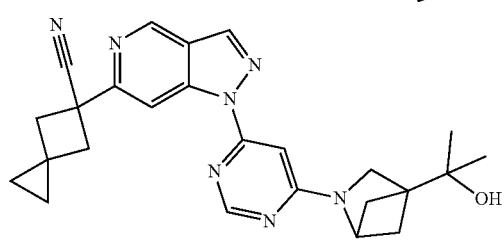
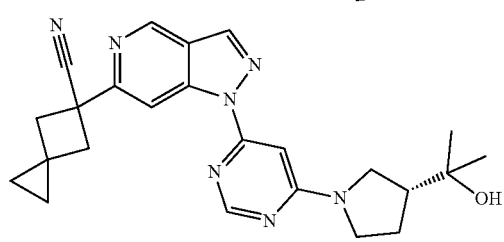
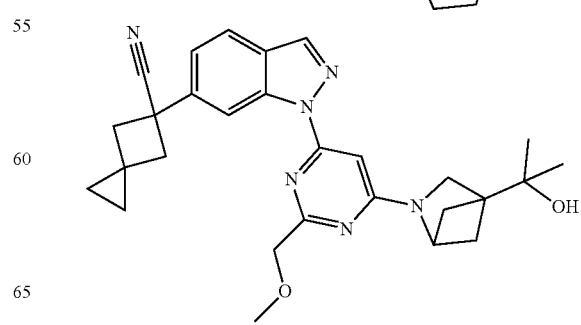

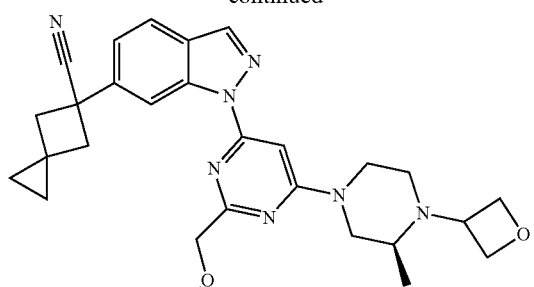
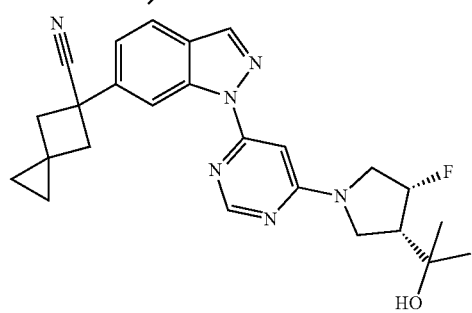
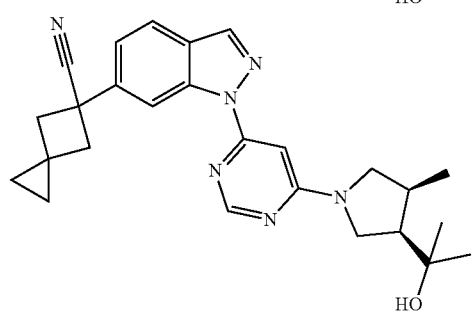
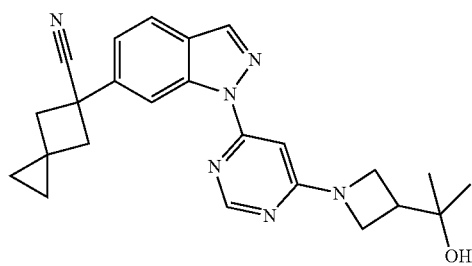
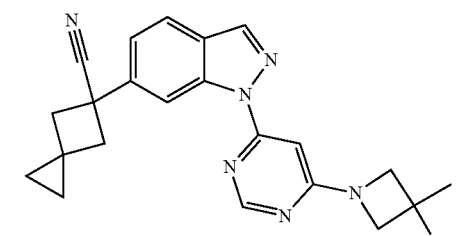
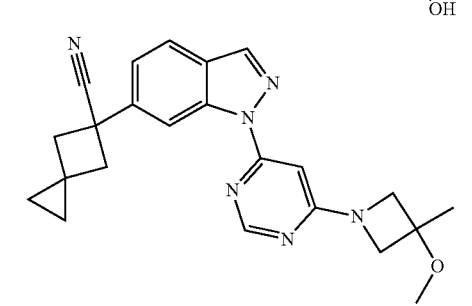
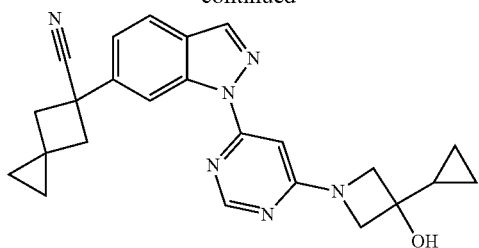
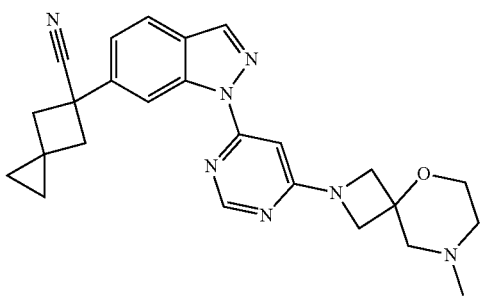
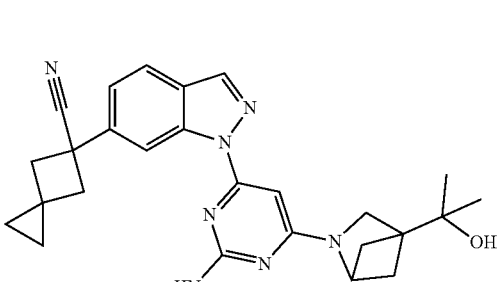
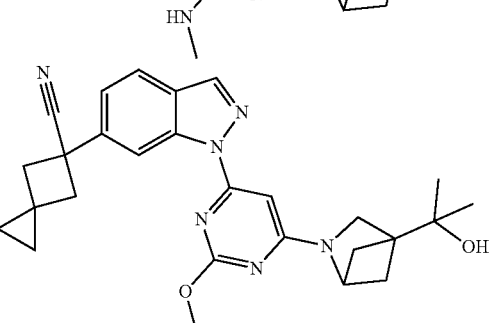
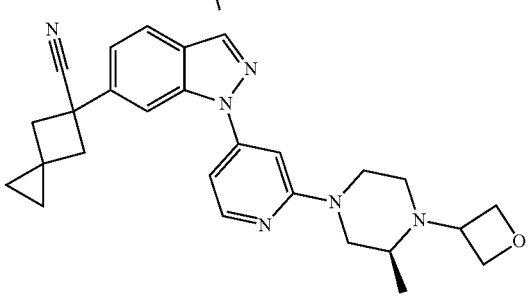
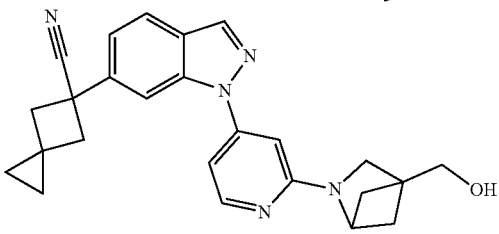

91
-continued
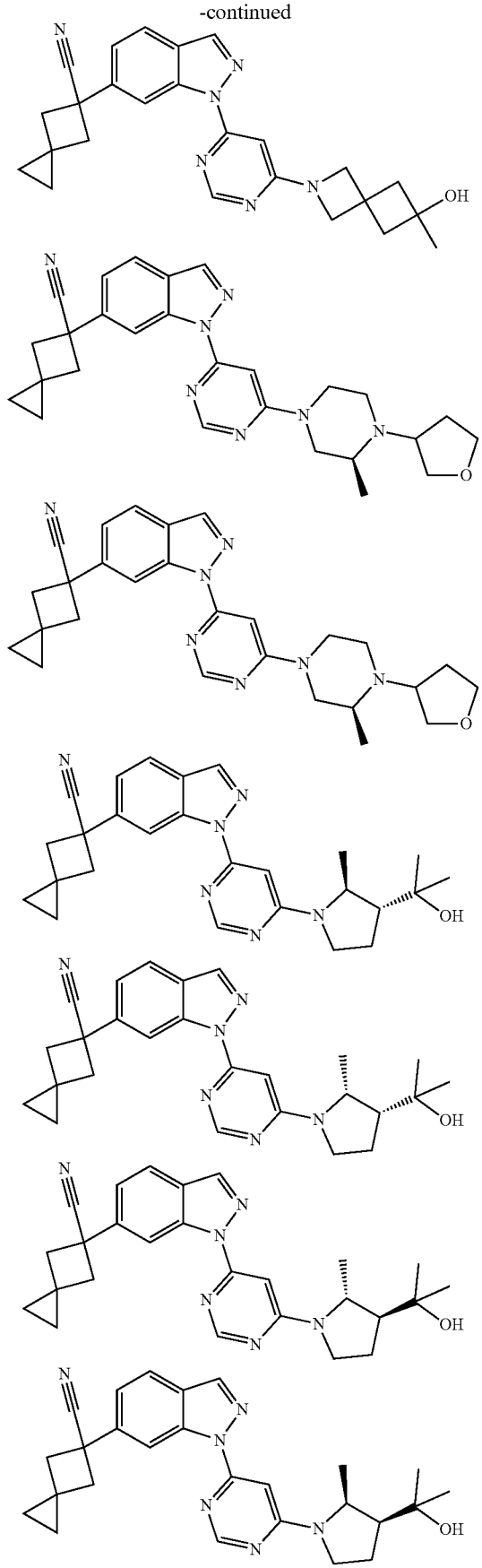
92
-continued
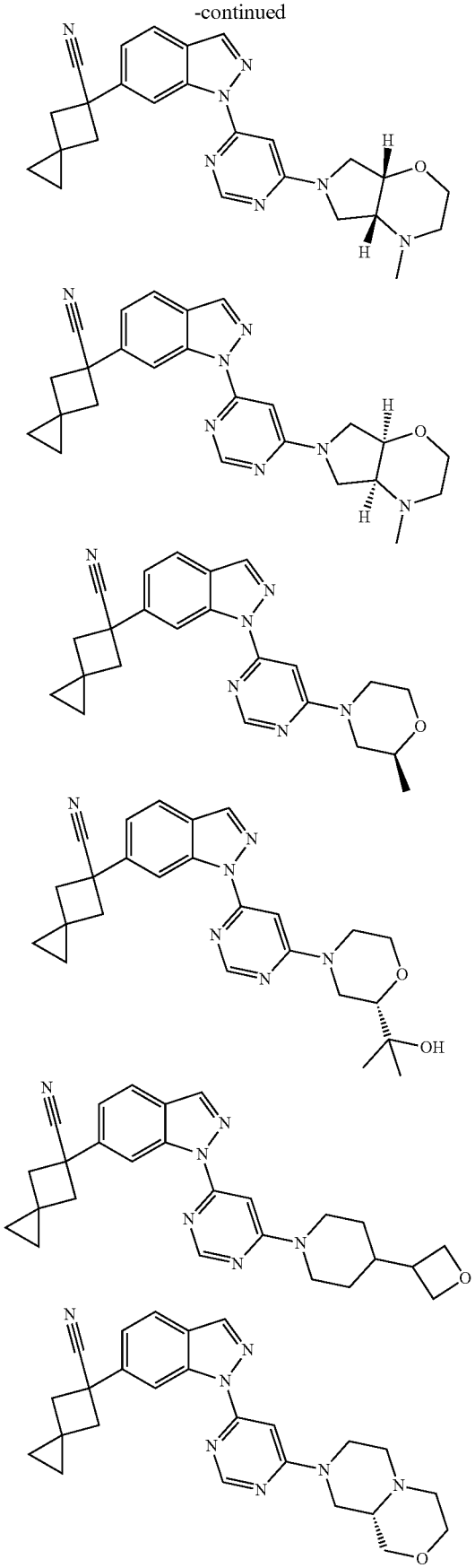

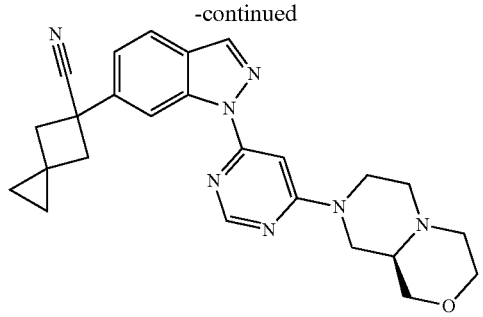
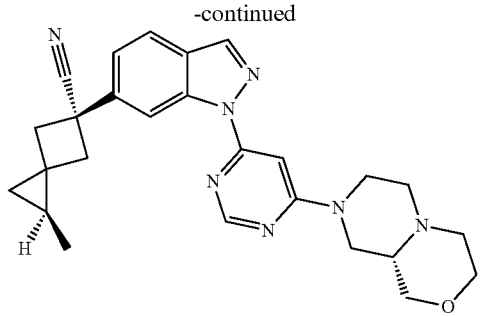
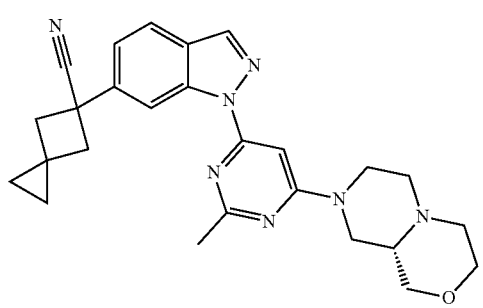
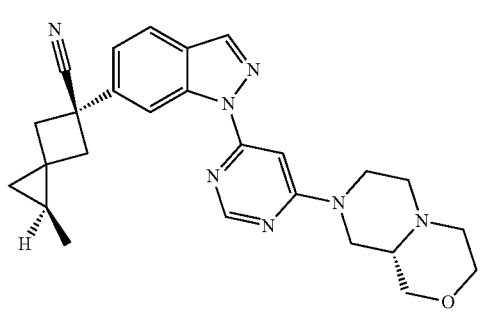
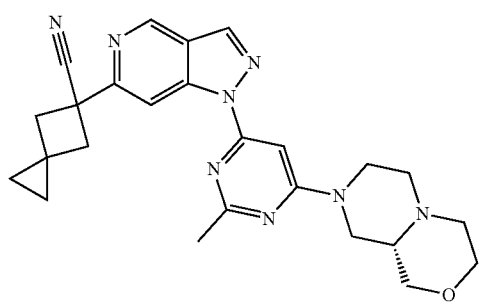
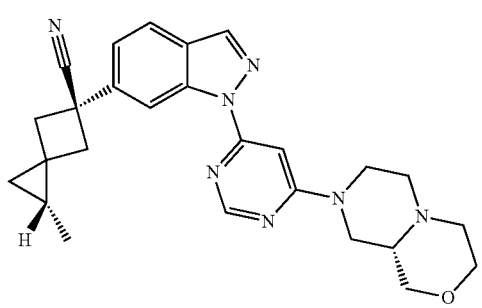
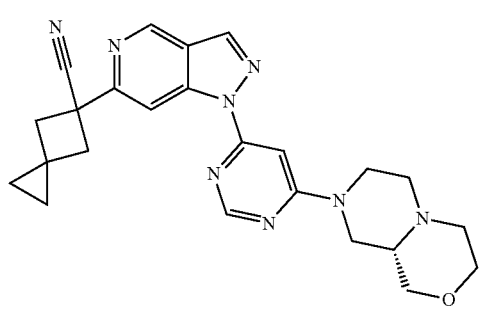
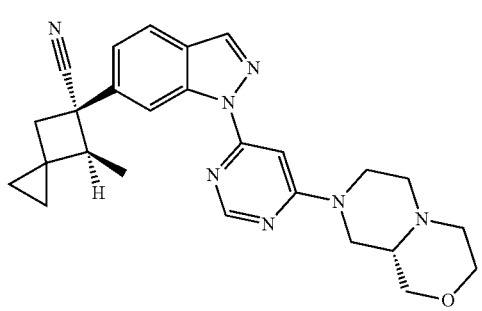
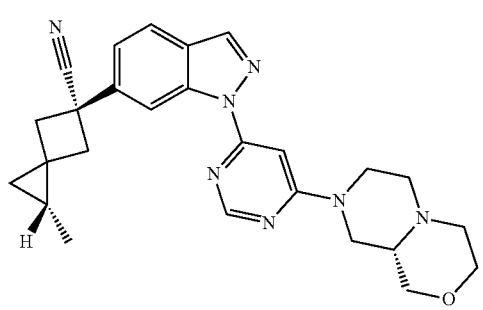
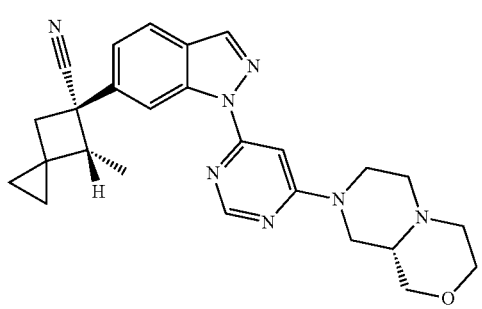

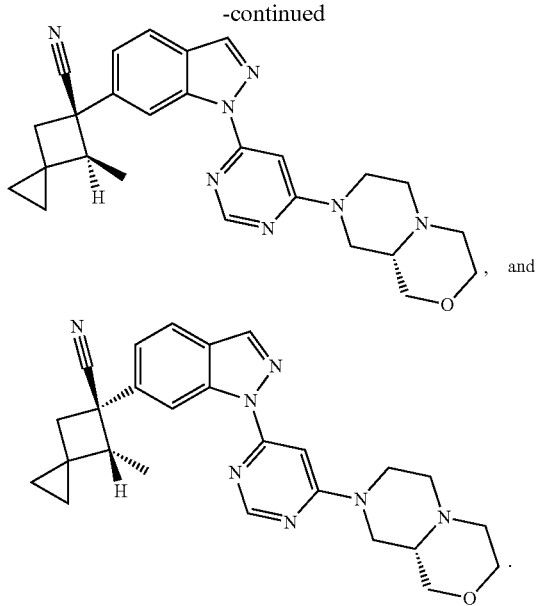

9. A pharmaceutical composition comprising a compound of claim 1, and a pharmaceutically acceptable carrier.

10. A method of treating Parkinson's Disease comprising administering an effective amount of a compound of claim 1, or a pharmaceutically acceptable salt thereof, to a person in need thereof.

11. A method for the treatment of an indication in which LRRK2 kinase is involved comprising administering to a subject in need thereof an effective amount of a compound according to claim 1, or a pharmaceutically acceptable salt thereof, said indication selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17, neuroinflammation associated with of microglial inflammatory responses associated with multiple sclerosis, HIV-induced dementia, ALS, ischemic stroke, traumatic brain injury and spinal cord injury, lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

* * * * *